United States Patent
Lo et al.

(10) Patent No.: US 10,744,116 B2
(45) Date of Patent: Aug. 18, 2020

(54) DETECTION AND TREATMENT OF ANTI-PD-1 THERAPY RESISTANT METASTATIC MELANOMAS

(71) Applicant: THE REGENTS OF THE UNIVERSITY OF CALIFORNIA, Oakland, CA (US)

(72) Inventors: Roger S. Lo, Los Angeles, CA (US); Willy Hugo, Los Angeles, CA (US); Antoni Ribas, Los Angeles, CA (US); Jesse Zaretsky, Santa Monica, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 142 days.

(21) Appl. No.: 16/084,911

(22) PCT Filed: Mar. 16, 2017

(86) PCT No.: PCT/US2017/022811
§ 371 (c)(1),
(2) Date: Sep. 13, 2018

(87) PCT Pub. No.: WO2017/161188
PCT Pub. Date: Sep. 21, 2017

(65) Prior Publication Data
US 2019/0076399 A1 Mar. 14, 2019

Related U.S. Application Data

(60) Provisional application No. 62/309,204, filed on Mar. 16, 2016.

(51) Int. Cl.
| | |
|---|---|
| G01N 31/00 | (2006.01) |
| A61K 31/385 | (2006.01) |
| C12Q 1/6886 | (2018.01) |
| C07K 16/28 | (2006.01) |
| G16B 20/00 | (2019.01) |
| A61P 35/00 | (2006.01) |
| G16B 5/00 | (2019.01) |
| G16B 25/00 | (2019.01) |
| A61K 31/337 | (2006.01) |
| A61K 31/427 | (2006.01) |
| A61K 39/395 | (2006.01) |
| A61K 45/06 | (2006.01) |
| C12Q 1/686 | (2018.01) |
| G16B 25/10 | (2019.01) |

(52) U.S. Cl.
CPC .......... *A61K 31/385* (2013.01); *A61K 31/337* (2013.01); *A61K 31/427* (2013.01); *A61K 39/39558* (2013.01); *A61K 45/06* (2013.01); *A61P 35/00* (2018.01); *C07K 16/2818* (2013.01); *C12Q 1/686* (2013.01); *C12Q 1/6886* (2013.01); *G16B 5/00* (2019.02); *G16B 20/00* (2019.02); *G16B 25/00* (2019.02); *C12Q 2600/106* (2013.01); *C12Q 2600/156* (2013.01); *C12Q 2600/158* (2013.01); *G16B 25/10* (2019.02)

(58) Field of Classification Search
None
See application file for complete search history.

(56) References Cited

U.S. PATENT DOCUMENTS

2016/0123964 A1   5/2016   Tumeh et al.

OTHER PUBLICATIONS

Hugo, Willy, et al. Genomic and Transcriptomic Features of Response to Anti-PD-1Therapy in Metastatic Melanoma. Cell Mar. 24, 2016; 165(1): 35-44. doi:10.1016/j.cell.2016.02.065.
Hugo, Willy, et al. Non-genomic and Immune Evolution of Melanoma Acquiring MAPKi Resistance. Cell 2015, 162(6):1271-86.
Johnson, Douglas B., et al. Melanoma-specific MHC-11 expression represents a tumour-autonomous phenotype and predicts response to anti-PD-11PD-L 1 therapy. Nat Commun. Jan. 29, 2016, 7:10582.
Le, D.T., et al. PD-1 Blockade in Tumors with Mismatch-Repair Deficiency. N Engl J Med. 2015,372(26):2509-20.
Muller, Judith, et al. Low MITF/AXL ratio predicts early resistance to multiple targeted drugs in melanoma. Nat Commun. 2014, 5:5712.
International Search Report for PCT/US17/22811 (WO2017161188 Published Sep. 21, 2017).

*Primary Examiner* — Lisa V Cook
(74) *Attorney, Agent, or Firm* — Karen S. Canady; Canady +Lortz LLP

(57) ABSTRACT

Methods of predicting or detecting sensitivity to therapeutic effects of anti-PD-1 therapy in a patient suffering from melanoma, as well as for selecting somatic mutanomes and transcriptomes of melanoma biopsies. A tumor sample obtained from the patient is assayed for a measure of anti-PD-1 therapy sensitivity via, for example, whole transcriptome sequencing, antibody based protein quantifications, mass spectrometry based protein quantification, targeted mRNA sequencing, real-time RT-PCR, Sanger sequencing, targeted sequencing and/or whole exome/genome sequencing. Samples are selected that exhibit a higher first enrichment similarity score and/or a lower second enrichment similarity score, and/or at least one measure of sensitivity. A patient whose sample was selected herein as a candidate for anti-PD-1 therapy is thereby identified. The method of the invention can further comprise treating the patient with anti-PD-1 therapy, optionally in conjunction with combinatorial therapy.

20 Claims, 15 Drawing Sheets

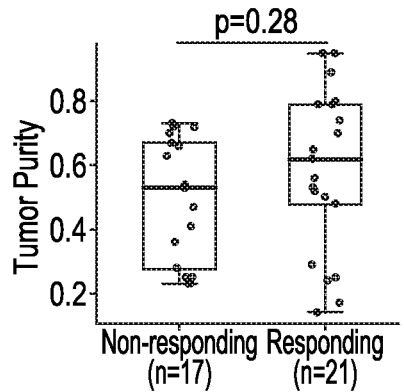
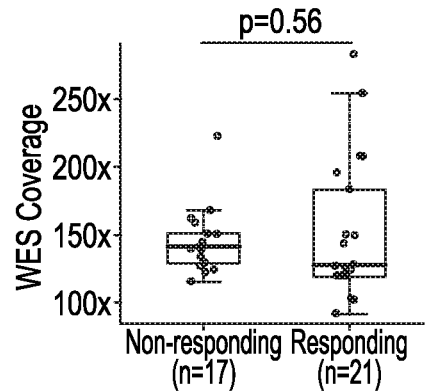
FIG. 4A
FIG. 4B
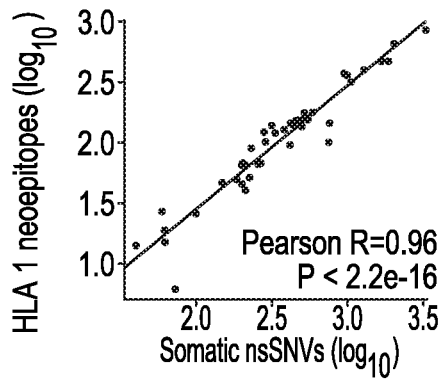
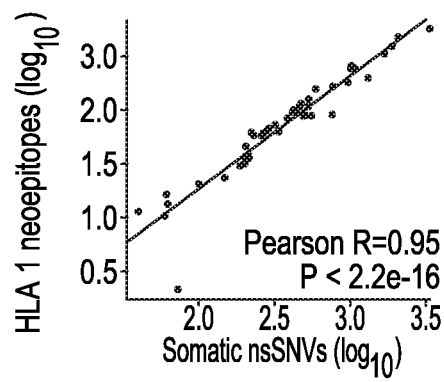
FIG. 4C
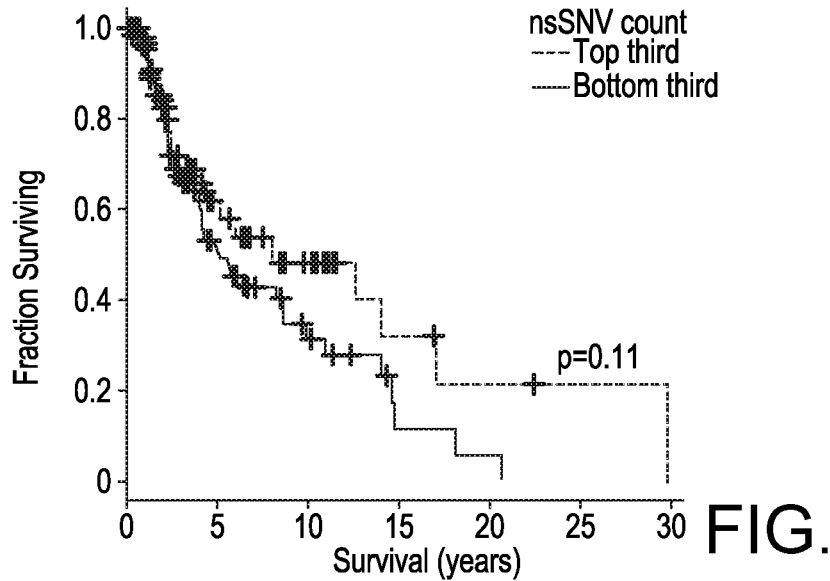
FIG. 4E

DETECTION AND TREATMENT OF ANTI-PD-1 THERAPY RESISTANT METASTATIC MELANOMAS

This application claims the benefit of U.S. Provisional Application No. 62/309,204, filed Mar. 16, 2016, the entire contents of which are incorporated herein by reference. Throughout this application various publications are referenced. The disclosures of these publications in their entireties are hereby incorporated by reference into this application in order to describe more fully the state of the art to which this invention pertains.

STATEMENT REGARDING FEDERALLY SPONSORED RESEARCH

This invention was made with Government support under CA168585, CA176111, and CA197633, awarded by the National Institutes of Health. The Government has certain rights in the invention.

REFERENCE TO A TABLE SUBMITTED VIA EFS-WEB

The content of the ASCII text files of the tables named "UCLA240_TABLE1", "UCLA240_TABLE2", "UCLA240_TABLE3", which are 37 kb, 7 kb, and 362 kb in size, respectively, created on Mar. 14, 2017, and electronically submitted via EFS-Mb with this application, is incorporated herein by reference in its entirety.

TECHNICAL FIELD

The present invention relates generally to detection, diagnosis, monitoring and treatment of cancer, such as melanoma. The invention more specifically pertains to predicting and detecting those cancers that will be sensitive to, or unresponsive to, anti-PD-1 therapy, and thus also to selection of effective treatment strategies.

BACKGROUND

PD-1 immune checkpoint blockade induces a high rate of anti-melanoma response and provides clinical benefits unprecedented with immunotherapy (Hamid et al., 2013; Topalian et al., 2012). This therapeutic approach has also been shown to be active against a growing list of human malignancies, and clinical testing of combinations of PD-1 with other treatment targets has already begun (Sharma and Allison, 2015). However, effective use of anti-PD-1 clinical agents is encumbered mostly by innate resistance, the mechanistic basis of which remains poorly characterized.

In melanoma, the extent of pretreatment and especially treatment-induced T cell infiltration correlates with clinical responses (Tumeh et al., 2014), supporting unleashing of tumor-specific T cells as a mechanistic basis of anti-PD-1 therapy. Preliminary retrospective analyses of clinical data hinted at prior failure of MAPK-targeted therapy being a negative factor for subsequent response to immune checkpoint blockade in melanoma (Puzanov et al., 2015; Ramanujam et al., 2015; Simeone et al., 2015). At the genomic level, the overall mutation load, which may reflect or lead to higher neoepitope load, a smoking signature, and impairment of DNA repair, have been correlated with anti-PD-1 response in non-small cell lung cancers (Rizvi et al., 2015). However, the lack of these response-related features do not robustly preclude response. Thus, there remains a need for an objective assessment of omic-scale features related to both response and resistance as an important step toward patient stratification and identification of combinatorial targets.

There remains a need for improved tools to permit the detection, identification and prognosis of drug resistant cancers, particularly anti-PD-1-resistant melanomas. There also remains a need for targets useful in the detection and treatment of cancer.

SUMMARY

The invention provides a method of selecting somatic mutanomes and transcriptomes of melanoma biopsies. The invention also provides a method of predicting or detecting the responsiveness or sensitivity to therapeutic effects of anti-PD-1 therapy in a patient suffering from melanoma. In one embodiment, the method comprises: assaying a tumor sample obtained from the patient for a measure of anti-PD-1 therapy sensitivity; selecting samples that exhibit a higher first enrichment similarity score (variation score) and/or a lower second enrichment similarity score (variation score) in (1) of the list of measures provided below, and/or at least one measure of sensitivity identified in (2) and/or (3) of the list below; and identifying a patient whose sample was selected herein as a candidate for anti-PD-1 therapy. This method can also be used to identify and select a melanoma whose somatic mutanome and/or transcriptome is responsive to anti-PD-1 therapy.

Representative examples of the measure of sensitivity include:

(1) gene set enrichment/variation analysis of the tumor sample for:
   (i) mesenchymal transition genes (AXL, ROR2, WNT5A, LOXL2, TWIST2, TAGLN, FAP and the genes listed in Supplementary Table S2C under the gene set "MAPKi induced EMT") and negative marker of mesenchymal transition (CDH1),
   (ii) immunosuppressive genes (IL10, VEGFA, VEGFC), and monocyte and macrophage chemotactic genes (CCL2, CCL7, CCL8 and CCL13),
   (iii) cell adhesion genes (listed in Table S2C under the gene sets "DTPP_Cell_Adhesion_UP", "PLX2D_Cell_Adhesion_UP", and genes in table S2A which are members of the gene ontology term cell adhesion: NRP1, CCL2, NPNT, EDIL3, MMRN1, DCHS1, ITGBL1, WISP1, COL7A1, COL6A3, COL6A2, COL6A1, COL12A1, ESAM, COL8A1, LOXL2, HAPLN1, EGFL6, COL13A1, SDK1, NID1, AJAP1, SSPN, CERCAM, EMILIN1, CTNNA2, TNFAIP6, CDH13, HAS1, LAMC3, ITGA5, ITGA8, FBLN5, FBLN7, ROR2, VCAN, JAM2,
   (iv) extracellularmembrane organization genes (genes listed in table S2A which are members of the gene ontology term extracellular matrix organization: LUM, ELN, OLFML2A, NID1, SERPINH1, COL5A2, EMILIN1, ITGA8, FBLN5, FOXF1, COL6A2, COL12A1, FOXC2),
   (v) wound healing genes (listed in Table S2C under the gene sets "EP_RESP_TO_WOUNDING_DN_IN_R", "PH_RESP_TO_WOUNDING_DN_IN_R", "MS_RESP_TO_WOUNDING_UP_IN_MAPKi_aPDL1_NR", "DTPP_RESP_TO_WOUNDING_UP", and genes in table S2A which are members of the gene ontology term response to wounding: F2RL2, F2RL3, CCL3, NRP1, CCL2, CCL8, MECOM, MMRN1, GAL, TIMP3, CCL7, IL10, PLAUR, IL17D, TNFAIP6, CCL13, PROCR, ITGA5, F3, FBLN5, SERPINE1, NFATC4, VCAN, ID3, NGF), and/or
(vi) angiogenesis genes (listed in Table S2C under the gene sets "MAPKi_INDUCED_ANGIOGENESIS", "EP_BLOOD_VESS_DEVEL_DN_IN_R", "PH_BLOOD_VESS_DEVEL_DN_IN_R", "MAPKR_BLOOD_VESS_DEVEL_UP", "DTPP_BLOOD_VESS_DEVEL_UP", "DTP_BLOOD_VESS_DEVEL_UP", and genes in table S2A which are members of the gene ontology term vasculature development: NRP1, FLT1, EFNB2, PRRX1, ENPEP, MMP2, GJA5, EDNRA, CDH13, VEGFC, ACE, ID1, FOXF1, VEGFA, FOXC2, ANGPT2);
wherein the gene set enrichment/variation analysis comprises determining a first enrichment similarity (variation) score indicative of statistical similarity between the level of mRNA expression, protein expression, and/or protein phosphorylation/acetylation of one or more (e.g., four, in one embodiment) of the genes listed in (i) to (vi) and a first reference set representative of tumors known to be sensitive to anti-PD-1 therapy, and determining a second enrichment similarity (variation) score indicative of statistical similarity between the level of mRNA expression, protein expression, and/or protein phosphorylation/acetylation of one or more of the genes listed in (i) to (vi) and a second reference set representative of tumors known to be unresponsive to anti-PD-1 therapy;
(2) non-synonymous mutations in BRCA2 and/or MTOR (mammalian target of rapamycin) genes, and/or loss of function indicated by mRNA expression loss and/or protein based assays of same; and
(3) increased mutational load in one or more cell adhesion-associated genes (genes in Table S2C under the gene sets "DTPP_Cell_Adhesion_UP", "PLX2D_Cell_Adhesion_UP", genes in table S2A which are members of the cell adhesion gene ontology terms: NRP1, CCL2, NPNT, EDIL3, MMRN1, DCHS1, ITGBL1, WISP1, COL7A1, COL6A3, COL6A2, COL6A1, COL12A1, ESAM, COL8A1, LOXL2, HAPLN1, EGFL6, COL13A1, SDK1, NID1, AJAP1, SSPN, CERCAM, EMILIN1, CTNNA2, TNFAIP6, CDH13, HAS1, LAMC3, ITGA5, ITGA8, FBLN5, FBLN7, ROR2, VCAN, JAM2).

In one embodiment, the assaying step comprises assaying at least two of the measures listed above. As used herein, "measures" refers to each type of measure listed as (1) to (3) above, including (1)(i) to (1)(vi), as well as to measures relating to each of the genes listed therein. In other embodiments, the assaying step comprises assaying at least 3, 4, 5, 6, 7, 8, 9, 10, 11, 12, 13, 14, 15, 20, or 25 of the measures listed above. In some embodiments, the at least two measures are assayed on the same tumor sample. In some embodiments, the gene set variation analysis comprises generating a score that represents normalized expression levels of at least four of the genes listed above. In other embodiments, the gene set variation analysis comprises generating a score that represents normalized expression levels of at least 5, 6, 7, 8, 9, 10, 12, 15, 20, 25, or more of the genes listed above.

The method can be performed prior to treatment with anti-PD-1 therapy, after treatment with anti-PD-1 therapy, and/or during disease progression or clinical relapse on anti-PD-1 therapy, as well as after suspension of anti-PD-1 therapy. In one embodiment, the melanoma is advanced metastatic melanoma. In some embodiments, the tumor sample is selected from tissue, bodily fluid, blood, tumor biopsy, spinal fluid, and needle aspirate.

Representative examples of the assaying include, but are not limited to, whole transcriptome sequencing, antibody based protein quantifications, mass spectrometry based protein quantification, targeted mRNA sequencing, and/or real-time RT-PCR. In some embodiments, the assaying comprises Sanger sequencing, targeted sequencing and/or whole exome/genome sequencing.

The method of the invention can further comprise treating the patient with anti-PD-1 therapy, optionally in conjunction with combinatorial therapy. In some embodiments, the anti-PD-1 therapy comprises treatment with an anti-PD-1 antibody (nivolumab/BMS-936558/MDX-1106, pembrolizumab/MK-3475, Pidilizumab), and/or an anti-PD-L1 antibody (BMS-986559, MPDL3280A, and MEDI4736).

The invention also provides a method of treating a patient suffering from melanoma. In one embodiment, the method comprises assaying a tumor sample obtained from the patient for a marker of sensitivity to anti-PD-1 therapy, and either administering anti-PD-1 therapy if the patient is positive for a marker of sensitivity to anti-PD-1 therapy, or administering alternative therapy if the patient is not positive for a marker of sensitivity to anti-PD-1 therapy. Representative examples of the alternative therapy include, but are not limited to, MARK targeted therapy (mutant BRAF inhibitors: Vemurafenib/PLX4032, Dabrafenib, Encorafenib/LGX818, MEK inhibitors: Trametinib/GSK1120212, Selumetinib/AZD6244, MEK162/Binimetinib, Cobimetinib/GDC0973, PD0325901, ERK inhibitors: SCH772984, VTX-11e, Pan RAF inhibitors: Sorafenib, CCT196969, CCT241161, PLX7904 and PLX8394); anti-CTLA-4 immunotherapy (Ipilimumab); anti-angiogenic therapy (Sorafenib, Sunitinib, Pazopanib, Everolimus, Bevacizumab, Ranibizumab, PLX3397); and any combination of the above with or without anti-PD-1 antibody (nivolumab/BMS-936558/MDX-1106, pembrolizumab/MK-3475, Pidilizumab) or anti-PD-L1 antibody (BMS-986559, MPDL3280A, and MEDI4736).

Also provided are kits comprising reagents for use in performing the methods described herein. Kits can further comprise one or more containers suitable for housing the reagents, and optionally, instructions for use.

BRIEF DESCRIPTION OF THE DRAWINGS

FIGS. 4A-4F. Genomic Features of Melanoma Tumors from Patients Treated with Anti-PD-1 Therapy, related to FIG. 1. (4A) The difference of tumor purities between the responding versus non-responding tumors with WES; p value, Mann Whitney test. (4B) The difference of WES coverages between the responding versus non-responding tumors; p value, Mann Whitney test. (4C) Correlations between the number of somatic nsSNVs and the number of predicted HLA class 1 (left) or class 2 (right) neoepitopes. Correlation, Pearson, p values, Student's t test. (4D) Recurrence of tetrapeptides (previously reported as enriched in responding pre-anti-CTLA-4 tumors) in non-responding and responding pre-anti-PD-1 tumors. (4E) Overall survival of TCGA melanoma patients whose tumors harbored high (top third) versus low (bottom third) mutational (somatic nsSNVs) loads; p value, log-rank test. (4F) Mutational loads (somatic nsSNVs) detected in melanoma with or without BRCA2 somatic nsSNVs in two datasets; p values, Mann Whitney test.

DETAILED DESCRIPTION

Figure 1A:
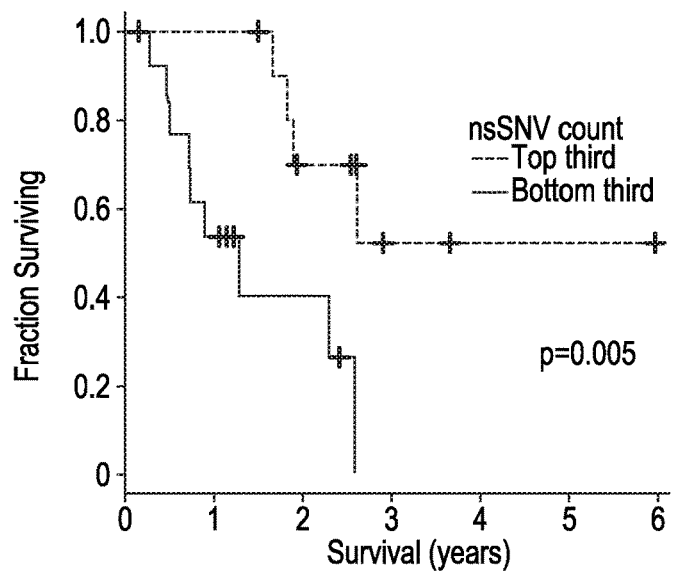
FIGS. 1A-1H, Mutational Correlates of Innate Sensitivity to Anti-PD-1 Therapy. (1A) Overall survival of anti-PD-1-treated patients whose melanoma tumors harbored high (top third) versus low (bottom third) mutational (somatic nsSNVs) loads. P values, log-rank test. (1B) Overall survival of anti-PD-1-treated melanoma patients whose pretreatment tumors responded (n=20) or did not respond (n=17). P value, log-rank test. (1C) Total number of nsSNVs detected in anti-PD-1 responding and non-responding melanoma tumors harboring high (above the respective group's median) or low (below the group median) mutational loads. P value, log-rank test. (1D) Overall survival of anti-PD-1-treated melanoma patients whose pretreatment tumors responded or did not respond and harboring high (above the group median) or low (below the group median) mutational loads. P value, log-rank test. (1E) Recurrent exomic alterations (nsSNVs and small insertion/deletions or INDELs) in pretreatment tumors of responding versus non-responding patients on anti-PD-1 therapy. Copy number alterations were annotated for the same gene as a reference. Top, mutations of melanoma signature genes. Middle, mutations recurrent in responding versus non-responding tumors (recurrence in 25% in one group and at most one occurrence in the opposite group, Fisher exact test, FDR-corrected P≤0.05 on enrichment against the background mutation frequency). Bottom, the total nsSNV load of each melanoma tumor. (1F) Schematics of impact of non-synonymous missense and nonsense mutations in the BRCA2 protein and its domains. (1G) Total number of nsSNVs detected in melanomas with or without BRCA2 non-synonymous mutations. P value, Mann Whitney test. (1H) Gene ontology (GO) enrichment of recurrently mutated genes in the tumors derived from responding patients. See also FIG. 4.

The present invention is based on the discovery of methods for predicting response patterns to anti-PD-1 therapy in metastatic melanoma. The discovery is based on analysis of somatic mutanomes and transcriptomes of pretreatment melanoma biopsies. This discovery enables the identification of a subset of melanoma patients who will respond to anti-PD-1 therapy, as well as guiding selection of a more appropriate treatment strategy for patients who are unlikely to respond to anti-PD-1 therapy. The invention thus provides for implementation of a more effective treatment strategy for melanoma patients.

Definitions

All scientific and technical terms used in this application have meanings commonly used in the art unless otherwise specified. As used in this application, the following words or phrases have the meanings specified.

As used herein, "tumor sample" or "biopsy" refers to a sample obtained from a cancer patient that contains tumor cells. Representative examples include a tumor biopsy, primary short term culture derived from the tumor; and a cell line derived from the tumor, which could be isolated from bodily fluid, blood, tumor biopsy, spinal fluid, and needle aspirate.

As used herein, "reference sample" refers to a fixed reference melanoma sample. One example of a reference sample is a resistant (positive) reference set that exhibits high expression of genes associated with innate anti-PD-1 resistance induced by MAPK inhibitor treatment. Another example of a reference sample is a sensitive (negative) reference set that does not exhibit high expression of such innate resistance genes.

As used herein, a "significant difference" means a difference that can be detected in a manner that is considered reliable by one skilled in the art, such as a statistically significant difference, or a difference that is of sufficient magnitude that, under the circumstances, can be detected with a reasonable level of reliability. In one example, an increase or decrease of 10% relative to a reference sample is a significant difference. In other examples, an increase or decrease of 20%, 30%, 40%, or 50% relative to the reference sample is considered a significant difference. In yet another example, an increase of two-fold relative to a reference sample is considered significant.

As used herein, "anti-PD-1 therapy" means treatment with an anti-PD-1 antibody (nivolumab/BMS-936558/MDX-1106, pembrolizumab/MK-3475, Pidilizumab), and/or an anti-PD-L1 antibody (BMS-986559, MPDL3280A, and MEDI4736).

As used herein, "combinatorial therapy" means MAPK targeted therapy, anti-CTLA-4 immunotherapy, anti-angiogenic therapy, in any combination, with or without anti-PD-1 antibody and/or anti-PD-L1 antibody treatment.

As used herein, "MAPK/ERK kinase (MEK)" refers to a mitogen-activated protein kinase also known as microtubule-associated protein kinase (MAPK) or extracellular signal-regulated kinase (ERK).

As used herein, "pharmaceutically acceptable carrier" or "excipient" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well-known conventional methods (see, for example, *Remington's Pharmaceutical Sciences,* 18th edition, A. Gennaro, ed., Mack Publishing Co., Easton, Pa., 1990).

As used herein, "a" or "an" means at least one, unless clearly indicated otherwise.

Transcriptomic Predictors of Response Patterns to Anti-PD-1 (aPD-1) Therapy

The concurrent upregulation of genes relate to several biological processes in the whole pretreatment tumor (melanoma) tissue as a predictive marker of resistance to aPD-1 therapy. These processes include tumor angiogenesis, tumor cell mesenchymal transition (alteration in the differentiation markers of the neural crest-melanocyte lineage) or stromal fibroblastic differentiation, tumor cell invasive switch, extracellular matrix reorganization, hypoxia, and response to wounding. Upregulation of these processes can be detected using transcriptomic profiles (e.g., as derived by RNASeq) of pretreatment tumors.

First, single-sample Gene Set Variation Analysis (GSVA) is performed on each tumor's RNASeq data, and enrichment scores of a collection of gene signatures (referred to as IPRIM or Innate anti-PD-1 Resistance, Induced by MAPKi signatures) for every pretreatment tumor is then derived. The invention is based on a transcriptomic measurement of genes in the IPRIM signatures in a pretreatment (aPD-1) melanoma biopsy compared to two fixed reference melanoma sample sets: one representing samples with high expression of IPRIM genes (positive or "resistant" reference set) and samples without IPRIM (negative or "sensitive" control set). The reference sets can be derived from public transcriptomic datasets such as TCGA or in-house dataset(s). To overcome difference in batches, platforms on which the measurement is made, we first normalize the IPRIM gene expressions to a reference gene set from the same sample: the reference can be the whole transcriptome (in case of using RNAseq or microarray) or a defined set of reference housekeeping genes such as TUBULIN or GAPDH (in case using multiplex qPCR or nCounter based analyses). The non-parametric rank statistics of the normalized IPRIM gene expressions in the measured sample are compared to the positive reference and negative control sets and those meeting a score cutoff of similarity to the positive reference set are defined to have IPRIM signature enrichment and are more likely to be non-responding to aPD-1 treatment. We first train the model using known samples with and without enrichment of the IPRIM signatures to optimize the classification performance of the model.

This invention's embodiments include, for example, immunohistochemistry (IHC), proteomics or methylomic based analytic/diagnostic platforms based on the detection of enrichment/up-expression IPRIM signature genes/proteins or activation of the pathways defined by the IPRIM gene signatures or its subset (i.e. angiogenesis, mesenchymal transition, tumor invasive switch, extracellular matrix reorganization, hypoxia, and response to wounding pathways).

Another embodiment of the invention provides a multivariate aPD-1 response prediction model that makes use of IPRIM signature enrichment and/or co-expression as a significant classifier variable. By significant, it means that such classifier performance would degrade by 50% or more when compared to a naïve predictor (e.g., overall mutational load of the sample) if the IPRIM-related variable(s) were removed from the model.

Another embodiment of a predictive assay based on the transcriptomic data comprises IHC-based scoring of protein expression levels based on genes that are differentially expressed by responding versus non-responding pretreatment tumors. A panel of such protein markers can be used to predict response versus non-response or likelihood of survival benefits.

Genomic Predictors of Response Patterns to Anti-PD-1 (aPD-1) Therapy

Genetic mutations (in particular loss-of-function mutations) in BRCA2 serve as one predictor of response to aPD-1 treatment. Mutations that are predicted to disrupt the BRCA2 protein function (by genomic and/or protein amino acid conservation metrics) are assessed using genomic sequencing methods such as whole genome, whole exome or targeted gene panel sequencing. The presence of BRCA2 mutation or other gene mutation(s) in the BRCA pathway (e.g on BRCA1, RAD51) maybe combined with data on overall mutational load of the pretreatment tumor sample to predict a patient's response to aPD-1 therapy. In particular, the presence of BRCA pathway mutations and high level of somatic mutations (defined by the top third mutation load range in a reference metastatic melanoma whole exome sequencing sample set) is predictive of response (tumor shrinkage) to or improved survival from aPD-1 therapy.

General enrichment of mutations in cell adhesion-related genes are also a predictive factor for response to aPD-1 treatment. Specifically, one can compare the mutational load and/or genes affected by mutation in a tumor sample and determine if the mutations disproportionately affect cell-adhesion related genes compared to melanomas with similar load of genetic mutation. This test can encompass whole genome, exome or panel-based genetic mutation profiling assays aimed at measuring gene mutations within the cell adhesion pathway compared to the whole genome/exome or compared to selected control genes with a known expected mutational load. The Gene Ontology term "Cell Adhesion" is used herein to define the genes deemed to be in the cell adhesion pathway.

Recurrent MTOR complex genes' loss-of-function mutations are also predictive of response to aPD-1 therapy. As such, an aPD-1 predictive model/assay which is based on genetic testing, transcriptomic and/or quantification of MTOR mRNA/protein expression levels and/or protein function readouts is provided in additional embodiments of the invention.

Methods for Identifying Sensitive or Unresponsive Melanoma

Methods described herein are performed using clinical samples or biopsies derived from patients or short-term culture derived from same. The methods guide the clinician in stratifying patients for sequential treatment strategies with alternative drug(s), combination therapy, or withdrawal and/or intermittent drug therapy. In one embodiment, the invention provides a method of selecting the somatic mutanomes and transcriptomes of melanoma biopsies. Following selection, the biopsies can be further tested in vitro for identification of an optimal therapeutic agent, and/or the corresponding subject from whom the biopsy was obtained, and/or their treating physician, can be notified of the selection.

In one embodiment, the invention provides a method of predicting or detecting sensitivity to therapeutic effects of anti-PD-1 therapy in a patient suffering from melanoma. In one embodiment, the method comprises: assaying a tumor sample obtained from the patient for a measure of anti-PD-1 therapy sensitivity; selecting samples that exhibit a higher first enrichment similarity (or variation) score and/or a lower second enrichment similarity (or variation) score in (1), and/or at least one measure of sensitivity identified in (2) and/or (3); and identifying a patient whose sample was selected herein as a candidate for anti-PD-1 therapy. Representative examples of the measure of sensitivity include:

(1) gene set enrichment/variation analysis of the tumor sample for:
  (a) mesenchymal transition genes (AXL, ROR2, WNT5A, LOXL2, TWIST2, TAGLN, FAP and the genes listed in Supplementary Table S2C under the gene set "MAPKi induced EMT") and negative marker of mesenchymal transition (CDH1),
  (b) immunosuppressive genes (IL10, VEGFA, VEGFC), and monocyte and macrophage chemotactic genes (CCL2, CCL7, CCL8 and CCL13),
  (c) cell adhesion genes (listed in Table S2C under the gene sets "DTPP_Cell_Adhesion_UP", "PLX2D_Cell_Adhesion_UP" and genes in table S2A which are members of the gene ontology term cell adhesion: NRP1, CCL2, NPNT, EDIL3, MMRN1, DCHS1, ITGBL1, WISP1, COL7A1, COL6A3, COL6A2, COL6A1, COL12A1, ESAM, COL8A1, LOXL2, HAPLN1, EGFL6, COL13A1, SDK1, NID1, AJAP1, SSPN, CERCAM, EMILIN1, CTNNA2, TNFAIP6, CDH13, HAS1, LAMC3, ITGA5, ITGA8, FBLN5, FBLN7, ROR2, VCAN, JAM2),
  (d) extracellular membrane organization genes (genes listed in table S2A which are members of the gene ontology term extracellular matrix organization: LUM, ELN, OLFML2A, NID1, SERPINH1, COL5A2, EMILIN1, ITGA8, FBLN5, FOXF1, COL6A2, COL12A1, FOXC2),
  (e) wound healing genes (listed in Table S2C under the gene sets "EP_RESP_TO_WOUNDING_DN_IN_R", "PH_RESP_TO_WOUNDING_DN_IN_R", "MS_RESP_TO_WOUNDING_UP_IN_MAPKi_aPDL1_NR", "DTPP_RESP_TO_WOUNDING_UP", and genes in table S2A which are members of the gene ontology term response to wounding: F2RL2, F2RL3, CCL3, NRP1, CCL2, CCL8, MECOM, MMRN1, GAL, TIMP3, CCL7, IL10, PLAUR, IL17D, TNFAIP6, CCL13, PROCR, ITGA5, F3, FBLN5, SERPINE1, NFATC4, VCAN, ID3, NGF), and/or
  (f) angiogenesis genes (listed in Table S2C under the gene sets "MAPKi_INDUCED_ANGIOGENESIS", "EP_BLOOD_VESS_DEVEL_DN_IN_R", "PH_BLOOD_VESS_DEVEL_DN_IN_R", "MAPKR_BLOOD_VESS_DEVEL_UP", "DTPP_BLOOD_VESS_DEVEL_UP", "DTP_BLOOD_VESS_DEVEL_UP", and genes in table S2A which are members of the gene ontology term vasculature development: NRP1, FLT1, EFNB2, PRRX1, ENPEP, MMP2, GJA5, EDNRA, CDH13, VEGFC, ACE, ID1, FOXF1, VEGFA, FOXC2, ANGPT2);

wherein the gene set enrichment/variation analysis comprises determining a first enrichment similarity (variation) score indicative of statistical similarity between the level of mRNA expression, protein expression, and/or protein phosphorylation/acetylation of one or more of the genes listed in (i) to (vi) and a first reference set representative of tumors known to be sensitive to anti-PD-1 therapy, and determining a second enrichment similarity (variation) score indicative of statistical similarity between the level of mRNA expression, protein expression, and/or protein phosphorylation/acetylation of one or more of the genes listed in (i) to (vi) and a second reference set representative of tumors known to be unresponsive to anti-PD-1 therapy;

(2) non-synonymous mutations in BRCA2 and/or MTOR (mammalian target of rapamycin) genes, and/or loss of function indicated by mRNA expression loss and/or protein based assays of same; and (3) increased mutational load in one or more cell adhesion-associated genes (genes in Table S2C under the gene sets "DTPP_Cell_Adhesion_UP", "PLX2D_Cell_Adhesion_UP", genes in table S2A which are members of the cell adhesion gene ontology term: NRP1, CCL2, NPNT, EDIL3, MMRN1, DCHS1, ITGBL1, WISP1, COL7A1, COL6A3, COL6A2, COL6A1, COL12A1, ESAM, COL8A1, LOXL2, HAPLN1, EGFL6, COL13A1, SDK1, NID1, AJAP1, SSPN, CERCAM, EMILIN1, CTNNA2, TNFAIP6, CDH13, HAS1, LAMC3, ITGA5, ITGA8, FBLN5, FBLN7, ROR2, VCAN, JAM2).

In one embodiment, the assaying step comprises assaying at least two of the measures listed above. In other embodiments, the assaying step comprises assaying at least 3, 4, 5, 6, 7, 8, 9, 10, 11, 12, 13, 14, 15, 20, or 25 of the measures listed above. In some embodiments, the at least two measures are assayed on the same tumor sample. In some embodiments, the gene set variation analysis comprises generating a score that represents normalized expression levels of at least four of the genes listed above. In other embodiments, the gene set variation analysis comprises generating a score that represents normalized expression levels of at least 5, 6, 7, 8, 9, 10, 12, 15, 20, 25, or more of the genes listed above.

In one embodiment, no more than 100 measures of those listed above under (1) through (3) are assayed in the patient's tumor sample. In another embodiment, no more than 50 measures are assayed in the patient's tumor sample. In one embodiment, up to 150 measures of those listed above are assays in the patient's tumor sample. In some embodiments, at least three measures from (1), (2), and/or (3) above are assayed. In other embodiments, at least five measures from (1), (2), and/or (3) above are assayed. In yet other embodiments, at least two measures from each of (1), (2), and (3) above are assayed. Likewise, in some embodiments, at least two or three measures from each of (a) through (f) of (1) above are assayed. In other embodiments, at least two or three measures from any combination of (a) through (f) of (1) above are assayed.

In one embodiment, assays to produce measures of enrichment similarity scores of a gene set comprise assaying at least two genes from (1) (a), i.e the mesenchymal transition genes category, combined with at least two genes from (1) (f), the category of angiogenesis genes. In another embodiment, assays to produce measures of enrichment similarity scores of a gene set comprise assaying at least two genes from (1) (a), i.e the mesenchymal transition genes category, combined with at least two genes from (1) (c), i.e the category of cell adhesion genes. Similar combinations from different categories of (1)(a) to (f) are contemplated.

The method can be performed prior to treatment with anti-PD-1 therapy, after treatment with anti-PD-1 therapy, and/or during disease progression or clinical relapse on anti-PD-1 therapy, as well as after suspension of anti-PD-1 therapy. In one embodiment, the melanoma is advanced metastatic melanoma. In some embodiments, the tumor sample is selected from tissue, bodily fluid, blood, tumor biopsy, spinal fluid, and needle aspirate.

Representative examples of the assaying include, but are not limited to, whole transcriptome sequencing, antibody based protein quantifications, mass spectrometry based protein quantification, targeted mRNA sequencing, and/or real-time RT-PCR. In some embodiments, the assaying comprises Sanger sequencing, targeted sequencing and/or whole exome/genome sequencing.

The method of the invention can further comprise treating the patient with anti-PD-1 therapy, optionally in conjunction with combinatorial therapy. In some embodiments, the anti-PD-1 therapy comprises treatment with an anti-PD-1 antibody (nivolumab/BMS-936558/MDX-1106, pembrolizumab/MK-3475, Pidilizumab), and/or an anti-PD-L1 antibody (BMS-986559, MPDL3280A, and MEDI4736).

The invention also provides a method of treating a patient suffering from melanoma. In one embodiment, the method comprises assaying a tumor sample obtained from the patient for a marker of sensitivity to anti-PD-1 therapy, and either administering anti-PD-1 therapy if the patient is positive for a marker of sensitivity to anti-PD-1 therapy, or administering alternative therapy if the patient is not positive for a marker of sensitivity to anti-PD-1 therapy. Representative examples of the alternative therapy include, but are not limited to, MAPK targeted therapy (mutant BRAF inhibitors: Vemurafenib/PLX4032, Dabrafenib, Encorafenib/LGX818, MEK inhibitors: Trametinib/GSK1120212, Selumetinib/AZD6244, MEK162/Binimetinib, Cobimetinib/GDC0973, PD0325901, ERK inhibitors: SCH772984, VTX-11e, Pan RAF inhibitors: Sorafenib, CCT196969, CCT241161, PLX7904 and PLX8394); anti-CTLA-4 immunotherapy (Ipilimumab); anti-angiogenic therapy (Sorafenib, Sunitinib, Pazopanib, Everolimus, Bevacizumab, Ranibizumab, PLX3397); and any combination of the above with or without anti-PD-1 antibody (nivolumab/BMS-936558/MDX-1106, pembrolizumab/MK-3475, Pidilizumab) or anti-PD-L1 antibody (BMS-986559, MPDL3280A, and MEDI4736).

Therapeutic and Prophylactic Methods

The invention further provides a method of treating a patient having melanoma, or who may be at risk of developing melanoma or a recurrence of melanoma. In a typical embodiment, the patient has advanced metastatic melanoma. Patients can be identified as candidates for treatment using the methods described herein. Patients are identified as candidates for treatment on the basis of exhibiting one or more indicators of sensitivity or resistance to anti-PD-1 therapy. The treatment protocol can be selected or modified on the basis of which indicators of sensitivity or resistance to anti-PD-1 therapy are exhibited by the individual patient.

The patient to be treated may have been initially treated with conventional melanoma therapy, or may be a patient about to begin melanoma therapy, as well as patients who have begun or have yet to begin other cancer treatments. Patients identified as candidates for treatment with one or more alternative therapies can be monitored so that the treatment plan is modified as needed to optimize efficacy.

Treatment includes prophylaxis and therapy. Prophylaxis or therapy can be accomplished by a single administration or direct injection, at a single time point or multiple time points to a single or multiple sites. Administration can also be nearly simultaneous to multiple sites. Patients or subjects include mammals, such as human, bovine, equine, canine, feline, porcine, and ovine animals. The subject is preferably a human. In a typical embodiment, treatment comprises administering to a subject a pharmaceutical composition of the invention.

A cancer may be diagnosed using criteria generally accepted in the art, including the presence of a malignant tumor. Pharmaceutical compositions may be administered either prior to or following surgical removal of primary tumors and/or treatment such as administration of radiotherapy or conventional chemotherapeutic drugs.

Administration and Dosage

The compositions are administered in any suitable manner, often with pharmaceutically acceptable carriers. Suitable methods of administering treatment in the context of the present invention to a subject are available, and, although more than one route can be used to administer a particular composition, a particular route can often provide a more immediate and more effective reaction than another route.

The dose administered to a patient, in the context of the present invention, should be sufficient to effect a beneficial therapeutic response in the patient over time, or to inhibit disease progression. Thus, the composition is administered to a subject in an amount sufficient to elicit an effective response and/or to alleviate, reduce, cure or at least partially arrest symptoms and/or complications from the disease. An amount adequate to accomplish this is defined as a "therapeutically effective dose."

Routes and frequency of administration of the therapeutic compositions disclosed herein, as well as dosage, will vary from individual to individual as well as with the selected drug, and may be readily established using standard techniques. In general, the pharmaceutical compositions may be administered, by injection (e.g., intracutaneous, intratumoral, intramuscular, intravenous or subcutaneous), intranasally (e.g., by aspiration) or orally. In one example, between 1 and 10 doses may be administered over a 52 week period. Preferably, 6 doses are administered, at intervals of 1 month, and booster treatments may be given periodically thereafter. Alternate protocols may be appropriate for individual patients. In one embodiment, 2 intradermal injections of the composition are administered 10 days apart.

A suitable dose is an amount of a compound that, when administered as described above, is capable of promoting an anti-tumor immune response, and is at least 10-50% above the basal (i.e., untreated) level. Such response can be monitored using conventional methods. In general, for pharmaceutical compositions, the amount of each drug present in a dose ranges from about 100 µg to 5 mg per kg of host, but those skilled in the art will appreciate that specific doses depend on the drug to be administered and are not necessarily limited to this general range. Likewise, suitable volumes for each administration will vary with the size of the patient.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients.

Kits

The invention provides kits comprising one or more reagents packaged for use in the methods described herein. The reagents can include, for example, oligonucleotide primers and/or probes, or antibodies that specifically recognize and bind relevant genes and expression products described herein, as well as other molecules designed for use in the methods described herein. The kit optionally includes one or more suitable containers containing reagents of the invention. The kit can optionally include a buffer.

EXAMPLES

The following examples are presented to illustrate the present invention and to assist one of ordinary skill in making and using the same. The examples are not intended in any way to otherwise limit the scope of the invention.

Example 1: Genomic and Transcirptomic Features of Resistance and Sensitivity to Anti-PD-1 Therapy in Metastatic Melanoma PD-1 immune checkpoint blockade provides significant clinical benefits for melanoma patients. This Example analyzes the somatic mutanomes and transcriptomes of pretreatment melanoma biopsies to identify factors that may influence innate sensitivity or resistance to anti-PD-1 therapy. The results demonstrate that, while overall high mutational loads associate with improved survival, tumors from responding patients are enriched for mutations in the DNA repair gene BRCA2, Innately resistant tumors display a transcriptional signature (referred to as the IPRES or Innate anti-PD-1 Resistance signature) indicating concurrent upexpression of genes involved in the regulation of mesenchymal transition, cell adhesion, ECM remodeling, angiogenesis and wound-healing. Notably, MAPK-targeted therapy (MAPKi) induces similar signatures in melanoma, suggesting that a non-genomic form of MAPKi resistance mediates cross-resistance to anti-PD-1 therapy. Validation of the IPRES in other independent tumor cohorts defines a transcriptomic subset across distinct types of advanced cancer. These findings suggest that attenuating the biological processes that underlie IPRES may improve anti-PD1 response in melanoma and other cancer types.

Experimental Procedures

Tumor Specimens and Profiling

All tissues in this study were obtained with the approval of Institutional Review Boards and patients' consents. All patients received either pembrolizumab or nivolumab as the anti-PD-1 therapy for their metastatic melanoma. Thirty-eight melanoma specimens (thirty-two pre-treatment tumors, two pretreatment tumor-derived cultures, three early on-treatment tumors without response, and one early on-treatment tumor with response) and their patient-matched normal tissues were analyzed by whole exome sequencing (WES). Among these thirty-eight samples with WES data, twenty-eight with sufficient RNA quality were also analyzed by RNASeq. This set include another RNASeq dataset derived from a second-site pre-treatment tumor biopsy from patient #27. However, this second-site, pre-treatment tumor-derived WES dataset was excluded in our aggregate mutation analysis to avoid double-counting two tumor exomes from the same patient.

Thirty eight tumor specimens and their respective normal tissues were subjected to whole exome sequencing (WES). WES was performed using pair-end sequencing with read length of 2×100 bps based on the Illumina HiSeq2000 platform. RNA from a subset of twenty eight tumors were pair-end sequenced with read length of 2×100 bps (Illumina HiSeq2000). We included two tumors from Pt27 for transcriptomic analyses but not for mutation and neoepitope analyses since the tumors may not share the same transcriptomic profile but they essentially contain the same set of non-synonymous somatic mutations.

Whole Exome Sequencing

We called single nucleotide variant (SNV) and small insertion-deletion (INDEL) as reported (Shi et al., 2014) using a stand-alone version of Oncotator (Ramos et al., 2015). Copy numbers were called using the intersection of the copy number calls derived from Sequenza (Favero et al., 2015) and VarScan2 (Koboldt et al., 2012). Tumor purities and ploidies were calculated based on the calls of Sequenza using WES data with default parameters. The impact of BRCA2 nsSNVs was visualized using the domain information in the INTERPRO protein domain database (Mitchell et al., 2015).

HLA Types and Neoepitopes

The 4-digit HLA class 1 and 2 types of each patient were called using ATHLATES (Liu et al., 2013) using the WES sequencing reads from the normal tissue. To ensure concordance, we manually compared ATHLATES' calls of the normal versus tumor samples and ascertained there was at least no two-digit HLA typing discrepancy between any normal-tumor pair. For each non-synonymous coding mutation from a tumor, we predicted its impact on the patient's HLA class I and II binding using the stand-alone version of the programs NetMHCpan v2.8 (Hoof et al., 2009; Nielsen et al., 2007) and NetMHCIIpan v3.0 (Karosiene et al., 2013), respectively. Specifically, for HLA class I binding prediction using netMHCpan v2.8, we tested all 9-11-mer peptides containing the mutated amino acids for binding to the patient's HLA-A, -B and -C. A peptide was defined as a neoepitope based on two criteria: i) predicted binding affinity ≤500 nM, and ii) rank percentage ≤2% (default cutoff). For HLA class II binding prediction using netMHCIIpan v3.0, we tested the 9-19-mers containing the mutated amino acids for binding to the patient-specific, ATHLATES-predicted DPA-DPB, DQA-DQB and DRA-DRB allele pairs. We also applied the same predicted binding affinity and rank percentage cutoff as we did for HLA class I to nominate the HLA class II-binding neoepitopes. Expressed non-synonymous mutations and neoepitopes were defined based on corresponding genes with normalized expression levels ≥1 (in FPKM). Statistical differences of nsSNV, HLA class I and II neoepitopes, WES coverages and tumor purities were computed using two-sided Mann-Whitney test.

Mutation Recurrence

To estimate the statistical significance of the recurrence of gene mutations in the responding or non-responding tumors, we used an independent batch of 469 melanomas' whole exome sequence datasets (Hodis et al., 2012; TCGA, 2015)

to estimate each gene's background mutation frequency. Significance was computed by Fisher exact test followed by FDR adjustment for multiple hypothesis testing. We listed genes that fulfilled the criteria: i) recurrence in at least 25% of the responder/non-responder, ii) occurrence of at most once in the opposite group and iii) Fisher exact test FDR adjusted p-value ≤0.05. These genes were illustrated in FIG. 1A and all genes that fulfilled i) and ii) and tested for multiple hypotheses were listed in the dataset available through NCBI GEO Accession No. GSE78220. The association between BRCA2 nsSNVs and overall nsSNV counts were tested using two-sided Mann-Whitney test and validated in independent WES datasets (Hodis et al., 2012; TCGA, 2015).

RNASeq and Gene Set Enrichment

Paired-end transcriptome reads were mapped to the UCSC hg19 reference genome using Tophat2 (Kim et al., 2013). Normalized expression levels of genes were expressed in FPKM values as generated by cuffquant and cuffnorm. The program were run with the option "--frag-bias-correct" and "--multi-read-correct" to improve sensitivity (Roberts et al., 2011). A gene was defined as differentially expressed between the responding and non-responding tumor groups when its median expression differed by at least two-fold between the groups with a nominal two-sided Mann-Whitney p-value ≤0.1 (Table 1). Applying multiple hypothesis correction of FDR p≤0.25 only yielded 3 differentially expressed genes; ALDH1L2 and MFAP2 in the non-responding and CDH1 (E-cadherin) in the responding group. As such, the genes meeting the uncorrected, nominal Mann-Whitney p-value ≤0.1 that were expressed higher either in the responding or non-responding group were separately analyzed for GO term enrichments using the online functional annotation tools DAVID (Huang et al., 2008). Enriched GO terms were selected from the GO biological process terms in DAVID's Fat database (Huang et al., 2009). GO terms which were highly overlapping, as defined by functional clustering in DAVID's website, were represented by the terms with the best FDR-adjusted p-values.

Figure 2A:
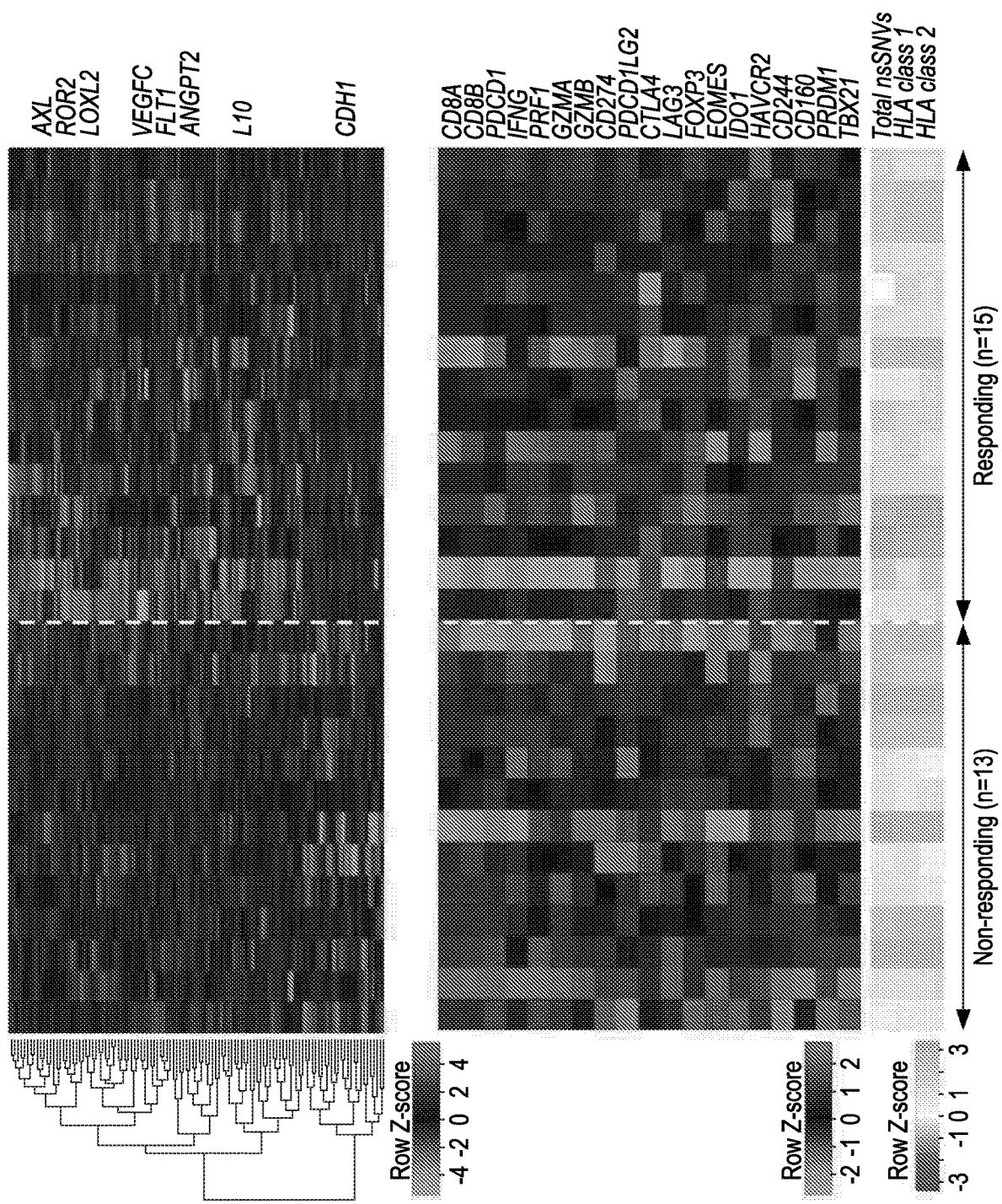
FIGS. 2A-2E. Transcriptomic Signatures of Innate Resistance to Anti-PD-1 Therapy. (2A) (Top) Heatmap showing differentially expressed genes in the pretreatment tumors derived from patients who responded versus who did not respond to anti-PD-1 treatment (gene expression with interquartile range (IQR)≥2; median fold-change (FC) difference≥2; Mann-Whitney P≤0.05). (Middle) mRNA expression levels of genes with hypothetical roles in modulating response patterns to anti-PD-1 therapy. (Bottom) Overall number of nsSNVs, HLA class 1 and 2 neoepitopes (predicted). (2B) mRNA levels of genes (which control tumor cell mesenchymal transition, tumor angiogenesis and macrophage and monocyte chemotaxis) that were differentially expressed between the responding versus non-responding pretreatment tumors. P values; Mann Whitney test. (2C) GO enrichment of genes that were expressed higher in the responding tumors. (2D) Heatmap showing the Gene Set Variance Analysis (GSVA) scores of gene signatures differentially enriched in the responding versus non-responding pre-anti-PD-1 tumors (absolute median GSVA score difference≤10%, FDR-corrected Welch t-test p≤0.25 or nominal Welch t-test p≤0.1). For comparison, enrichment scores of interferon signatures are also displayed. (2E) Overall survival of anti-PD-1-treated melanoma patients with presence (n=10) or absence (n=16) of co-enriched Innate Anti-PD-1 RESistance (IPRES) signatures. P value; log-rank test. See also Tables 1-3 and FIG. 5.
Figure 2B:
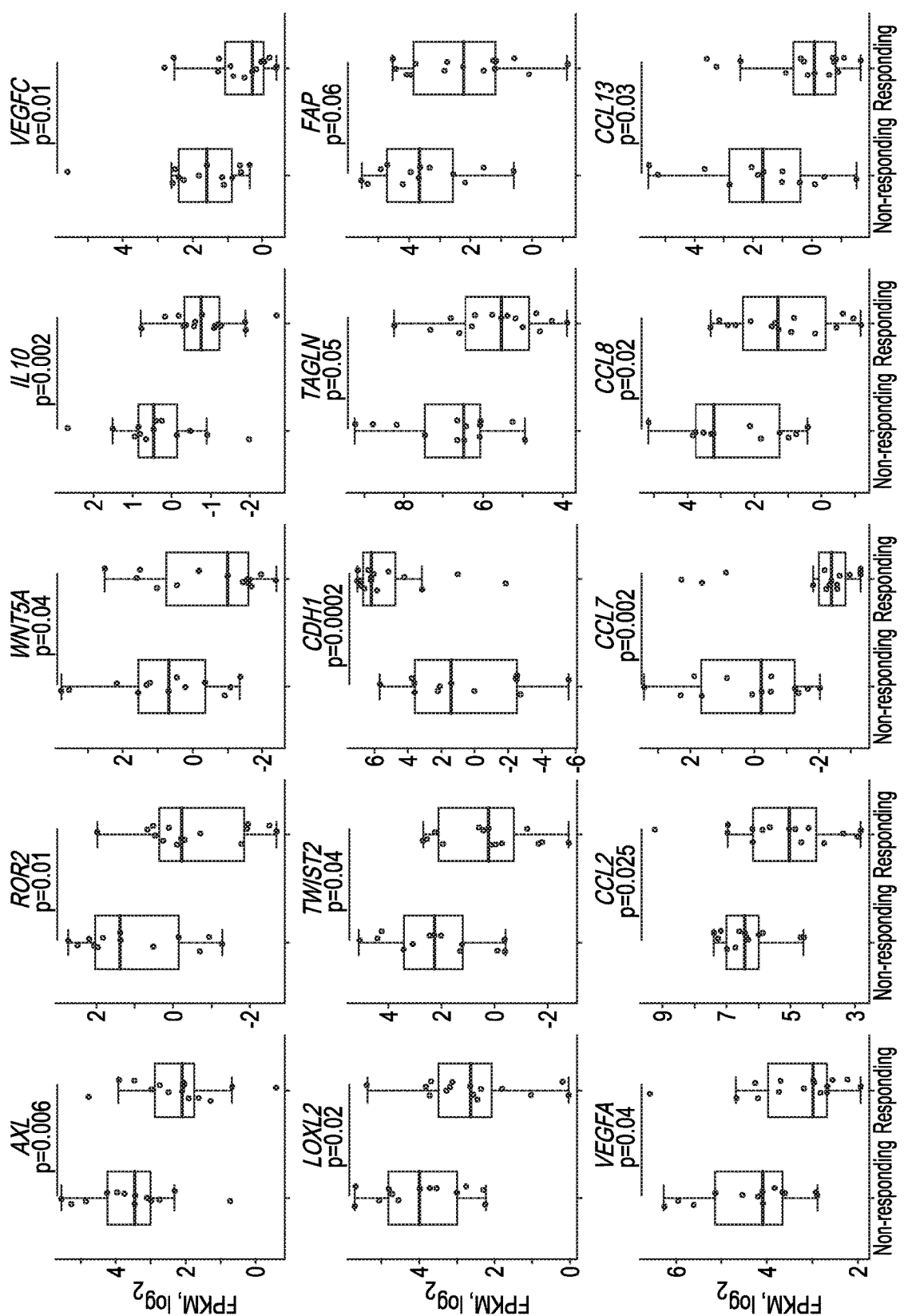
Figure 2C:
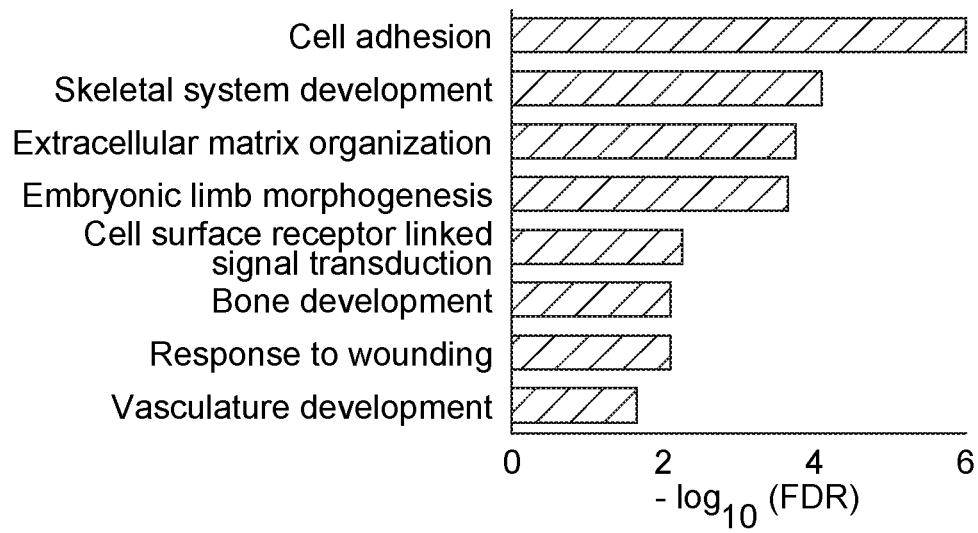
Figure 2E:
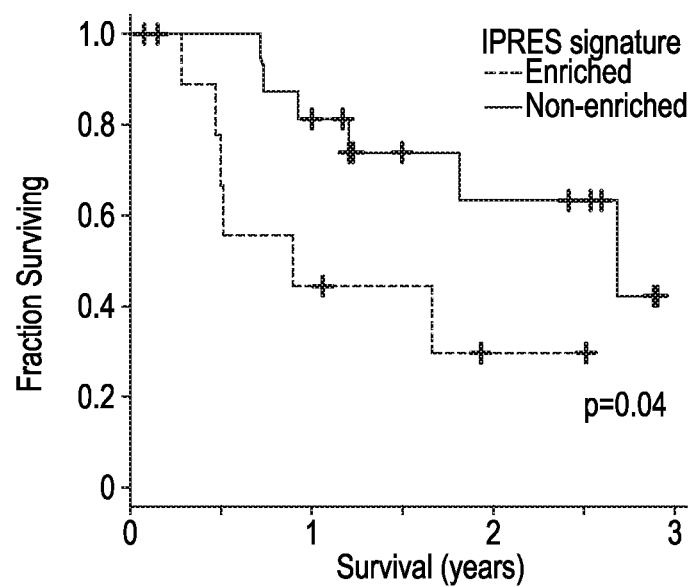
Figure 2D:
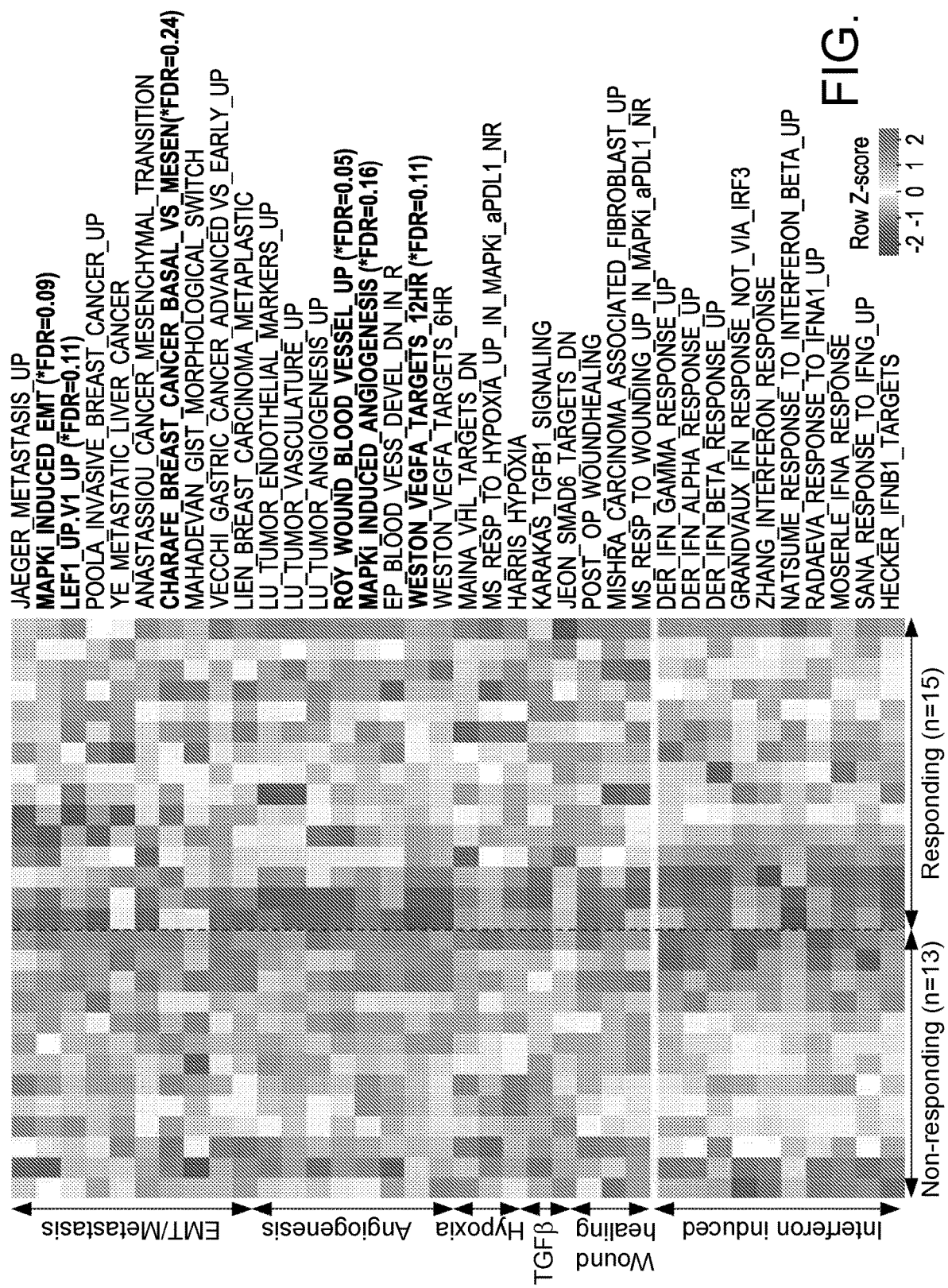
Figure 3A:
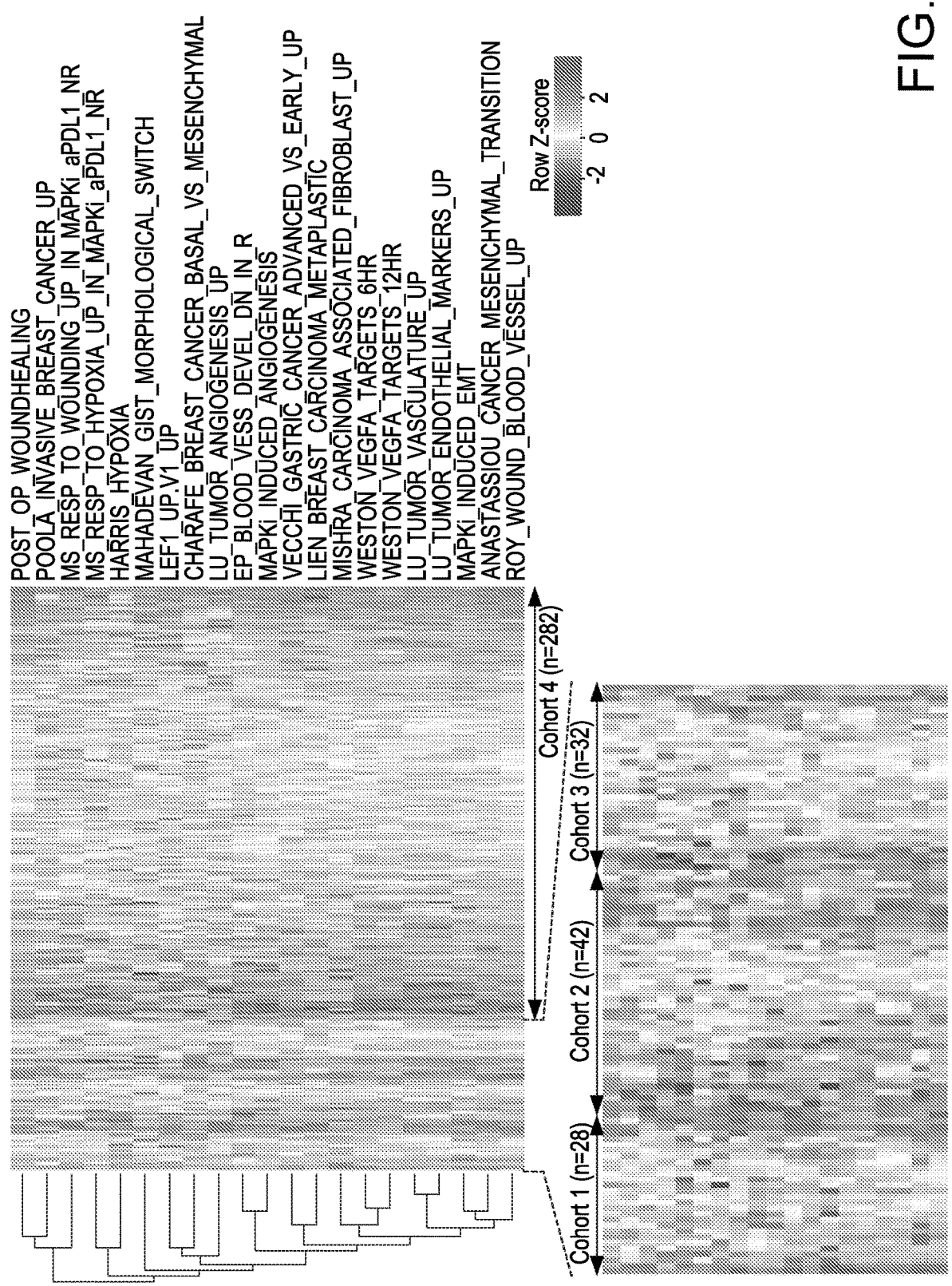
FIGS. 3A-3B. Co-enrichment of Innate Anti-PD-1 Resistance-associated Signatures Defines a Transcriptomic Subset in Melanoma and Multiple Cancers. (3A) Heatmap showing GSVA scores of IPRES signatures across four independent RNASeq data sets derived from metastatic melanoma. Cohort 1, pretreatment (anti-PD-1) tumors; cohort 2, pretreatment (anti-CTLA-4) tumors; cohort 3, pretreatment (MAPKi) tumors; cohort 4, TCGA cutaneous melanoma (metastatic only). (3B) Heatmap showing GSVA scores of IPRIM signatures across TCGA RNASeq data sets (metastatic melanoma or SKCM, lung adenocarcinoma or LUAD, colon adenocarcinoma or COAD, kidney clear cell carcinoma or KIRC, and pancreatic adenocarcinoma or PAAD). See also FIG. 6.

To calculate single-sample gene set enrichment, we used the GSVA program (Hanzelmann et al., 2013) to derive the absolute enrichment scores of previously experimentally validated gene signatures as follow: i) the C2 CGP (chemical and genetic perturbation sets), ii) the C6 and C7 subset of the Molecular Signature Database (Subramanian et al., 2005), iii) self-curated MAPK inhibitor-induced gene signatures using cell lines and patient-derived tumors (Song et al., 2015), iv) post-operation wound signature (Inkeles et al., 2015), and v) melanoma invasive/proliferative signatures (Hoek et al., 2008). To derive the GSVA score of each signature in each tumor sample, we computed from raw RNASeq read counts by HTSEQ COUNT program and then normalized them to $\log_2$ CPM values using EdgeR (McCarthy et al., 2012). We removed batch effects using the edgeR function RemoveBatchEffect when we combined RNAseq data from multiple experiments (FIG. 3A). The normalized $\log_2$ CPM values were then passed on as input for GSVA in the RNASeq mode. Differentially enriched core gene sets between the responding and non-responding tumor groups were defined by GSVA score differences of ≥10% and FDR-corrected, two-sided Welch T-test p-value ≤0.25 (we used T-test because the GSVA scores were normally distributed around 0). Two gene sets, INGRAM_SHH_TARGETS_DN and WONG_ENDMETRIUM_CANCER_DN, were not included in the core set because they did not specifically point to a cellular process and/or relate to the other six gene sets in the core set (Table 2, top 8). We also collected gene sets that met the GSVA score differences of ≥10% and nominal Welch T-test p-value ≤0.1 (Table 2) and included those which were concordantly enriched and functionally related to the core gene sets to make up the full list of IPRES signatures (FIG. 2D).

To compare co-enrichment of IPRES signatures across multiple melanoma cohorts, we combined and batch-corrected the $\log_2$ CPM values of four melanoma transcriptome cohorts: i) our current pre-anti-PD-1 tumors (n=28), ii) pre-anti-CTLA-4 tumors (n=42), iii) pre-MAPKi tumors (n=32) and iv) the metastatic subset of TCGA melanoma (n=282). We row-normalized the GSVA scores of each gene set in the IPRES signature across the samples from the four cohorts. For this comparative study, we excluded the gene sets "JAEGER_METASTASIS_UP," "YE_METASTATIC_LIVER_CANCER," "KARAKAS_TGFB1_SIGNALING," and "JEON_SMAD6_TARGETS_DN" from the IPRES set because they showed weaker co-enrichment with rest of the gene sets (see FIG. 2D upper panel). The IPRES (enrichment) score was defined as the average Z-score across all gene sets in the IPRES signature, and we applied an average Z-score of 0.35 as the cutoff for IPRES signature enrichment in a tumor sample. This resulted in IPRES co-enrichment in 9 non-responding tumors and 1 responding tumor in our anti-PD-1 cohort (this cutoff was chosen because it provided the largest average Z-score separation between the samples with and without IPRES co-enrichment). Since the average Z-score was not comparable between different cohorts, we used the 90th highest IPRES score in the TCGA metastatic melanoma cohort as the IPRES score cutoff (since there were 90 of 282 tumors showing IPRES co-enrichment in this TCGA metastatic cohort; FIG. 3A) for analyses performed to yield FIGS. 3B and S3. This allowed for a non-parametric comparison across multiple TCGA datasets at the IPRES co-enrichment level established in our anti-PD-1 cohort.

Source Data

Analysis of differential non-synonymous mutational hits in responders versus non-responders to ipilimumab was based on the mutation calls as reported (Van Allen et al., 2015). We curated published CD8 T cell exhaustion genes (Wherry, 2011) to minimize those likely to be expressed by melanoma cells by excluding genes whose maximum $\log_2$ FPKM was 1 in an in-house melanoma cell line-derived RNASeq database (n=26 cell lines). This resulted in the inclusion of genes for surface receptors PDCD1 (PD-1), LAG3, HAVCR2 (Tim-3), CD160, and CD244 as well as transcription factors EOMES, PRDM1 (Blimp-1) and TBX21 (T-bet). We assessed co-enrichment of IPRES content signatures in the i) anti-CTLA-4 pretreatment cohort (Van Allen et al., 2015), ii) MAPKi pretreatment cohort (Hugo et al., 2015; Song et al., 2015), iii) TCGA melanoma (metastatic and primary subsets separately analyzed) (TCGA, 2015); iv) TCGA pancreatic ductal adenocarcinoma (TCGA, 2016), v) TCGA lung adenocarcinoma (TCGA, 2014), and vi) TCGA colorectal adenocarcinoma (TCGA, 2012); and vii) TCGA kidney clear cell carcinoma (TCGA, 2013).

Results and Discussion

High Mutational Load does not Associate with Tumor Response but Correlates with Improved Patient Survival We analyzed the whole exome sequences (WES) of 38 pretreatment (pembrolizumab, nivolumab) melanoma tumors (responding; n=21; non-responding; n=17; total 34 of 38 pretreatment; 4 of 38 early on-treatment; 14 of 38 patients with prior MAPKi treatment) and patient-matched normal tissues for germline references. Responding pretreatment tumors were derived from patients who went on to have complete or partial responses or stable disease control (with mixed responses excluded) in response to anti-PD-1 therapy. Non-responding tumors were derived from patients who had progressive disease. These response patterns were based on irRECIST (Hops et al., 2015; Wolchok et al., 2009). We also analyzed the transcriptomes through RNASeq of responding (n=15) and non-responding (n=13) pretreatment tumors (total 27 of 28 pretreatment; 1 of 28 early on-treatment) with available high-quality RNA. WES achieved a median of 140× coverage in both tumor and normal tissues. We detected a median of 489 non-synonymous somatic mutations in the 38 tumors (range 73 to 3,985, which is similar to that in a different set of melanoma tissues (Van Allen et al., 2015)).

Figure 4D:
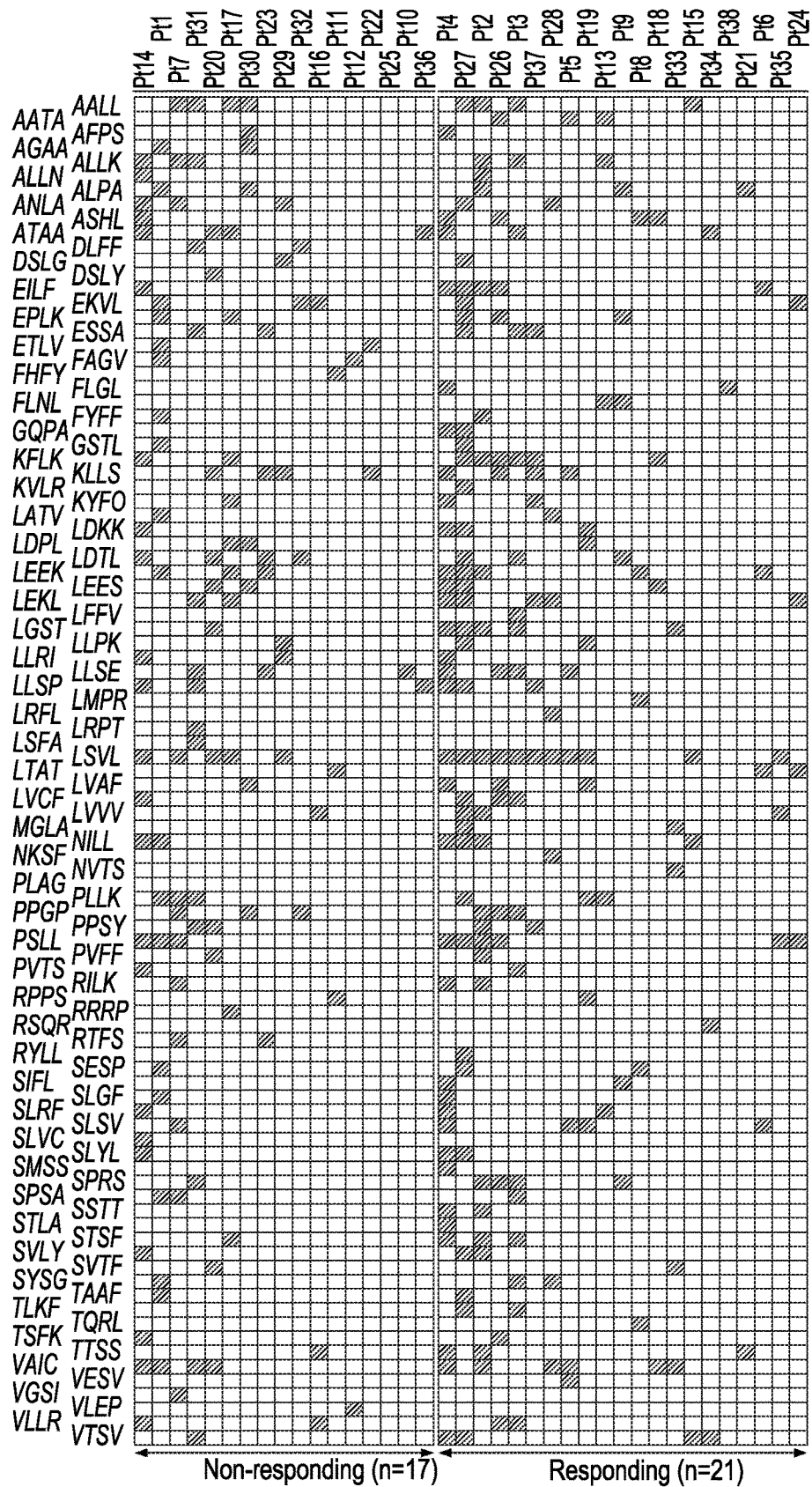
Figure 4F:
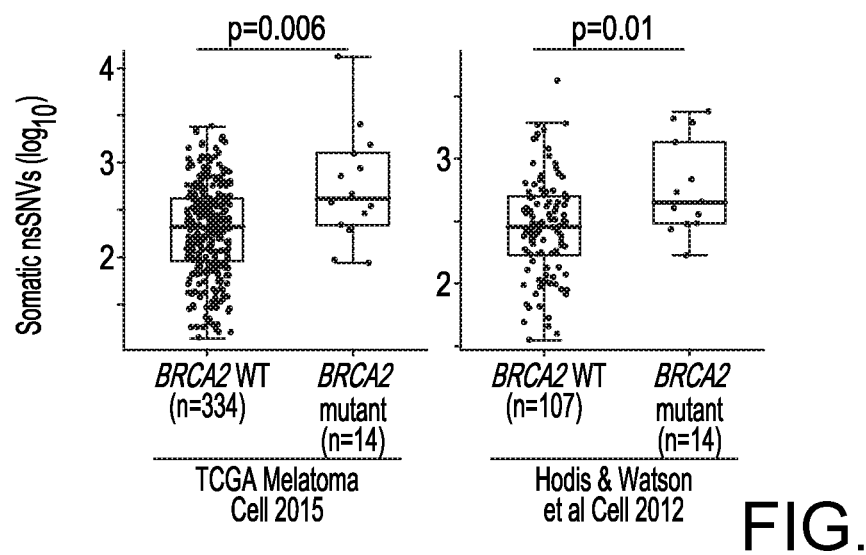
Figure 5A:
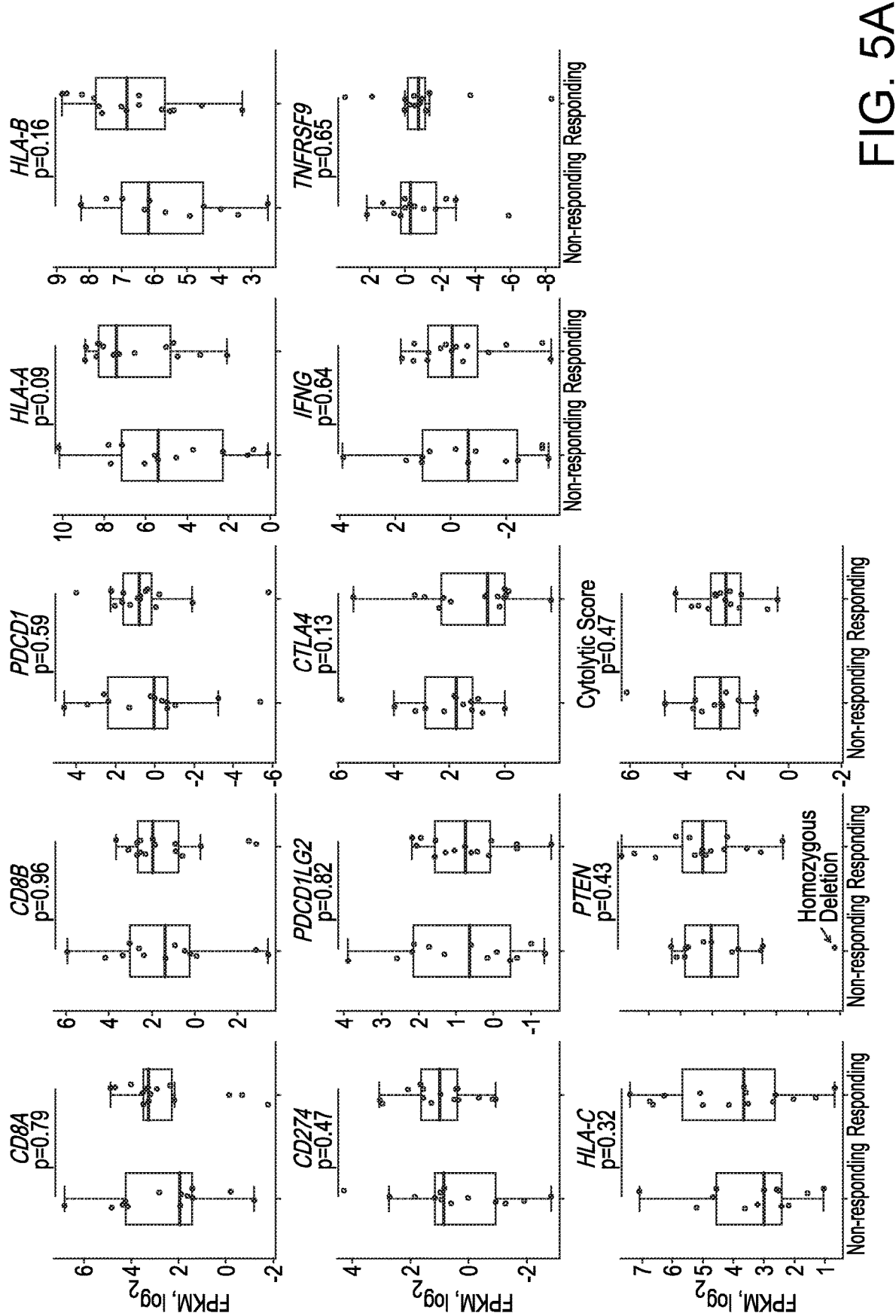
FIGS. 5A-5B. Gene or Signature Expression Patterns in Pretreatment Melanoma Tumors on Anti-PD-1 or Anti-CTLA-4 Therapies, related to FIG. 2. (5A) mRNA levels of genes (CD8 T cell markers, effectors, cytolytic scores; immune checkpoints, MHC class 1, and PTEN) between the responding versus nonresponding pretreatment tumors; p values, Mann Whitney test. (5B) Heatmap showing GSVA scores of IPRES signatures across responding (n=14) versus non-responding (n=27) pre-anti-CTLA-4 tumors.
Figure 5B:
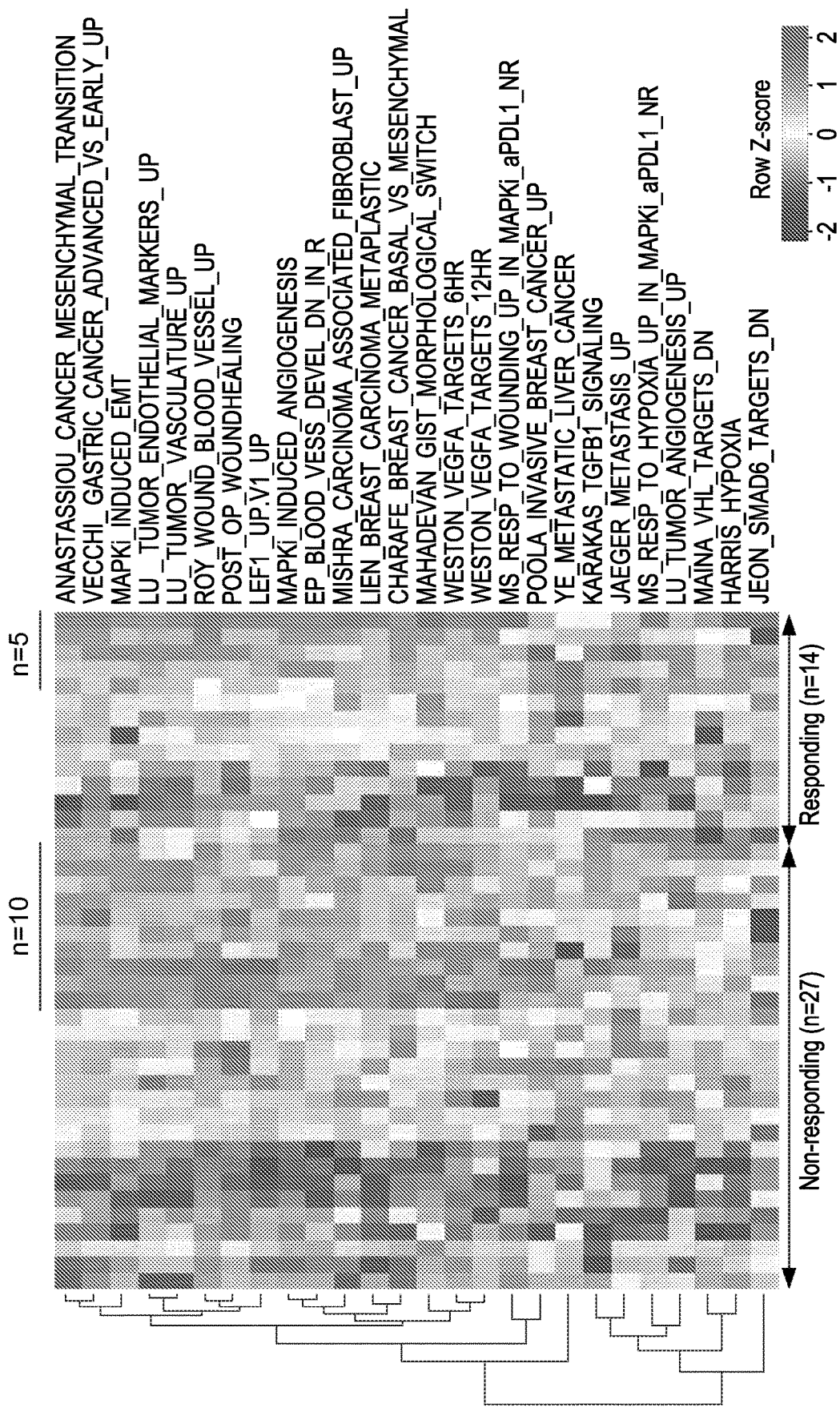
Figure 6:
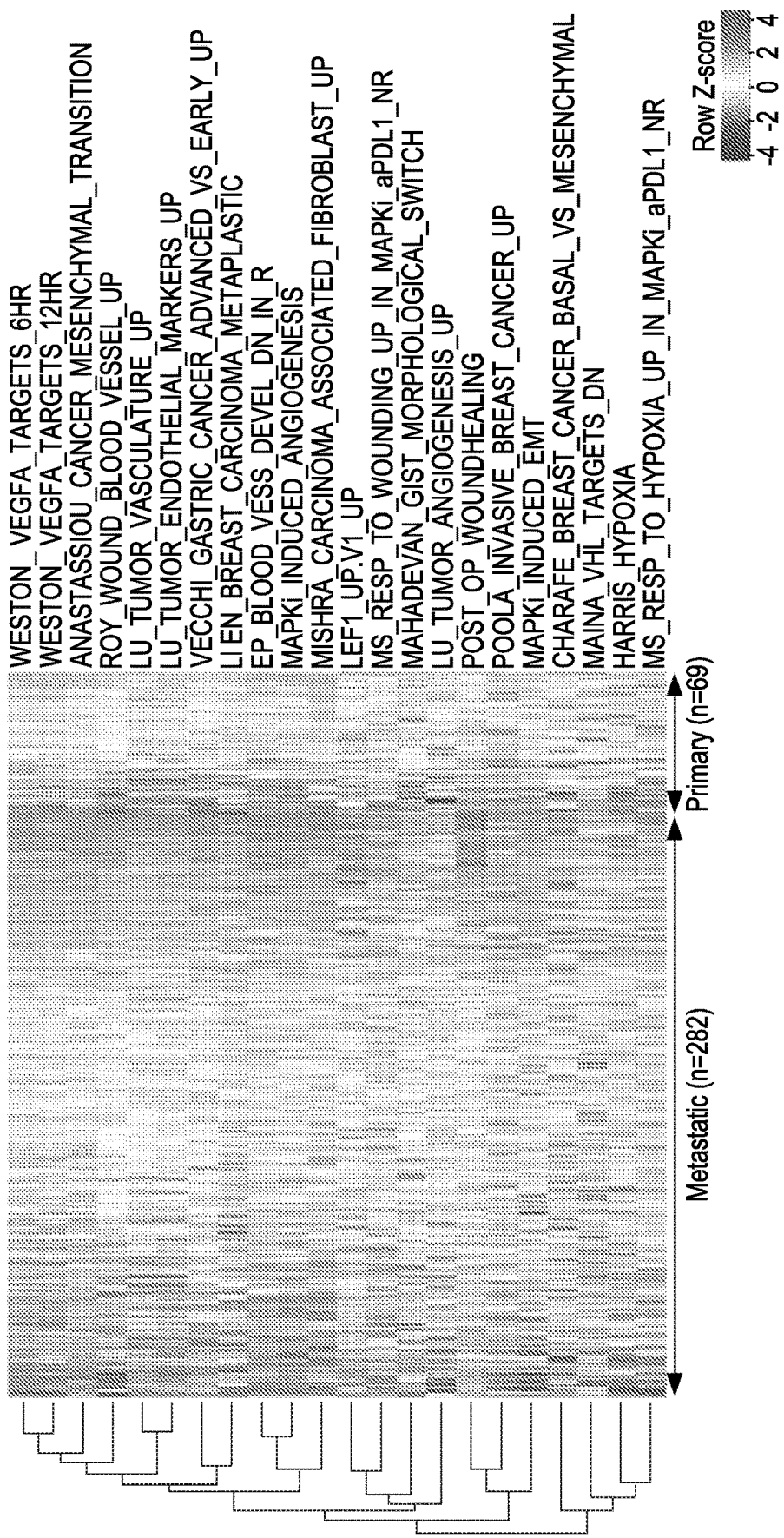
FIG. 6. Co-enrichment of IPRES Signatures in Metastatic versus Primary Cutaneous Melanoma, related to FIG. 3. Heatmap showing GSVA scores of IPRES signatures across TCGA primary and metastatic melanoma tumors.

We found that responding pretreatment tumors on anti-PD-1 therapy harbored harbors more non-synonymous single nucleotide variants (nsSNVs) compared to the non-responding tumors, albeit the statistical significance cutoff was not met (median nsSNVs responding=495 and non-responding=281, P=0.30, Mann-Whitney). Increased predicted HLA class I and class II neoepitope loads were also detected in the responding pretreatment tumors, although these differences were not statistically significant either (median HLA class I neoepitopes responding=231 and non-responding=156, P=0.41; median HLA class II neoepitopes responding=130 and non-responding=95, P=0.36, Mann-Whitney), Even when we considered only expressed nsSNV and neoepitope loads, the statistical significance of the differences between the responding versus non-responding tumors was not augmented. The comparison of these two groups of tumors was not likely biased by small differences in mean tumor purities or depth of sequencing (FIG. 4 and FIG. 5). The numbers of predicted HLA class I and II neoepitopes were strongly correlated with the number of nsSNVs (FIG. 6). We did not identify any recurrent predicted neoepitope or experimentally validated neoantigens. Previous work analyzing melanoma tumors sampled prior to anti-CTLA-4 antibody therapy had associated responses with a tetrapeptide signature (Snyder et al., 2014). However, we did not observed enrichment of this peptide motif in the pretreatment tumors that responded to anti-PD-1 therapy (FIG. 4D). Likewise, analysis of an independent cohort of 110 melanoma tumors pre-anti-CTLA-4 therapy also did not yield enrichment of this tetrapeptide motif among responding tumors (Van Allen et al., 2015).

Figure 1B:
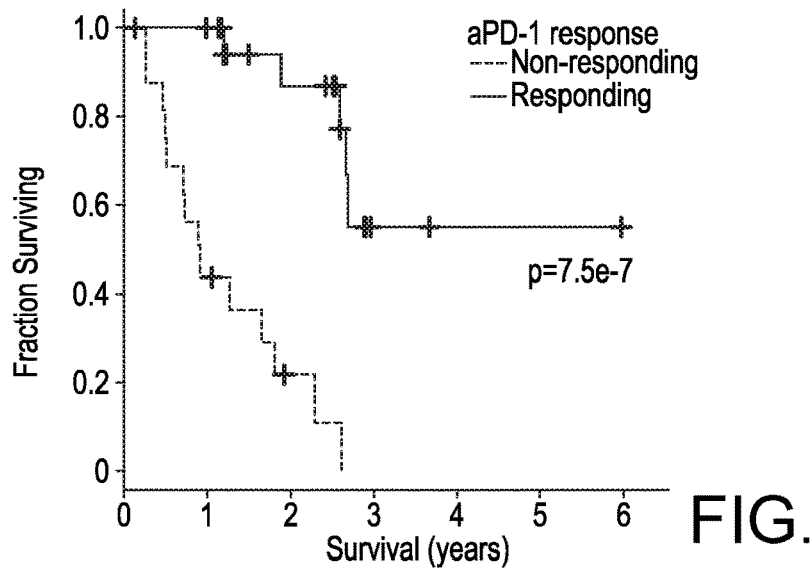
Figure 1C:
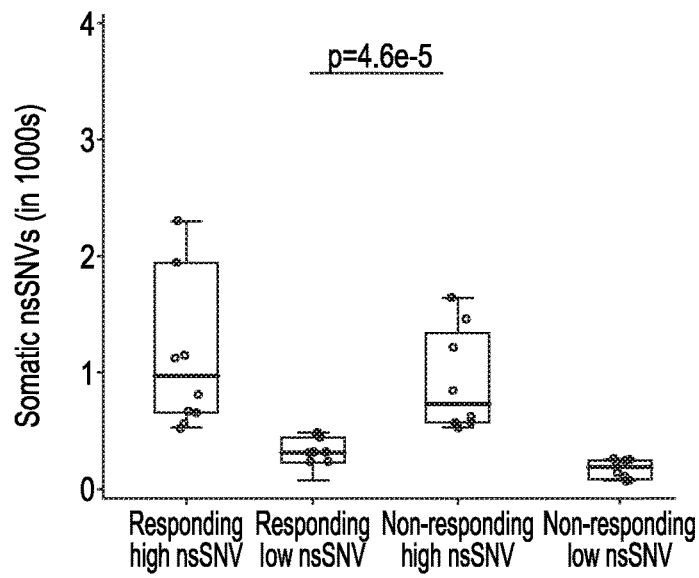
Figure 1D:
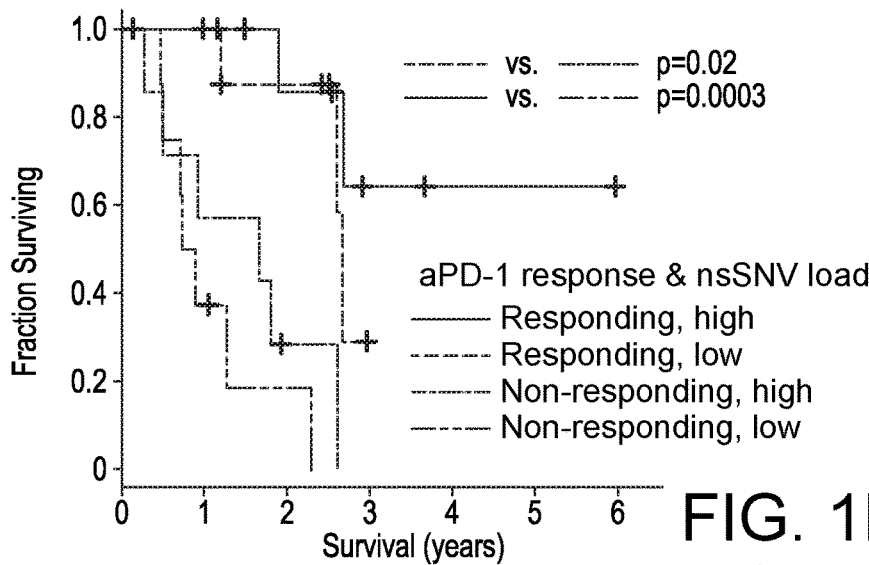

In addition to examining the relationship between non-synonymous somatic mutational loads in pretreatment tumors and anti-tumor responses (and lack thereof) elicited by anti-PD-1 antibodies, we also examined their relative potential influences on clinical benefits of anti-PD-1 immunotherapy as reflected by patient survival. Notably, a mutational load in the top third (compared to the bottom third) was significantly associated with improved survival (FIG. 1A). We also observed a trend toward higher mutational load being associated with better survival among melanoma patients not treated with anti-PD-1 antibodies (TCGA, 2015), although this association did not reach statistical significance (FIG. 4E), suggesting that the prognostic power of a high mutational load is augmented in the setting of anti-PD-1 therapy. As expected, a positive association between objective tumor responses and survival was highly statistically significant (FIG. 1B). However, when we divided each non-responding and responding tumor group into sub-groups with low or high mutational loads (i.e., below or above the median total somatic nsSNVs of each response group) (FIG. 1C), patients with responding tumors of low mutation loads significantly outlived patients with non-responding tumors of high mutation loads (FIG. 1D). This is despite the fact that mutational loads of these two groups were significantly different, with no overlap across the two distributions (FIG. 1C). Hence, factors beyond the mutational load also influence shorter-term tumor response patterns and longer-term patient survival.

Enrichment for BRCA2 Mutations in Anti-PD-1 Responsive Melanoma

Figure 1F:
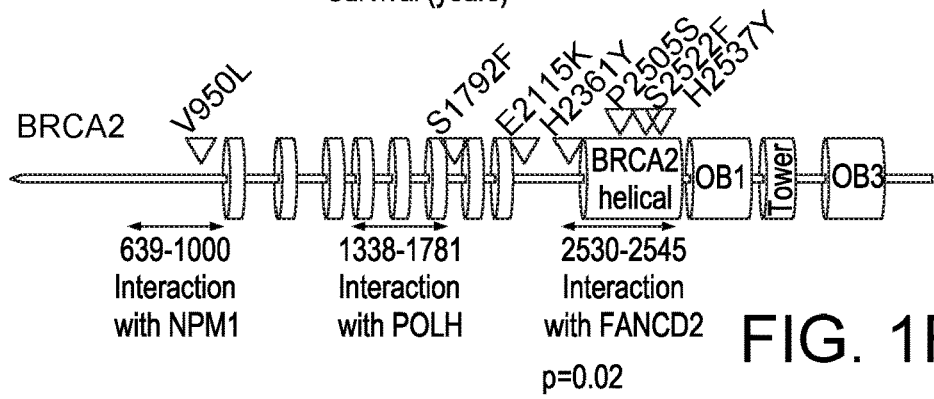
Figure 1G:
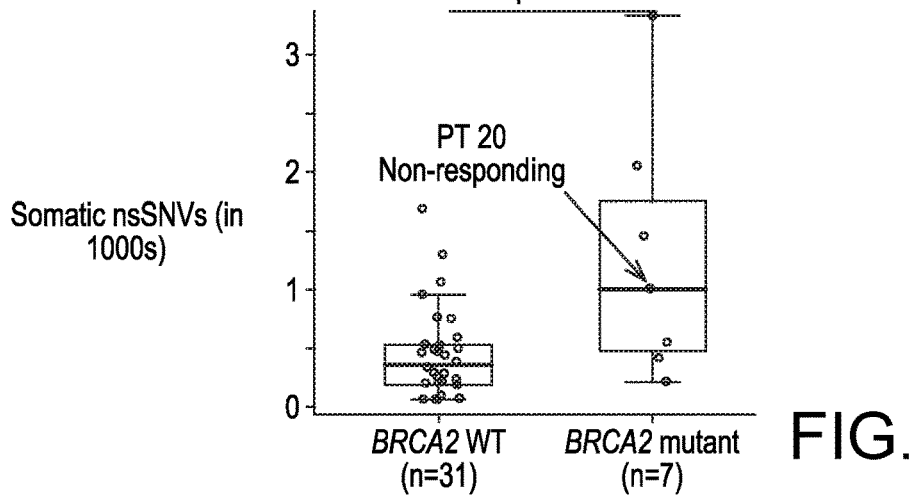
Figure 1H:
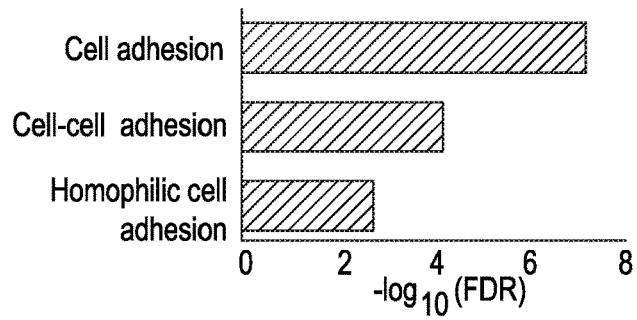
Figure 1E:
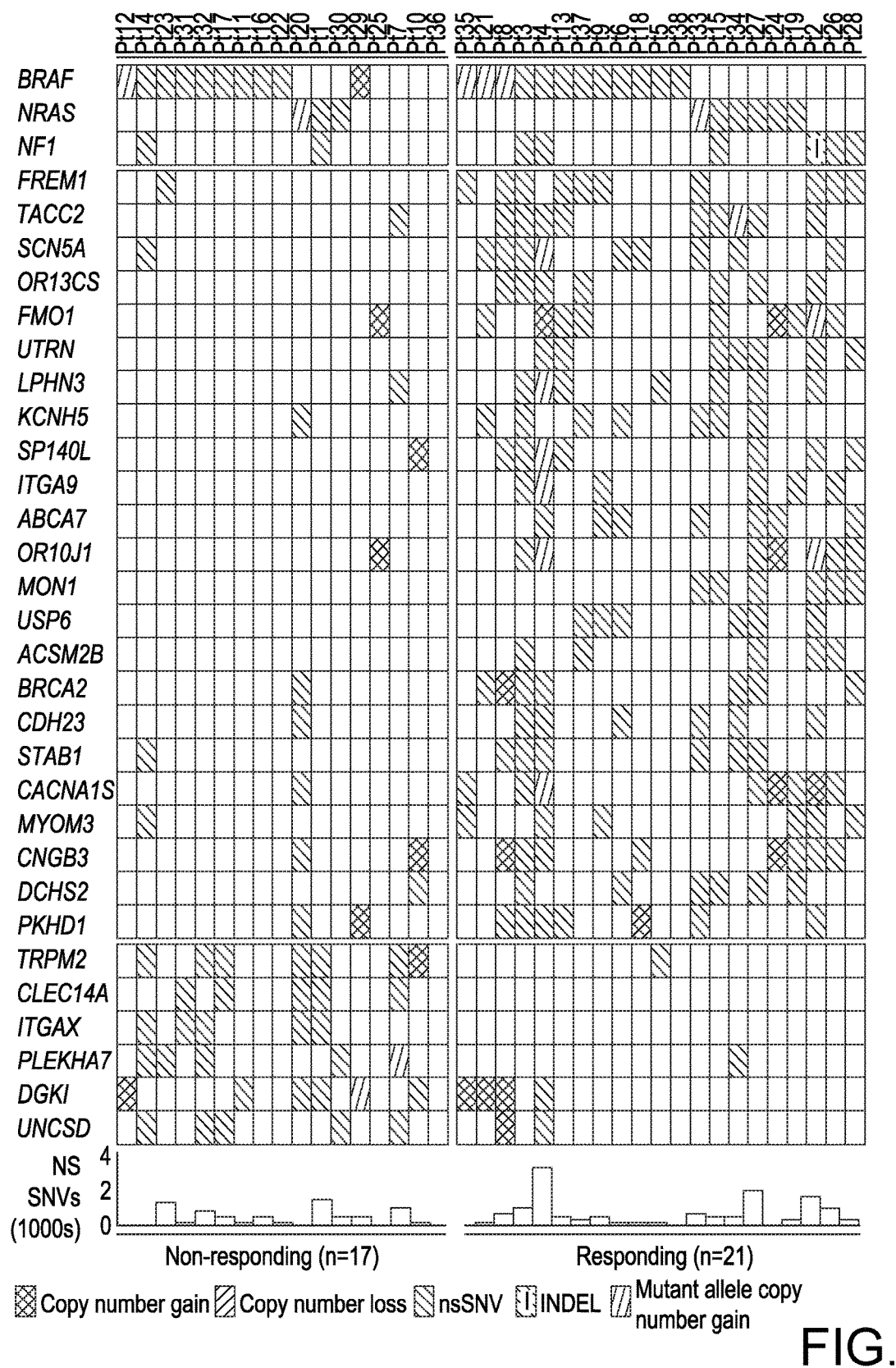

We then sought to identify mutations (nsSNVs and small insertion-and-deletions or INDELs) that (i) were recurrently and selectively associated with either responding or non-responding tumors (recurrence ≥25% in one group and at most one hit in the other group) and (ii) occurred in genes at rates higher than background rates (Fisher exact test, FDR-corrected p≤0.05) (FIG. 1E). The background mutation rate of each gene was calculated from the WES data of 469 melanoma tumors (Hodis et al., 2012; TCGA, 2015). Analysis of copy number variation (CNVs) did not identify any recurrent alterations exclusive to either group. BRCA2 harbored nsSNVs in six of 21 responding tumors (28%) but only one of 17 non-responding tumors (6%) (FIG. 1E). With a background mutational rate estimated at 6% (28 of 469 melanoma tumors), BRCA2 was significantly more frequently mutated in the responding tumors than expected (Fisher P=0.002, odds ratio=6.2). The pattern of mutations in disparate BRCA2 protein domains suggested loss-of-function mutations (FIG. 1F): one in the N-terminal NPM1-interacting region; one in the POLH-interacting domain; and four in the helical domain critical for FANCD2 interaction. Intriguingly, the somatic mutational load of the tumors with BRCA2 nsSNVs was significantly higher than those with wild type BRCA2 in this cohort of tumors (FIG. 1G) as well as two additional cohorts of melanoma tumors (FIG. 4F). Thus, BRCA2 LOF mutations, which are expected to produce defects in homologous recombination and double-stranded DNA break repair (Holloman, 2011), may produce specific mutational signatures or unknown effects (e.g., induction of cell death) which contribute to anti-PD-1 responsiveness.

Co-Enriched Transcriptomic Signatures in a Major Subset of Anti-PD-1 Resistant Melanoma We then addressed whether transcriptomic features would differentiate between responding (n=15) versus non-responding (n=13) tumors sampled prior to anti-PD-1 therapy (total 27 of 28 pretreatment tumors and 1 of 28 early on-treatment). We compared the transcriptomes of the two tumor groups using two approaches: (i) analysis of differentially expressed genes (DEGs) (FIG. 2A top and FIG. 2B) across the two aggregate groups (Table 1) coupled with GO term enrichment analysis of DEGs (FIG. 2C) and (ii) differential signature enrichment based on single-sample Gene Set Variance Analysis or GSVA scores using publicly available (C2 chemical and genetic perturbation C6 oncogenic, and C7 immunologic subsets of the Molecular Signature Database, Broad Institute) and self-curated (see below), perturbation-induced gene signatures (Table 2; FIG. 2D).

From analysis of DEGs (cutoff, two-fold difference between the absolute medians of normalized expressions in the two groups; nominal Mann-Whitney p≤0.1), we made observations suggesting that mesenchymal and inflammatory tumor phenotypes may be associated with innate anti-PD-1 resistance. First, 693 genes were differentially expressed between the responding versus non-responding pretreatment tumors, and the transcriptomes of non-responding tumors were dominated by relative gene up-expression events compared with the transcriptomes of responding tumors (Table 1; FIG. 2A top, showing only genes whose differential expression met nominal Mann-Whitney p≤0.05). Second, DEGs that were expressed higher in non-responding pretreatment tumors included mesenchymal transition genes (AXL, ROR2, WNT5A, LOXL2, TWIST2, TAGLN, FAP), immunosuppressive genes (IL10, VEGFA, VEGFC), and monocyte and macrophage chemotactic genes (CCL2, CCL7, CCL8 and CCL13) (FIGS. 2A and 2B). In addition to mesenchymal genes, genes associated with wound healing and angiogenesis, which are considered T cell-suppressive (Motz and Coukos, 2011; Schafer and Werner, 2008; Voron et al., 2014), were expressed higher among non-responding relative to responding pretreatment tumors. Interestingly, a recent study using a mouse melanoma model showed that VEGFA and CCL2 expression was associated with innate anti-PD-1 resistance (Peng et al., 2015). CDH1, which is typically down-expressed by mesenchymal cancer cells, was also down-expressed by non-responding (versus responding) pretreatment tumors. Third, genes with putative roles in modulating immune checkpoint sensitivity were not differentially expressed between responding versus non-responding tumor groups (FIG. 2A bottom; Figure S2). GZMA, PRF1 (CD8 T cell cytolytic score), PDCD1LG2 (PD-L2) and CTLA4 were expressed higher in the pretreatment melanoma tumors of patients who derived benefit from CTLA-4 antibodies (Van Allen et al., 2015). However, these genes, along with other T cell-related genes such as CD8A/B, PD-L1, LAG3 (T cell checkpoint genes) and IFNG, did not present higher expression in anti-PD-1-responsive tumors (FIG. 2A bottom; Figure S2A), Similarly, we did not observe higher enrichment of multiple interferon signatures in the anti-PD-1-responsive group (FIG. 2C bottom). Previously, an interferon gamma signature was found to be differentially up-expressed in the pretreatment tumor biopsies from responding patients when a restricted set of immune genes were analyzed (Ribas et al., 2015). However, the technical approach may not be comparable to our whole tumor transcriptomic approach. We did note that the expression levels of HLA class I genes (HLA-A, -B, -C) trended higher among the responding tumors, although the differences were not statistically significant. Lastly, the complete loss of PTEN was reported to promote resistance to immune checkpoint blockade (Peng et al.; 2015), but there was only one case of homozygous PTEN deletion (with nearly undetectable PTEN mRNA expression; Figure S2A) in our cohort (in the non-responsive sub-group), limiting our ability to draw meaningful associations in this dataset. Generally, we did not observe a statistically significant difference in PTEN expression between anti-PD-1 responding versus non-responding tumors. Thus, individual gene-based expression analysis suggested mesenchymal and T cell-suppressive inflammatory or angiogenic tumor phenotypes as being associated with innate anti-PD-1 resistance.

We then queried biological processes represented by DEGs. While gene ontology (GO) enrichment analysis of genes up-expressed among responding tumors produced no significantly enriched terms, genes up-expressed among non-responding tumors were enriched for cell adhesion, ECM organization, wound healing and angiogenesis (FDR-adjusted p-values of GO gene sets shown in FIG. 2C). Using independently derived perturbation-based transcriptomic signatures (Molecular Signature Database; Table 3), we tested for differentially enriched processes in the responding versus non-responding pretreatment tumors (cutoff, 10% difference between the absolute medians of GSVA scores in the two groups; FDR-corrected Welch t-test p≤0.25). Gene sets meeting these standard cutoffs formed the core sets (FIG. 2D upper, in bold) from which we compiled additional concurrently enriched (nominal Welch t-test p≤0.1) and functionally related gene sets (FIG. 2D upper, Table 2). We considered these statistically weaker gene set enrichments biologically meaningful given the functional coherence of these gene signatures with the core signatures (Subramanian et al., 2005).

Importantly, a group of 26 transcriptomic signatures were co-enriched en bloc in 9 of 13 non-responding versus 1 of 15 responding pre-anti-PD-1 tumors (see Experimental Procedures). Co-enrichment of these signatures, collectively referred to as the Innate anti-PD-1 Resistance or IPRES signature, again indicated heightened mesenchymal transition, angiogenesis, hypoxia and wound healing. The concurrence of a tumor cell mesenchymal phenotype with an angiogenesis- and wound healing-related inflammatory microenvironment has been documented in the literature (Chen et al., 2015a; Chen et al., 2015b; Mak et al., 2015). Interestingly, this set of 26 IPRES signatures included signatures induced by MAPK inhibitor (MAPKi) treatment of melanoma tumors and cell lines (Table 3). We have shown recently that MAPKi treatment of melanoma cells induces transcriptome-wide re-programming leading to concurrent phenotype switches (Song et al., 2015). Notably, MAPKi-induced signatures of mesenchymal-invasive transition, angiogenesis, and wound healing signatures were detected in the residual melanoma tumors from patients on MAPKi therapy, suggesting that induction of these signatures may negatively impact responsiveness to combinatorial anti-PD-1/L1 therapy.

IPRES (Innate Anti-PD-1 Resistance) Signatures Define a Transcriptomic Subset Across Cancers The observations that IPRES content signatures were co-enriched in the same tumors (FIG. 2D) and that MAPKi induced these signatures concurrently (Table 3) implied co-regulated tumor phenotypes that together define a transcriptomic subset. To evaluate whether co-enrichment of IPRES content signatures was an exclusive feature of our cohort, we queried three additional cohorts of metastatic melanoma-derived RNASeq (Hugo et al., 2015; TCGA, 2015; Van Allen et al., 2015), including a cohort consisting of only $^{V600}$ BRAF mutant melanomas (cohort 3) (Hugo et al., 2015). We found that IPRES content signatures co-enriched not only in the same tumors but also in about a third of total samples in each of the four independent transcriptomic data sets (cohort 1 from this study, 10 IPRES-enriched tumors of 28 total tumors; cohort 2, 15 of 42; cohort 3, 11 of 32; cohort 4, 90 of 282) (FIG. 3A). Considering 126 among 384 total tumors as the background prevalence for co-enrichment of IPRES content signatures in metastatic melanoma, we determined that this IPRES-enriched transcriptomic subset was over-represented among the anti-PD-1 non-responding pretreatment tumors (Fisher P=0.013, odds ratio=4.6) and under-represented among the responding pretreatment tumors (Fisher P=0.04, odds ratio=0.15) within cohort 1. In contrast, co-enrichment of IPRES signatures was neither over-nor-under-represented among the responding or non-responding pre-anti-CTLA-4 melanoma tumors in cohort 2 (FIG. 5B) (Van Allen et al., 2015), which suggests that mechanisms of innate resistance to anti-PD-1 and anti-CTLA-4 are not necessarily similar.

Figure 3B:
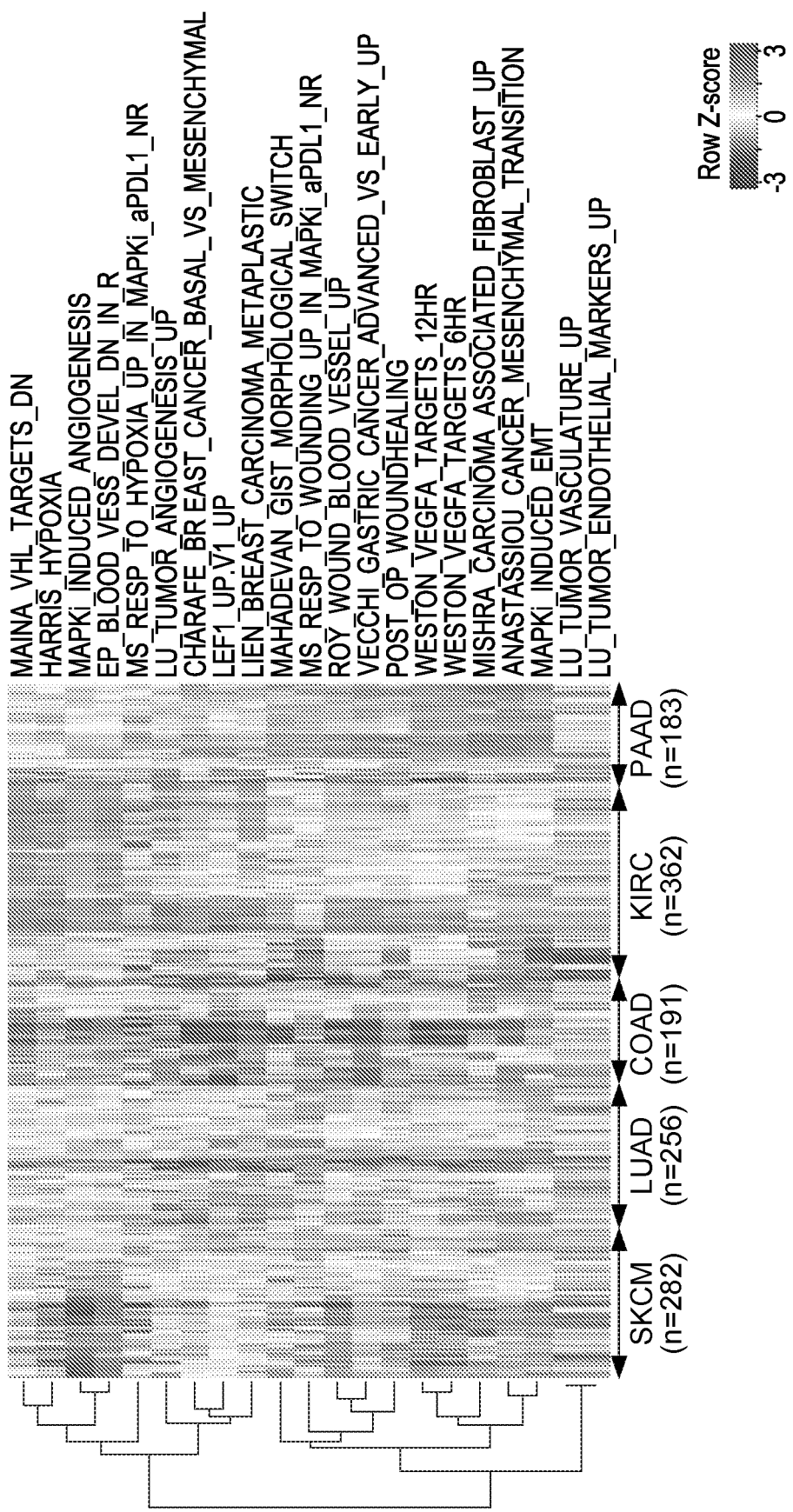

Furthermore, co-enrichment of the IPRES signatures defined a transcriptomic subset within not only melanoma but also all major common human malignancies analyzed (FIG. 3B). The IPRES-enriched transcriptomic subset of certain cancers such as pancreatic adenocarcinoma made up the majority of tumors. Within a side-by-side comparison, only six of 69 primary cutaneous melanomas showed co-enrichment of IPRES signatures, in contrast to 90 of 282 metastatic (TCGA) melanomas (P=3.9e-5, odds ratio=0.2) (FIG. 6), consistent with mesenchymal transition and metastasis gene sets among IPRES signatures. Thus, co-enrichment of IPRES signatures defines a distinct transcriptomic program that exists across cancers of distinct histology.

This study highlights the utility of both exome and transcriptome sequencing data generated from pretreatment tumor samples for the identification of potential determinants of response to anti-PD-1. Although the overall somatic mutational loads of anti-PD-1-responsive melanoma tumors were not significantly higher than those of non-responsive tumors, higher mutational loads associated significantly with better survival after anti-PD-1 therapy. This finding is still consistent with the notion that neoepitopes derived from somatic non-synonymous mutations are critical for deriving clinical benefits from anti-PD-1 therapy in melanoma. However, objective tumor responses, although strongly associated with survival benefits, did not appear to be driven overwhelmingly by the overall somatic mutational loads. That is to say, a relatively low mutational load did not preclude a tumor response. This is consistent with findings from gastrointestinal cancers where low mutational loads did not preclude tumor infiltration by mutation-reactive, class I and II-restricted T cells (Tran et al., 2015). Thus, overall somatic or predicted neoepitope loads of pretreatment melanoma tumors are not enough to predict response patterns to anti-PD-1 therapy.

In our cohort, responsive tumors were significantly enriched for (likely) loss-of-function mutations in BRCA2. As one would predict from the known function of BRCA2 in DNA repair, BRCA2-mutated melanomas harbored higher mutational loads than BRCA2-wildtype melanomas. Although it is conceivable that defective BRCA2-DNA repair results in specific mutational motifs (as opposed to the general increase in mutational load) that enhance responsiveness, it is also possible that cellular stress resulting from defective DNA repair could lead to increased cell death and anti-tumor immunity. Moreover, these data support the notion that tumor cell phenotypic plasticity (i.e., mesenchymal transition) and the resultant impacts on the microenvironment (e.g., ECM remodeling, cell adhesion, angiogenesis-features of immune suppressive wound healing) are critical barriers to anti-PD-1 responses. The limited number of patients in our melanoma cohort posed certain challenges to our analysis. For example, we relaxed the statistical stringency in single gene-based differential expression analysis (bypassing multiple hypothesis correction) to derive enough genes for gene ontology enrichment analysis. However, converging findings from alternative analysis (i.e., GSVA) of the transcriptome data helped to mitigate potential caveats. Finally, in separate work, we found that mutation-targeted therapy (i.e., MAPKi) induces tumor cell-autonomous changes (e.g., mesenchymal transition) (Song et al., 2015) and upregulates anti-PD-1 resistance-associated processes in residual tumors that have regressed in response to MAPKi treatment. Thus, while our findings in this study necessitate confirmation in independent tissue cohorts, the identification of transcriptomic features associated with anti-PD-1 resistance suggests that mitigation of IPRES-related biological processes may enhance response rates to anti-PD-1 (and anti-PD-1 plus MAPKi) therapy.

The following abbreviations are used in Tables 1-3, which have been submitted herewith as an ASCII text file:

TABLE 1

Differentially expressed genes in responding vs non-responding tumors

| Gene | Gene name |
|---|---|
| Pval | The Mann Whitney p-value of the expression difference in the responders (R) vs. non-responders (NR) |
| FDR | FDR corrected p-value of the Mann-Whitney test |
| Stats | The U statistics |
| diffAvg | Difference in the median expression in the responders substracted by those of the non responders |
| avg.R | Median expression in Responders (R) |
| avg.NR | Median expression in Non-responders (NR) |

TABLE 2

Differentially enriched genesets in responding vs non-responding tumors

| Geneset | Geneset name (only including genesets of size 25 and above) |
|---|---|
| Pval | The Welch T-test p-value of the GSVA enrichment score difference between the responders (R) vs. non-responders (NR) |
| FDR | FDR corrected p-value of the T-test |
| Stats | The T statistics |
| diffAvg | Difference in the median enrichment scores in the responders substracted by those of the non responders |
| avg.R | Median GSVA enrichment score in Responders (R) |
| avg.NR | Median GSVA enrichment score in Non-responders (NR) |

TABLE 3

MAPKi induced signature and others

| Geneset | Geneset name (only those not included in the Molecular Signature Database) |
|---|---|
| Detail | The details/source on the gene signatures |
| Gene Listing | The list of the genes in the signature |

Tables 1-3 and the data described in Example 1 can also be accessed via the following publication by the inventors: Hugo et al., 2016, Cell 165(1):35-44.

Example 2: Accession Numbers for Transcriptome and Sequencing Data

The accession number for the transcriptome data described in Example 1 is GEO: GSE78220. This data set is publicly available through the Gene Expression Omnibus (GEO), and can be obtained through the National Center for Biotechnology Information (NCBI) of Bethesda, Md. (https://www.ncbi.nlm.nih.gov/geo).

The whole-exome sequencing data described in Example 1 has been deposited to the Sequence Read Archive (SRA) and can be obtained through the National Center for Biotechnology Information (NCBI) of Bethesda, Md. (https://www.ncbi.nlm.nih.gov/sra), under the accession numbers SRA: SRP067938 (UCLA samples) and SRA: SRP090294 (Vanderbilt samples).

All of the publicly available GEO and SRA information described above is incorporated herein by reference.

REFERENCES

Chen, L., et al. (2015a). Metastasis is regulated via microRNA-200/ZEB1 axis control of tumour cell PD-L1 expression and intratumoral immunosuppression. Nat Commun 5, 5241.

Chen, L., et al. (2015b). The mutually regulatory loop of epithelial-mesenchymal transition and immunosuppression in cancer progression. Oncoimmunology 4, e1002731.

Favero, F., et al. (2015). Sequenza: allele-specific copy number and mutation profiles from tumor sequencing data. Ann Oncol 26, 64-70.

Hamid, O., et al. (2013). Safety and tumor responses with lambrolizumab (anti-PD-1) in melanoma. N Engl J Med 369, 134-144.

Hanzelmann, S., et al. (2013). GSVA: gene set variation analysis for microarray and RNA-seq data. BMC Bioinformatics 14, 7.

Hodis, E., et al. (2012). A landscape of driver mutations in melanoma. Cell 150, 251-263.

Hoek, K. S., et al. (2008). In vivo switching of human melanoma cells between proliferative and invasive states. Cancer Res 68, 650-656.

Holloman, W. K. (2011). Unraveling the mechanism of BRCA2 in homologous recombination. Nat Struct Mol Biol 18, 748-754.

Hoof, I., et al. (2009). NetMHCpan, a method for MHC class I binding prediction beyond humans. Immunogenetics 61, 1-13.

Hoos, A., et al, (2015). CCR 20th Anniversary Commentary: Immune-Related Response Criteria—Capturing Clinical Activity in Immuno-Oncology. Olin Cancer Res 21, 4989-4991.

Huang, D., W., et al. (2008). Systematic and integrative analysis of large gene lists using DAVID bioinformatics resources. Nat Protoc 4, 44-57.

Huang, D. W. (2009). Bioinformatics enrichment tools: paths toward the comprehensive functional analysis of large gene lists. Nucleic Acids Res 37, 1-13.

Hugo, W., et al. (2015). Non-genomic and Immune Evolution of Melanoma Acquiring MAPKi Resistance. Cell 162, 1271-1285.

Inkeles, M. S., et al. (2015). Comparison of molecular signatures from multiple skin diseases identifies mechanisms of immunopathogenesis. J Invest Dermatol 135, 151-159.

Karosiene, E., et al. (2013). NetMHCIIpan-3.0, a common pan-specific MHC class II prediction method including all three human MHC class II isotypes, HLA-DR, HLA-DP and HLA-DQ. Immunogenetics 65, 711-724.

Kim, D., et al. (2013). TopHat2: accurate alignment of transcriptomes in the presence of insertions, deletions and gene fusions. Genome Biol 14, R36.

Koboldt, D. C., et al. (2012). VarScan 2: somatic mutation and copy number alteration discovery in cancer by exome sequencing. Genome Res 22, 568-576.

Le, D. T., et al. (2015). PD-1 Blockade in Tumors with Mismatch-Repair Deficiency. N Engl J Med 372, 2509-2520.

Liu, C., et al. (2013). ATHLATES: accurate typing of human leukocyte antigen through exome sequencing. Nucleic Acids Res 41, e142.

Mak, M. P., et al. (2015). A Patient-Derived, Pan-Cancer EMT Signature Identifies Global Molecular Alterations and Immune Target Enrichment Following Epithelial-to-Mesenchymal Transition. Olin Cancer Res September 29, Epub ahead of print.

McCarthy, D. J., Chen, Y., and Smyth, G. K. (2012). Differential expression analysis of multifactor RNA-Seq experiments with respect to biological variation. Nucleic Acids Res 40, 4288-4297.

Mitchell, A., et al, (2015). The InterPro protein families database: the classification resource after 15 years. Nucleic Acids Res 43, D213-221.

Motz, G. T., and Coukos, G. (2011). The parallel lives of angiogenesis and immunosuppression: cancer and other tales. Nat Rev Immunol 11, 702-711.

Nielsen, M., et al. (2007). NetMHCpan, a method for quantitative predictions of peptide binding to any HLA-A and -B locus protein of known sequence. PLoS One 2, e796.

Peng, W., et al. (2015). Loss of PTEN promotes resistance to T cell-mediated immunotherapy. Cancer Discov December 8, Epub ahead of print.

Puzanov, I., et al. (2015). Pembrolizumab for advanced melanoma: effect of BRAFV600 mutation status and prior BRAF inhibitor therapy. Pigment Cell Melanoma Res 28, 807.

Ramanujam, S., et al. (2015). Anti-PD1 responses in BRAF mutant advanced melanoma patients with prior BRAF inhibitor or combined BRAF and MEK inhibitor therapy. Pigment Cell Melanoma Res 28, 808.

Ramos, A. H., et al. (2015). Oncotator: cancer variant annotation tool. Hum Mutat 36, E2423-2429.

Ribas, A., et al. (2015). Association of response to programmed death receptor 1 (PD-1) blockade with pembrolizumab (MK-3475) with an interferon-inflammatory immune gene signature. J Clin Oncol 33, abstr 3001.

Rizvi, N. A., et al. (2015). Cancer immunology. Mutational landscape determines sensitivity to PD-1 blockade in non-small cell lung cancer. Science 348, 124-128.

Schafer, M., and Werner, S. (2008). Cancer as an overhealing wound: an old hypothesis revisited. Nat Rev Mol Cell Biol 9, 628-638.

Sharma, P., and Allison, J. P. (2015). Immune checkpoint targeting in cancer therapy: toward combination strategies with curative potential. Cell 161, 205-214.

Shi, H., et al. (2014). Acquired Resistance and Clonal Evolution in Melanoma during BRAF Inhibitor Therapy. Cancer Discov 4, 80-93.

Simeone, E., et al. (2015). Correlation between BRAF mutational status and response to pembrolizumab. Pigment Cell Melanoma Res 28, 754.

Snyder, A., et al. (2014). Genetic basis for clinical response to CTLA-4 blockade in melanoma. N Engl J Med 371, 2189-2199.

Song, C., et al. (2015). Residual Melanoma Tumors on MAPKi Therapy Undergo Transcriptome-wide Phenotype Switching. Under revision, Subramanian, A., et al. (2005). Gene set enrichment analysis: a knowledge-based approach for interpreting genome-wide expression profiles. Proc Natl Acad Sci USA 102, 15545-15550.

TCGA (2012), Comprehensive molecular characterization of human colon and rectal cancer. Nature 487, 330-337.

TCGA (2013). Comprehensive molecular characterization of clear cell renal cell carcinoma. Nature 499, 43-49.

TCGA (2014). Comprehensive molecular profiling of lung adenocarcinoma. Nature 511, 543-550.

TCGA (2015). Genomic Classification of Cutaneous Melanoma. Cell 161, 1681-1696.

Topalian, S. L., et al. (2012). Safety, activity, and immune correlates of anti-PD-1 antibody in cancer. N Engl J Med 366, 2443-2454.

Tran, E., et al, (2015). Immunogenicity of somatic mutations in human gastrointestinal cancers. Science 350, 1387-1390.

Tumeh, P. C., et al. (2014). PD-1 blockade induces responses by inhibiting adaptive immune resistance. Nature 515, 568-571.

Van Allen, E. M., et al. (2015). Genomic correlates of response to CTLA-4 blockade in metastatic melanoma. Science 350, 207-211.

Voron, T., et al. (2014). Control of the immune response by pro-angiogenic factors, Front Oncol 4, 70

Wherry, E. J. (2011). T cell exhaustion. Nat Immunol 12, 492-499.

Wolchok, J. D., et al. (2009). Guidelines for the evaluation of immune therapy activity in solid tumors: immune-related response criteria. Olin Cancer Res 15, 7412-7420.

From the foregoing it will be appreciated that, although specific embodiments of the invention have been described herein for purposes of illustration, various modifications may be made without deviating from the spirit and scope of the invention. Accordingly, the invention is not limited except as by the appended claims.

Table 1, Related to FIG. 2

| Gene | Pval | FDR | Stats | diffAvg | avg.R | avg.NR |
|---|---|---|---|---|---|---|
| ALDH1L2 | 8.35E-05 | 0.117209693 | 18 | -2.253484 | -0.258861 | 1.994623 |
| MFAP2 | 0.000139575 | 0.195684571 | 20 | -3.252504 | 2.901905 | 6.154409 |
| CDH1 | 0.000178462 | 0.250025122 | 174 | 4.695203 | 6.19247 | 1.497267 |
| OLIG1 | 0.000226803 | 0.31752448 | 173 | 3.8139195 | 3.337104 | -0.4768155 |
| TRAF3IP2 | 0.000286255 | 0.400470605 | 172 | 1.787198 | 3.821787 | 2.034589 |
| TDRD10 | 0.000359381 | 0.502414638 | 24 | -1.1744323 | -2.002854 | -0.8284217 |
| CILP2 | 0.000556538 | 0.777484145 | 26 | -2.4147547 | -1.801058 | 0.6136967 |
| MEX3B | 0.000556538 | 0.777484145 | 26 | -1.0395443 | 0.4294017 | 1.468946 |
| SLC45A1 | 0.00068698 | 0.958336542 | 27 | -1.4736537 | -1.826097 | -0.3524433 |
| RASL11B | 0.000843915 | 1 | 28 | -1.7012004 | -1.382577 | 0.3186234 |
| PKDCC | 0.000843915 | 1 | 28 | -1.168662 | 1.29307 | 2.461732 |
| FOXC2 | 0.000987293 | 1 | 25.5 | -1.331849 | -2.426073 | -1.094224 |
| H1F0 | 0.001031404 | 1 | 29 | -1.262369 | 6.073513 | 7.335882 |
| SLC16A3 | 0.001255002 | 1 | 30 | -2.283607 | 4.243083 | 6.52669 |
| MXRA8 | 0.001255002 | 1 | 30 | -1.996743 | 3.272629 | 5.269372 |
| STC2 | 0.001255002 | 1 | 30 | -1.25939568 | -0.08335368 | 1.176042 |
| WISP1 | 0.001519838 | 1 | 31 | -1.8376125 | 0.2038025 | 2.041415 |
| CRLF1 | 0.001519838 | 1 | 31 | -1.3069933 | -1.470733 | -0.1637397 |
| LYSMD2 | 0.001519838 | 1 | 164 | 1.081506 | 3.762567 | 2.681061 |
| ZNF219 | 0.001519838 | 1 | 164 | 1.228109 | 4.29986 | 3.071751 |
| FBLN2 | 0.001832854 | 1 | 32 | -1.907241 | 2.231156 | 4.138397 |
| TSHZ3 | 0.001832854 | 1 | 32 | -1.6686799 | 0.2338531 | 1.902533 |
| CDR2L | 0.001832854 | 1 | 32 | -1.291553 | 1.677729 | 2.969282 |
| ITPRIPL1 | 0.001832854 | 1 | 32 | -1.271089 | -0.3441939 | 0.9268951 |
| WDR86 | 0.001832854 | 1 | 32 | -1.25951259 | -1.211709 | 0.04780359 |
| LOC102724050 | 0.001924489 | 1 | 34 | -1.111756 | -3.321928 | -2.210172 |
| CCL7 | 0.002014619 | 1 | 30 | -2.1835543 | -2.396656 | -0.2131017 |
| FBLN1 | 0.002200781 | 1 | 33 | -2.589232 | 4.17057 | 6.759802 |
| IL10 | 0.002200781 | 1 | 33 | -1.1208539 | -0.5407132 | 0.5801407 |
| USP2 | 0.002200781 | 1 | 162 | 1.8762153 | 1.101452 | -0.7747633 |
| MIR503HG | 0.00263206 | 1 | 34 | -1.9319315 | -0.8976805 | 1.034251 |
| ITGA5 | 2.63E-03 | 1 | 34 | -1.773712 | 3.367958 | 5.14167 |
| SPAG4 | 0.003135076 | 1 | 35 | -2.22776434 | 0.01987766 | 2.247642 |
| F2RL3 | 0.003135076 | 1 | 35 | -1.4716304 | -1.314709 | 0.1569214 |
| RAB31 | 0.003135076 | 1 | 35 | -1.226698 | 3.569357 | 4.796055 |
| HOGA1 | 0.003135076 | 1 | 160 | 1.7582137 | 1.082658 | -0.6755557 |
| C20orf26 | 0.003192318 | 1 | 33 | -1.277359 | -2.820515 | -1.543156 |
| LOC388849 | 0.003720352 | 1 | 36 | -2.1623767 | -1.664514 | 0.4978627 |
| SH3RF3 | 0.003720352 | 1 | 36 | -1.8524042 | -0.1713912 | 1.681058 |
| FBN2 | 0.003720352 | 1 | 36 | -1.59958421 | -1.634473 | -0.0348888 |
| ANO1 | 0.003720352 | 1 | 36 | -1.206266 | 1.300973 | 2.507239 |
| HSPB2 | 0.003720352 | 1 | 159 | 2.622637 | 4.730273 | 2.107636 |
| ADAMTS12 | 0.004397983 | 1 | 37 | -1.6475076 | -1.076661 | 0.5708466 |
| MMP2 | 0.004397983 | 1 | 37 | -1.280251 | 4.978145 | 6.258396 |
| TMEM204 | 0.004397983 | 1 | 37 | -1.086398 | 3.180613 | 4.267011 |
| CYP39A1 | 0.004397983 | 1 | 158 | 1.0927381 | 0.5097313 | -0.5830068 |
| CRYAB | 0.004397983 | 1 | 158 | 1.42328 | 8.262767 | 6.839487 |
| GRAMD3 | 0.004397983 | 1 | 158 | 1.511263 | 3.240479 | 1.729216 |
| RNF43 | 0.004397983 | 1 | 158 | 3.366819 | 1.909059 | -1.45776 |
| LINC00221 | 0.004749632 | 1 | 159 | 5.582152 | 3.188421 | -2.393731 |
| APCDD1L | 0.004930722 | 1 | 36 | -1.8237489 | -2.481193 | -0.6574441 |
| GPC3 | 0.005180577 | 1 | 38 | -2.5453944 | 0.1213066 | 2.666701 |
| KIAA1644 | 0.005180577 | 1 | 38 | -1.7990805 | -2.065944 | -0.2668635 |
| PXDN | 0.005180577 | 1 | 38 | -1.792308 | 1.703183 | 3.495491 |
| F3 | 0.005180577 | 1 | 38 | -1.5700116 | 0.4601974 | 2.030209 |
| EBF4 | 0.005180577 | 1 | 38 | -1.4361501 | 0.3928779 | 1.829028 |
| CPE | 0.005180577 | 1 | 38 | -1.35976 | 2.751096 | 4.110856 |
| MMRN1 | 0.005180577 | 1 | 38 | -1.3366295 | -1.708064 | -0.3714345 |
| PRR5L | 0.005180577 | 1 | 38 | -1.1112193 | 0.2803447 | 1.391564 |
| GJA5 | 0.005180577 | 1 | 38 | -1.0969269 | 0.5459091 | 1.642836 |
| DCSTAMP | 0.005180577 | 1 | 38 | -1.0039008 | -1.84868 | -0.8447792 |
| BTN2A2 | 0.005180577 | 1 | 157 | 1.095465 | 4.162299 | 3.066834 |
| 3-Mar | 0.005180577 | 1 | 157 | 1.347824 | 1.480614 | 0.13279 |
| PLEKHB1 | 0.005180577 | 1 | 157 | 1.960591 | 4.311329 | 2.350738 |
| SCGB3A1 | 0.00555513 | 1 | 37.5 | -1.671262 | -2.749919 | -1.078657 |
| EGFL6 | 0.006080579 | 1 | 39 | -2.4310006 | -0.4087696 | 2.022231 |

-continued

| Gene | Pval | FDR | Stats | diffAvg | avg.R | avg.NR |
|---|---|---|---|---|---|---|
| PAM | 0.006080579 | 1 | 39 | −1.647636 | 2.729207 | 4.376843 |
| JAM2 | 0.006080579 | 1 | 39 | −1.3712591 | 0.3323929 | 1.703652 |
| AXL | 0.006080579 | 1 | 39 | −1.361305 | 2.113637 | 3.474942 |
| TMEM100 | 0.006080579 | 1 | 39 | −1.2198963 | −1.503462 | −0.2835657 |
| RASL12 | 0.006080579 | 1 | 39 | −1.0555778 | 0.8514472 | 1.907025 |
| GFPT2 | 0.006080579 | 1 | 39 | −1.026043 | 1.809454 | 2.835497 |
| CELSR2 | 0.006080579 | 1 | 156 | 1.263952 | 3.66754 | 2.403588 |
| APOM | 0.006080579 | 1 | 156 | 1.6581358 | −0.2957672 | −1.953903 |
| AJAP1 | 0.006563274 | 1 | 38 | −1.076949 | −2.593238 | −1.516289 |
| GPR150 | 0.007091815 | 1 | 39 | −1.588246 | −2.692376 | −1.10413 |
| EDIL3 | 0.007112784 | 1 | 40 | −2.5638916 | −0.4841846 | 2.079707 |
| GEM | 0.007112784 | 1 | 40 | −2.140455 | 1.512697 | 3.653152 |
| DNM1 | 0.007112784 | 1 | 40 | −2.0213723 | 0.9354597 | 2.956832 |
| CLMP | 0.007112784 | 1 | 40 | −1.9378345 | −0.3041335 | 1.633701 |
| SH3RF3-AS1 | 0.007112784 | 1 | 40 | −1.6252225 | −1.87546 | −0.2502375 |
| FABP3 | 0.007112784 | 1 | 40 | −1.499286 | 2.074779 | 3.574065 |
| ID1 | 0.007112784 | 1 | 40 | −1.264457 | 3.93412 | 5.198577 |
| ANGPT2 | 0.007112784 | 1 | 40 | −1.21490704 | 0.04675296 | 1.26166 |
| MRC2 | 0.007112784 | 1 | 40 | −1.025815 | 2.938482 | 3.964297 |
| HHATL | 0.00725996 | 1 | 156 | 2.2708138 | −0.8636852 | −3.134499 |
| NMU | 0.007536569 | 1 | 39 | −1.8720997 | −1.852886 | 0.0192137 |
| LINC00632 | 0.007897147 | 1 | 40 | −1.28982 | −3.321928 | −2.032108 |
| IRX1 | 0.007992436 | 1 | 39.5 | −1.235847 | −1.667956 | −0.432109 |
| CYS1 | 0.008291883 | 1 | 41 | −1.6651333 | −2.255144 | −0.5900107 |
| HEYL | 0.008291883 | 1 | 41 | −1.6219248 | 0.7036722 | 2.325597 |
| GPR84 | 0.008291883 | 1 | 41 | −1.2325053 | 0.1132177 | 1.345723 |
| RAB3IP | 0.008291883 | 1 | 154 | 1.343584 | 0.6313092 | −0.7122748 |
| LOC100129046 | 0.00891629 | 1 | 154.5 | 1.142917 | −1.688302 | −2.831219 |
| SNORD89 | 0.009048926 | 1 | 145 | 7.520084 | 4.198156 | −3.321928 |
| HES7 | 0.009153676 | 1 | 40.5 | −1.154026 | −2.631213 | −1.477187 |
| LINC01152 | 0.009239898 | 1 | 154.5 | 1.1022572 | −0.5258828 | −1.62814 |
| TAC4 | 0.009519518 | 1 | 42 | −1.197991 | −3.321928 | −2.123937 |
| CCDC74A | 0.009635448 | 1 | 42 | −2.52187 | −0.919895 | 1.601975 |
| SAMD11 | 0.009635448 | 1 | 42 | −2.1402904 | 0.2375166 | 2.377807 |
| DKK3 | 0.009635448 | 1 | 42 | −2.110333 | 1.932141 | 4.042474 |
| HTRA3 | 0.009635448 | 1 | 42 | −2.030954 | 1.620741 | 3.651695 |
| TRPC6 | 0.009635448 | 1 | 42 | −1.7905635 | −1.433783 | 0.3567805 |
| HOXA11 | 0.009635448 | 1 | 42 | −1.61043691 | 0.06340009 | 1.673837 |
| C14orf37 | 0.009635448 | 1 | 42 | −1.4785885 | −0.9078196 | 0.5707689 |
| FLT1 | 0.009635448 | 1 | 42 | −1.476594 | 1.489743 | 2.966337 |
| FER1L4 | 0.009635448 | 1 | 42 | −1.3559933 | −2.293388 | −0.9373947 |
| LAYN | 0.009635448 | 1 | 42 | −1.3290929 | −0.4101915 | 0.9189014 |
| PPP1R14A | 0.009635448 | 1 | 42 | −1.274264 | 1.475811 | 2.750075 |
| KCNE4 | 0.009635448 | 1 | 42 | −1.237635 | 0.583779 | 1.821414 |
| GPR116 | 0.009635448 | 1 | 42 | −1.029448 | 1.602861 | 2.632309 |
| COLEC12 | 0.009635448 | 1 | 42 | −1.010921 | 1.39335 | 2.404271 |
| NXPH3 | 0.009635448 | 1 | 42 | −1.008978 | −2.619169 | −1.610191 |
| NFIL3 | 0.009635448 | 1 | 42 | −1.008108 | 2.292128 | 3.300236 |
| RAB17 | 0.009635448 | 1 | 153 | 1.196085 | 4.801034 | 3.604949 |
| DISP2 | 0.009635448 | 1 | 153 | 1.4390312 | 0.1340842 | −1.304947 |
| CNN1 | 0.01116047 | 1 | 43 | −1.8911616 | −0.4653586 | 1.425803 |
| ROR2 | 0.01116047 | 1 | 43 | −1.46636719 | −0.04972719 | 1.41664 |
| SLC38A5 | 0.01116047 | 1 | 43 | −1.4381184 | 0.3343566 | 1.772475 |
| COL6A3 | 0.01116047 | 1 | 43 | −1.405908 | 4.872065 | 6.277973 |
| SYNGR3 | 0.01116047 | 1 | 43 | −1.3828052 | −0.6775792 | 0.705226 |
| VEGFC | 0.01116047 | 1 | 43 | −1.2443599 | 0.3784561 | 1.622816 |
| TGFBR3L | 0.01116047 | 1 | 43 | −1.2291565 | −2.173865 | −0.9447085 |
| NUMBL | 0.01116047 | 1 | 43 | −1.214687 | 2.444792 | 3.659479 |
| DACT1 | 0.01116047 | 1 | 43 | −1.1796679 | 0.2587661 | 1.438434 |
| HYKK | 0.01116047 | 1 | 152 | 1.0954206 | 1.680763 | 0.5853424 |
| ST3GAL6 | 0.01116047 | 1 | 152 | 1.277797 | 5.353817 | 4.07602 |
| CEACAM1 | 0.01116047 | 1 | 152 | 1.708838 | 4.707439 | 2.998601 |
| DDR1 | 0.01116047 | 1 | 152 | 1.8984673 | 2.644264 | 0.7457967 |
| RSPO4 | 0.01124532 | 1 | 42 | −1.424701 | −2.724322 | −1.299621 |
| HHIP-AS1 | 0.0116467 | 1 | 42.5 | −1.414025 | −2.934476 | −1.520451 |
| LOC101928710 | 0.0126183 | 1 | 43 | −1.015177 | −2.686815 | −1.671638 |
| LOC644919 | 0.01265542 | 1 | 151.5 | 3.632845 | 1.08657 | −2.546275 |
| LINC01013 | 0.01274058 | 1 | 152 | 1.5056521 | −0.4482399 | −1.953892 |
| SRPX2 | 0.01288713 | 1 | 44 | −2.033529 | 0.54541 | 2.578939 |
| TIMP3 | 0.01288713 | 1 | 44 | −1.897088 | 5.587529 | 7.484617 |
| PALM2 | 0.01288713 | 1 | 44 | −1.8721072 | −2.177301 | −0.3051938 |
| TPPP3 | 0.01288713 | 1 | 44 | −1.769761 | 2.316496 | 4.086257 |
| VCAN | 0.01288713 | 1 | 44 | −1.7074 | 3.369027 | 5.076427 |
| BCAT1 | 0.01288713 | 1 | 44 | −1.5895141 | 0.4454619 | 2.034976 |
| FBLN7 | 0.01288713 | 1 | 44 | −1.5799961 | 0.6409309 | 2.220927 |
| FHL5 | 0.01288713 | 1 | 44 | −1.5069808 | −1.973551 | −0.4665702 |
| DPP4 | 0.01288713 | 1 | 44 | −1.4708449 | −0.5425276 | 0.9283173 |

-continued

| Gene | Pval | FDR | Stats | diffAvg | avg.R | avg.NR |
|---|---|---|---|---|---|---|
| MMP28 | 0.01288713 | 1 | 44 | −1.4138624 | −0.6024489 | 0.8114135 |
| METRNL | 0.01288713 | 1 | 44 | −1.404166 | 4.508162 | 5.912328 |
| ID3 | 0.01288713 | 1 | 44 | −1.316347 | 4.157476 | 5.473823 |
| PDGFD | 0.01288713 | 1 | 44 | −1.2057017 | 0.7174033 | 1.923105 |
| ZMIZ1-AS1 | 0.01288713 | 1 | 44 | −1.1963137 | −1.432852 | −0.2365383 |
| SERPINH1 | 0.01288713 | 1 | 44 | −1.075085 | 6.622783 | 7.697868 |
| ERMP1 | 0.01288713 | 1 | 151 | 1.012438 | 3.351498 | 2.33906 |
| METTL24 | 0.01304391 | 1 | 44 | −1.646125 | −3.130727 | −1.484602 |
| HAPLN1 | 0.0137077 | 1 | 43.5 | −1.142776 | −3.002558 | −1.859782 |
| LOC101927129 | 0.01424912 | 1 | 146 | 2.152855 | −1.169073 | −3.321928 |
| GAL | 0.01483526 | 1 | 45 | −2.949571 | −1.325136 | 1.624435 |
| INHBA | 0.01483526 | 1 | 45 | −2.61975047 | 0.08821353 | 2.707964 |
| ADAMTS7 | 0.01483526 | 1 | 45 | −2.15874052 | −0.01255252 | 2.146188 |
| PRRX1 | 0.01483526 | 1 | 45 | −1.982901 | 3.002196 | 4.985097 |
| CACNA1H | 0.01483526 | 1 | 45 | −1.8773198 | −1.224324 | 0.6529958 |
| EFCAB4A | 0.01483526 | 1 | 45 | −1.8327635 | −0.7696125 | 1.063151 |
| HOXA13 | 0.01483526 | 1 | 45 | −1.7780097 | −2.025691 | −0.2476813 |
| COL6A2 | 0.01483526 | 1 | 45 | −1.621793 | 6.523097 | 8.14489 |
| SEMA3F | 0.01483526 | 1 | 45 | −1.431472 | 1.508142 | 2.939614 |
| CERCAM | 0.01483526 | 1 | 45 | −1.272418 | 4.440002 | 5.71242 |
| IPO9-AS1 | 0.01483526 | 1 | 45 | −1.2194581 | −0.8265527 | 0.3929054 |
| ITGA8 | 0.01483526 | 1 | 45 | −1.1709789 | −1.762241 | −0.5912621 |
| MEX3D | 0.01483526 | 1 | 45 | −1.142663 | 3.15812 | 4.300783 |
| EFNB2 | 0.01483526 | 1 | 45 | −1.134314 | 1.420504 | 2.554818 |
| HPCAL1 | 0.01483526 | 1 | 45 | −1.121826 | 5.10078 | 6.222606 |
| HIC1 | 0.01483526 | 1 | 45 | −1.00638 | 1.711539 | 2.717919 |
| RTP4 | 0.01483526 | 1 | 150 | 1.492421 | 4.29354 | 2.801119 |
| ST6GAL1 | 0.01483526 | 1 | 150 | 1.893552 | 5.384045 | 3.490493 |
| MYO5B | 0.01483526 | 1 | 150 | 2.136646 | 1.106958 | −1.029688 |
| TBX5 | 0.01645418 | 1 | 45 | −1.756039 | −3.062714 | −1.306675 |
| FAM212B-AS1 | 0.0165875 | 1 | 45 | −1.481315 | −2.793389 | −1.312074 |
| HOXA11-AS | 0.01702749 | 1 | 46 | −1.9803441 | −1.363356 | 0.6169881 |
| HPDL | 0.01702749 | 1 | 46 | −1.67877 | 1.086386 | 2.765156 |
| SLC6A9 | 0.01702749 | 1 | 46 | −1.5952475 | 0.3078715 | 1.903119 |
| HEPH | 0.01702749 | 1 | 46 | −1.44800957 | −0.08735857 | 1.360651 |
| PMEPA1 | 0.01702749 | 1 | 46 | −1.435676 | 2.639133 | 4.074809 |
| PRR16 | 0.01702749 | 1 | 46 | −1.4286561 | −0.3938591 | 1.034797 |
| FHL1 | 0.01702749 | 1 | 46 | −1.395712 | 2.878072 | 4.273784 |
| PTN | 0.01702749 | 1 | 46 | −1.379301 | 0.340568 | 1.719869 |
| SDK1 | 0.01702749 | 1 | 46 | −1.3556552 | −1.903317 | −0.5476618 |
| FOXL1 | 0.01702749 | 1 | 46 | −1.3425475 | −1.805673 | −0.4631255 |
| KCNMA1 | 0.01702749 | 1 | 46 | −1.331075 | 2.320889 | 3.651964 |
| FAM225A | 0.01702749 | 1 | 46 | −1.169102 | −2.205876 | −1.036774 |
| ZNF695 | 0.01702749 | 1 | 46 | −1.16775289 | −1.24708 | −0.0793271 |
| SCARNA12 | 0.01702749 | 1 | 46 | −1.164094 | 1.709207 | 2.873301 |
| PLA2R1 | 0.01702749 | 1 | 46 | −1.1124749 | −1.467751 | −0.3552761 |
| NT5DC2 | 0.01702749 | 1 | 46 | −1.046505 | 4.714702 | 5.761207 |
| ACE | 0.01702749 | 1 | 46 | −1.020677 | 1.35091 | 2.371587 |
| LDB2 | 0.01702749 | 1 | 46 | −1.005769 | 1.390156 | 2.395925 |
| NRP1 | 0.01702749 | 1 | 46 | −1.003036 | 2.899925 | 3.902961 |
| GPR56 | 0.01702749 | 1 | 149 | 1.048476 | 7.053068 | 6.004592 |
| EPB41L4A-AS1 | 0.01702749 | 1 | 149 | 1.10751 | 5.10299 | 3.99548 |
| ARHGEF37 | 0.01702749 | 1 | 149 | 1.6799081 | 0.7765883 | −0.9033198 |
| TRIM51 | 0.01702749 | 1 | 149 | 1.9849281 | 1.590777 | −0.3941511 |
| ATP8A2 | 0.01702749 | 1 | 149 | 2.0159442 | 0.2334482 | −1.782496 |
| HBM | 0.01750613 | 1 | 47 | −1.690021 | −3.321928 | −1.631907 |
| GABRG2 | 0.01750613 | 1 | 148 | 1.718022 | −1.603906 | −3.321928 |
| LINC00578 | 0.01790656 | 1 | 46 | −1.005253 | −2.902149 | −1.896896 |
| LRRC26 | 0.01917838 | 1 | 148 | 1.195955 | −2.125973 | −3.321928 |
| TMEM158 | 0.01948622 | 1 | 47 | −2.873846 | 2.508251 | 5.382097 |
| PLAUR | 0.01948622 | 1 | 47 | −2.334589 | 3.172432 | 5.507021 |
| FOXF1 | 0.01948622 | 1 | 47 | −2.1868255 | −1.842739 | 0.3440865 |
| CCL8 | 0.01948622 | 1 | 47 | −1.956467 | 1.287895 | 3.244362 |
| COL6A1 | 0.01948622 | 1 | 47 | −1.747471 | 6.340201 | 8.087672 |
| STARD13 | 0.01948622 | 1 | 47 | −1.6878537 | 0.4416003 | 2.129454 |
| GIPC3 | 0.01948622 | 1 | 47 | −1.6721032 | −0.9430378 | 0.7290654 |
| NID1 | 0.01948622 | 1 | 47 | −1.662789 | 3.175343 | 4.838132 |
| FBLN5 | 0.01948622 | 1 | 47 | −1.642695 | 2.042264 | 3.684959 |
| OLFML2B | 0.01948622 | 1 | 47 | −1.514192 | 2.910871 | 4.425063 |
| OAF | 0.01948622 | 1 | 47 | −1.441507 | 4.129736 | 5.571243 |
| ENC1 | 0.01948622 | 1 | 47 | −1.312514 | 2.675434 | 3.987948 |
| SSPN | 0.01948622 | 1 | 47 | −1.269844 | 1.305778 | 2.575622 |
| PTHLH | 0.01948622 | 1 | 47 | −1.2605866 | −0.8903185 | 0.3702681 |
| MECOM | 0.01948622 | 1 | 47 | −1.21123881 | −0.06847881 | 1.14276 |
| WDR86-AS1 | 0.01948622 | 1 | 47 | −1.1843749 | −2.091 | −0.9066251 |

-continued

| Gene | Pval | FDR | Stats | diffAvg | avg.R | avg.NR |
| --- | --- | --- | --- | --- | --- | --- |
| UBE2C | 0.01948622 | 1 | 47 | −1.025868 | 5.67428 | 6.700148 |
| NRIP3 | 0.01948622 | 1 | 47 | −1.024896 | 1.074807 | 2.099703 |
| ENPEP | 0.01948622 | 1 | 47 | −1.02038256 | 0.05299244 | 1.073375 |
| PLEKHG3 | 0.01948622 | 1 | 148 | 1.140837 | 3.65011 | 2.509273 |
| PKD1L2 | 0.01948622 | 1 | 148 | 2.1745609 | 0.1205039 | −2.054057 |
| LOC101929268 | 0.02028025 | 1 | 47 | −1.286654 | −3.192715 | −1.906061 |
| CATIP-AS1 | 0.02124609 | 1 | 47 | −1.8478443 | −1.927705 | −0.0798607 |
| FGF13-AS1 | 0.0217214 | 1 | 147 | 1.334989 | −1.687874 | −3.022863 |
| TPTE | 0.0222316 | 1 | 146.5 | 3.40908326 | 0.08715526 | −3.321928 |
| ITIH5 | 0.02223713 | 1 | 48 | −3.737004 | −1.213527 | 2.523477 |
| EMILIN1 | 0.02223713 | 1 | 48 | −2.070662 | 3.671441 | 5.742103 |
| PTH1R | 0.02223713 | 1 | 48 | −1.7366385 | −1.204566 | 0.5320725 |
| SLC22A4 | 0.02223713 | 1 | 48 | −1.6097233 | −1.316553 | 0.2931703 |
| RNF152 | 0.02223713 | 1 | 48 | −1.4198271 | −1.226032 | 0.1937951 |
| TNFAIP6 | 0.02223713 | 1 | 48 | −1.402084 | 1.223626 | 2.62571 |
| RGAG4 | 0.02223713 | 1 | 48 | −1.3482349 | −0.6562943 | 0.6919406 |
| LOXL2 | 0.02223713 | 1 | 48 | −1.346063 | 2.652259 | 3.998322 |
| LY6H | 0.02223713 | 1 | 48 | −1.3215549 | −1.963243 | −0.6416881 |
| MAGEL2 | 0.02223713 | 1 | 48 | −1.207896 | −2.419098 | −1.211202 |
| CDKN1C | 0.02223713 | 1 | 48 | −1.168296 | 2.708437 | 3.876733 |
| MRVI1 | 0.02223713 | 1 | 48 | −1.1377988 | −0.5741916 | 0.5636072 |
| PTPRE | 0.02223713 | 1 | 48 | −1.13041 | 1.395853 | 2.526263 |
| LEPREL2 | 0.02223713 | 1 | 48 | −1.127943 | 2.597155 | 3.725098 |
| ALDH1A2 | 0.02223713 | 1 | 48 | −1.0787029 | −1.492162 | −0.4134591 |
| RPL34 | 0.02223713 | 1 | 147 | 1.006675 | 9.759733 | 8.753058 |
| NEAT1 | 0.02223713 | 1 | 147 | 1.16549 | 7.445925 | 6.280435 |
| CPS1 | 0.02223713 | 1 | 147 | 1.9768612 | 1.414547 | −0.5623142 |
| SNORD15B | 0.02292394 | 1 | 48 | −1.595452 | 1.534622 | 3.130074 |
| FLJ42351 | 0.02391834 | 1 | 48 | −1.4492607 | −0.8537332 | 0.5955275 |
| WNT7B | 0.02397618 | 1 | 48 | −1.547614 | −3.028052 | −1.480438 |
| SNORA52 | 0.02427559 | 1 | 52 | −6.505756 | −3.321928 | 3.183828 |
| SNORA62 | 0.02466063 | 1 | 53 | −4.932061 | −3.321928 | 1.610133 |
| P4HA3 | 0.02530484 | 1 | 49 | −2.406904 | −1.258399 | 1.148505 |
| CRABP2 | 0.02530484 | 1 | 49 | −2.265174 | 1.975324 | 4.240498 |
| SEMA3A | 0.02530484 | 1 | 49 | −2.1930616 | −1.980013 | 0.2130486 |
| ANGPTL2 | 0.02530484 | 1 | 49 | −1.767777 | 2.845684 | 4.613461 |
| LINC00899 | 0.02530484 | 1 | 49 | −1.6165 | −1.361235 | 0.255265 |
| MYL9 | 0.02530484 | 1 | 49 | −1.442777 | 4.913742 | 6.356519 |
| SERPINE1 | 0.02530484 | 1 | 49 | −1.377786 | 3.491096 | 4.868882 |
| CCL2 | 0.02530484 | 1 | 49 | −1.344696 | 5.036281 | 6.380977 |
| TCF4 | 0.02530484 | 1 | 49 | −1.200429 | 1.876104 | 3.076533 |
| GLIS3 | 0.02530484 | 1 | 49 | −1.16415067 | −1.198068 | −0.0339173 |
| TRIL | 0.02530484 | 1 | 49 | −1.1438619 | 0.1356301 | 1.279492 |
| SEMA6B | 0.02530484 | 1 | 49 | −1.125134 | 2.201982 | 3.327116 |
| ST6GALNAC4 | 0.02530484 | 1 | 49 | −1.097042 | 3.04954 | 4.146582 |
| MSX1 | 0.02530484 | 1 | 49 | −1.065628 | 1.23894 | 2.304568 |
| GPR124 | 0.02530484 | 1 | 49 | −1.062327 | 2.613997 | 3.676324 |
| ESAM | 0.02530484 | 1 | 49 | −1.038864 | 2.788132 | 3.826996 |
| DDIT3 | 0.02530484 | 1 | 49 | −1.019212 | 4.554985 | 5.574197 |
| AKR1E2 | 0.02530484 | 1 | 49 | −1.0092638 | −0.5934078 | 0.415856 |
| RPS6KL1 | 0.02530484 | 1 | 146 | 1.03440025 | 0.03140225 | −1.002998 |
| SULT1A1 | 0.02530484 | 1 | 146 | 1.0376764 | 1.881821 | 0.8441446 |
| STX3 | 0.02530484 | 1 | 146 | 1.039334 | 3.960373 | 2.921039 |
| EFCAB5 | 0.02530484 | 1 | 146 | 1.05557 | −1.558079 | −2.613649 |
| ST3GAL5 | 0.02530484 | 1 | 146 | 1.17081 | 5.639116 | 4.468306 |
| C11orf52 | 0.02530484 | 1 | 146 | 1.350626 | −1.001451 | −2.352077 |
| JMJD7-PLA2G4B | 0.02530484 | 1 | 146 | 1.3567436 | −0.1411644 | −1.497908 |
| PLEKHH1 | 0.02530484 | 1 | 146 | 1.487662 | 3.143167 | 1.655505 |
| LINC00277 | 0.02530484 | 1 | 146 | 1.6825415 | 1.0643 | −0.6182415 |
| C4orf19 | 0.02530484 | 1 | 146 | 2.64644 | 0.70828 | −1.93816 |
| HIST1H2AB | 0.02552604 | 1 | 50 | −1.408815 | −3.321928 | −1.913113 |
| GABRA2 | 0.02553886 | 1 | 51 | −1.070547 | −3.321928 | −2.251381 |
| HPCA | 0.02660856 | 1 | 49 | −1.23044 | −2.959882 | −1.729442 |
| C6orf223 | 0.02660856 | 1 | 49 | −1.197956 | −3.092173 | −1.894217 |
| LOC441455 | 0.02660856 | 1 | 49 | −1.030773 | −2.99957 | −1.968797 |
| ST8SIA6 | 0.02694265 | 1 | 146 | 1.0924452 | −0.6998318 | −1.792277 |
| LINC01021 | 0.02694265 | 1 | 146 | 2.0712627 | −0.3186803 | −2.389943 |
| PSG8 | 0.0273041 | 1 | 144 | 1.100138 | −2.22179 | −3.321928 |
| NOX5 | 0.02864024 | 1 | 145.5 | 1.2734099 | −0.3089081 | −1.582318 |
| COL8A1 | 0.02871757 | 1 | 50 | −2.5665424 | 0.4148066 | 2.981349 |
| STC1 | 0.02871757 | 1 | 50 | −1.9965129 | 0.8449721 | 2.841485 |
| COL13A1 | 0.02871757 | 1 | 50 | −1.7085358 | −0.7514421 | 0.9570937 |
| RCN3 | 0.02871757 | 1 | 50 | −1.654094 | 3.766675 | 5.420769 |
| EVA1B | 0.02871757 | 1 | 50 | −1.647569 | 4.092042 | 5.739611 |
| CPED1 | 0.02871757 | 1 | 50 | −1.545909 | −0.499869 | 1.04604 |
| C17orf82 | 0.02871757 | 1 | 50 | −1.483023377 | −1.479899 | 0.00312438 |

-continued

| Gene | Pval | FDR | Stats | diffAvg | avg.R | avg.NR |
|---|---|---|---|---|---|---|
| PROCR | 0.02871757 | 1 | 50 | −1.465655 | 2.445615 | 3.91127 |
| C3orf80 | 0.02871757 | 1 | 50 | −1.1982322 | −0.2724454 | 0.9257868 |
| LRRTM2 | 0.02871757 | 1 | 50 | −1.133281 | −2.750461 | −1.61718 |
| LOC100499489 | 0.02871757 | 1 | 50 | −1.1212869 | −0.7153816 | 0.4059053 |
| TRPV4 | 0.02871757 | 1 | 50 | −1.0741284 | 0.4505066 | 1.524635 |
| CEP112 | 0.02871757 | 1 | 50 | −1.0601436 | 0.4160074 | 1.476151 |
| KIAA0040 | 0.02871757 | 1 | 50 | −1.018032 | 1.221893 | 2.239925 |
| NGF | 0.02871757 | 1 | 50 | −1.0106234 | −1.587524 | −0.5769006 |
| NT5DC1 | 0.02871757 | 1 | 145 | 1.033774 | 3.494742 | 2.460968 |
| SLC44A5 | 0.03015565 | 1 | 145 | 1.072754 | −1.822174 | −2.894928 |
| LOC101929532 | 0.03029154 | 1 | 50 | −1.007715 | −3.059655 | −2.05194 |
| RBAKDN | 0.0319548 | 1 | 50.5 | −2.6151833 | −1.981594 | 0.6335893 |
| LOC102467146 | 0.03195593 | 1 | 143.5 | 1.140883 | −2.181045 | −3.321928 |
| TBX5-AS1 | 0.03204969 | 1 | 51 | −1.237403 | −3.063708 | −1.826305 |
| OPN4 | 0.03204969 | 1 | 51 | −1.018896 | −3.164355 | −2.145459 |
| MMP13 | 0.0321668 | 1 | 50.5 | −3.276935 | −1.757655 | 1.51928 |
| LUM | 0.03250261 | 1 | 51 | −2.232361 | 5.120217 | 7.352578 |
| FSCN1 | 0.03250261 | 1 | 51 | −2.228441 | 4.476832 | 6.705273 |
| CCDC74B | 0.03250261 | 1 | 51 | −1.9133374 | −1.321165 | 0.5921724 |
| CTXN1 | 0.03250261 | 1 | 51 | −1.842216 | 2.375596 | 4.217812 |
| RUNX2 | 0.03250261 | 1 | 51 | −1.7430551 | 0.7196829 | 2.462738 |
| CCL13 | 0.03250261 | 1 | 51 | −1.7323199 | −0.1022779 | 1.630042 |
| MMP23B | 0.03250261 | 1 | 51 | −1.621664 | −0.240464 | 1.3812 |
| RPS2P32 | 0.03250261 | 1 | 51 | −1.50561864 | −1.492947 | 0.01267164 |
| GUCY1B3 | 0.03250261 | 1 | 51 | −1.168806 | 1.070616 | 2.239422 |
| GPSM1 | 0.03250261 | 1 | 51 | −1.16853 | 2.971897 | 4.140427 |
| EDNRA | 0.03250261 | 1 | 51 | −1.1671337 | 0.8244013 | 1.991535 |
| OXCT2 | 0.03250261 | 1 | 51 | −1.0823979 | −0.9195279 | 0.16287 |
| OLFML2A | 0.03250261 | 1 | 51 | −1.0766121 | 0.9116149 | 1.988227 |
| TMEM191B | 0.03250261 | 1 | 51 | −1.0525314 | −1.716408 | −0.6638766 |
| PLIN2 | 0.03250261 | 1 | 51 | −1.038065 | 4.86427 | 5.902335 |
| NRN1 | 0.03250261 | 1 | 51 | −1.027922 | 3.459609 | 4.487531 |
| MTMR10 | 0.03250261 | 1 | 144 | 1.008314 | 3.450683 | 2.442369 |
| CX3CL1 | 0.03250261 | 1 | 144 | 1.648504 | 4.492289 | 2.843785 |
| OR8G5 | 0.03267458 | 1 | 142 | 2.105656 | −1.216272 | −3.321928 |
| GABRQ | 0.03323542 | 1 | 51 | −1.182948 | −2.850255 | −1.667307 |
| TEX40 | 0.03360089 | 1 | 51 | −1.201872 | −2.560039 | −1.358167 |
| HTR1B | 0.03475686 | 1 | 53 | −1.143047 | −3.321928 | −2.178881 |
| SCGB1D2 | 0.03504475 | 1 | 143 | 3.2930368 | 0.8163498 | −2.476687 |
| MMP1 | 0.03669024 | 1 | 52 | −2.81226115 | 0.05003285 | 2.862294 |
| COL7A1 | 0.03669024 | 1 | 52 | −2.6394667 | −0.9627837 | 1.676683 |
| SLC29A4 | 0.03669024 | 1 | 52 | −2.3860835 | −0.3767905 | 2.009293 |
| ELN | 0.03669024 | 1 | 52 | −2.1185747 | 0.6066223 | 2.725197 |
| TWIST2 | 0.03669024 | 1 | 52 | −2.032366 | 0.266997 | 2.299363 |
| WNT5A | 0.03669024 | 1 | 52 | −1.6836431 | −0.9975236 | 0.6861195 |
| PODNL1 | 0.03669024 | 1 | 52 | −1.6751355 | −0.7440425 | 0.931093 |
| SH2B3 | 0.03669024 | 1 | 52 | −1.445723 | 3.096767 | 4.54249 |
| LAMC3 | 0.03669024 | 1 | 52 | −1.4110061 | −0.4910978 | 0.9199083 |
| CHN1 | 0.03669024 | 1 | 52 | −1.406726 | 2.322756 | 3.729482 |
| COL10A1 | 0.03669024 | 1 | 52 | −1.4049502 | −0.3440932 | 1.060857 |
| KLHL35 | 0.03669024 | 1 | 52 | −1.3989628 | −0.5052434 | 0.8937194 |
| HAS2-AS1 | 0.03669024 | 1 | 52 | −1.384783 | −0.9789268 | 0.4058562 |
| COL5A2 | 0.03669024 | 1 | 52 | −1.212494 | 3.69092 | 4.903414 |
| P4HA2 | 0.03669024 | 1 | 52 | −1.184326 | 3.52849 | 4.712816 |
| VEGFA | 0.03669024 | 1 | 52 | −1.118159 | 2.968408 | 4.086567 |
| DCHS1 | 0.03669024 | 1 | 52 | −1.1129105 | 0.8001565 | 1.913067 |
| WNK3 | 0.03669024 | 1 | 52 | −1.1052376 | −1.760199 | −0.6549614 |
| ANKRD34A | 0.03669024 | 1 | 52 | −1.0949495 | −0.5243797 | 0.5705698 |
| ARHGEF19 | 0.03669024 | 1 | 52 | −1.0538606 | 0.7980464 | 1.851907 |
| CRMP1 | 0.03669024 | 1 | 52 | −1.0479319 | 0.5936071 | 1.641539 |
| CDH13 | 0.03669024 | 1 | 52 | −1.0392877 | 0.9048733 | 1.944161 |
| TMEM229B | 0.03669024 | 1 | 143 | 1.059026 | 3.981469 | 2.922443 |
| LSR | 0.03669024 | 1 | 143 | 1.39405 | 3.011019 | 1.616969 |
| TRIM71 | 0.03805624 | 1 | 53 | −1.083172 | −3.321928 | −2.238756 |
| LINC01194 | 0.03809007 | 1 | 142.5 | 2.948945 | 0.686106 | −2.262839 |
| LY6K | 0.03815142 | 1 | 52 | −1.452124 | −2.628112 | −1.175988 |
| SNORA10 | 0.03866231 | 1 | 55 | −8.010371 | −3.321928 | 4.688443 |
| C14orf132 | 0.0413098 | 1 | 53 | −2.2095922 | −0.2188132 | 1.990779 |
| RCOR2 | 0.0413098 | 1 | 53 | −2.1879867 | −1.366995 | 0.8209917 |
| AIM1 | 0.0413098 | 1 | 53 | −2.0122882 | −0.1329662 | 1.879322 |
| NXN | 0.0413098 | 1 | 53 | −1.672523 | 2.188787 | 3.86131 |
| IL17D | 0.0413098 | 1 | 53 | −1.6467911 | −0.1830481 | 1.463743 |
| ENPP2 | 0.0413098 | 1 | 53 | −1.61638 | 2.391533 | 4.007913 |
| ESM1 | 0.0413098 | 1 | 53 | −1.4638885 | 0.6252845 | 2.089173 |
| ITGBL1 | 0.0413098 | 1 | 53 | −1.4086843 | 0.1496717 | 1.558356 |
| HIST1H4E | 0.0413098 | 1 | 53 | −1.3640448 | −0.7727962 | 0.5912486 |
| ATAD3B | 0.0413098 | 1 | 53 | −1.313104 | 2.305381 | 3.618485 |

-continued

| Gene | Pval | FDR | Stats | diffAvg | avg.R | avg.NR |
|---|---|---|---|---|---|---|
| ACKR3 | 0.0413098 | 1 | 53 | −1.28689 | 1.626091 | 2.912981 |
| TSPAN11 | 0.0413098 | 1 | 53 | −1.2245398 | −0.6786999 | 0.5458399 |
| RGS17 | 0.0413098 | 1 | 53 | −1.2172482 | −1.525781 | −0.3085328 |
| HTRA1 | 0.0413098 | 1 | 53 | −1.186571 | 5.407006 | 6.593577 |
| KCTD17 | 0.0413098 | 1 | 53 | −1.138183 | 2.337583 | 3.475766 |
| DPYSL3 | 0.0413098 | 1 | 53 | −1.136996 | 2.871984 | 4.00898 |
| CYBRD1 | 0.0413098 | 1 | 53 | −1.079204 | 4.105808 | 5.185012 |
| LRRC17 | 0.0413098 | 1 | 53 | −1.0659416 | −0.5605588 | 0.5053828 |
| CHRD | 0.0413098 | 1 | 53 | −1.049737 | −0.3858641 | 0.6638729 |
| IQGAP3 | 0.0413098 | 1 | 53 | −1.005251 | 1.615896 | 2.621147 |
| ZNF677 | 0.0413098 | 1 | 142 | 1.031283 | −1.052097 | −2.08338 |
| F11R | 0.0413098 | 1 | 142 | 1.064247 | 4.240436 | 3.176189 |
| ZSCAN31 | 0.0413098 | 1 | 142 | 1.0830957 | 0.6628754 | −0.4202203 |
| ACCS | 0.0413098 | 1 | 142 | 1.120974 | 2.232232 | 1.111258 |
| RASSF2 | 0.0413098 | 1 | 142 | 1.143772 | 3.863265 | 2.719493 |
| LIMCH1 | 0.0413098 | 1 | 142 | 1.3952446 | 1.747246 | 0.3520014 |
| KIAA1755 | 0.0413098 | 1 | 142 | 1.5795211 | 1.438721 | −0.1408001 |
| GABRP | 0.0413098 | 1 | 142 | 2.019409 | −0.390732 | −2.410141 |
| BLACAT1 | 0.04239169 | 1 | 142 | 1.194081 | −1.409949 | −2.60403 |
| ERVMER34-1 | 0.04256173 | 1 | 53 | −1.555623 | −2.587553 | −1.031903 |
| SCARNA10 | 0.04264681 | 1 | 53 | −2.9003629 | −0.6014439 | 2.298919 |
| OLIG2 | 0.04505756 | 1 | 141.5 | 2.5297866 | 0.4226636 | −2.107123 |
| SNORA68 | 0.04523797 | 1 | 57 | −6.901102 | −3.321928 | 3.579174 |
| COL12A1 | 0.04639385 | 1 | 54 | −2.388013 | 2.500815 | 4.888828 |
| CENPV | 0.04639385 | 1 | 54 | −1.9823031 | −0.3779561 | 1.604347 |
| CTNNA2 | 0.04639385 | 1 | 54 | −1.8967759 | −1.35865 | 0.5381259 |
| B3GALNT1 | 0.04639385 | 1 | 54 | −1.8295176 | 0.5445744 | 2.374092 |
| F2RL1 | 0.04639385 | 1 | 54 | −1.7301182 | −0.3555262 | 1.374592 |
| FMOD | 0.04639385 | 1 | 54 | −1.585349 | 1.898905 | 3.484254 |
| DZIP1 | 0.04639385 | 1 | 54 | −1.5835168 | −0.5269748 | 1.056542 |
| LARP6 | 0.04639385 | 1 | 54 | −1.537145 | 2.656978 | 4.194123 |
| IGFBP6 | 0.04639385 | 1 | 54 | −1.476006 | 2.838161 | 4.314167 |
| LOXL1-AS1 | 0.04639385 | 1 | 54 | −1.4658659 | −1.776565 | −0.3106991 |
| CTHRC1 | 0.04639385 | 1 | 54 | −1.316047 | 5.285025 | 6.601072 |
| GPR156 | 0.04639385 | 1 | 54 | −1.227735 | −2.677969 | −1.450234 |
| OSBP2 | 0.04639385 | 1 | 54 | −1.2104307 | −0.7211755 | 0.4892552 |
| FABP5 | 0.04639385 | 1 | 54 | −1.164904 | 6.224056 | 7.38896 |
| CCL3 | 0.04639385 | 1 | 54 | −1.137411 | 3.315659 | 4.45307 |
| NPNT | 0.04639385 | 1 | 54 | −1.1214106 | −0.5133773 | 0.6080333 |
| ADM2 | 0.04639385 | 1 | 54 | −1.0965337 | −0.2286451 | 0.8678886 |
| TIE1 | 0.04639385 | 1 | 54 | −1.09083 | 1.607529 | 2.698359 |
| NFATC4 | 0.04639385 | 1 | 54 | −1.0099823 | 0.3973977 | 1.40738 |
| TRIM59 | 0.04639385 | 1 | 54 | −1.0076418 | −0.3029646 | 0.7046772 |
| DNAAF3 | 0.04639385 | 1 | 141 | 1.0487162 | −0.1111488 | −1.159865 |
| PCYT1B | 0.04639385 | 1 | 141 | 1.080997 | −1.121661 | −2.202658 |
| PCDHB13 | 0.04639385 | 1 | 141 | 1.0930377 | 0.134355 | −0.9586827 |
| ZNF106 | 0.04639385 | 1 | 141 | 1.141107 | 5.458436 | 4.317329 |
| LOC101928113 | 0.04639385 | 1 | 141 | 1.34368422 | −0.04282978 | −1.386514 |
| ZMYND12 | 0.04639385 | 1 | 141 | 1.3931847 | 0.6938192 | −0.6993655 |
| PCDHGB1 | 0.04639385 | 1 | 141 | 1.86909604 | 0.05941204 | −1.809684 |
| FXYD3 | 0.04639385 | 1 | 141 | 1.923982 | 4.778167 | 2.854185 |
| HAS1 | 0.04749101 | 1 | 54 | −1.552862 | −2.805483 | −1.252621 |
| IGFL4 | 0.05138634 | 1 | 139 | 1.335912 | −1.986016 | −3.321928 |
| NPTX2 | 0.05197312 | 1 | 55 | −3.620849 | −1.48949 | 2.131359 |
| MIR100HG | 0.05197312 | 1 | 55 | −2.6913789 | 0.4448261 | 3.136205 |
| ICAM5 | 0.05197312 | 1 | 55 | −2.482086 | −1.048827 | 1.433259 |
| ADAM19 | 0.05197312 | 1 | 55 | −1.537525 | 1.074636 | 2.612161 |
| KLHL23 | 0.05197312 | 1 | 55 | −1.4564477 | −1.063004 | 0.3934437 |
| SLC1A3 | 0.05197312 | 1 | 55 | −1.451576 | 1.648488 | 3.100064 |
| DNM3OS | 0.05197312 | 1 | 55 | −1.2570921 | −1.028926 | 0.2281661 |
| FLJ41200 | 0.05197312 | 1 | 55 | −1.2553926 | −0.4048812 | 0.8505114 |
| EGFR | 0.05197312 | 1 | 55 | −1.24160814 | −1.221601 | 0.02000714 |
| HS3ST3A1 | 0.05197312 | 1 | 55 | −1.2170139 | −0.7840866 | 0.4329273 |
| HK3 | 0.05197312 | 1 | 55 | −1.151509 | 1.054779 | 2.206288 |
| APLN | 0.05197312 | 1 | 55 | −1.12175923 | 0.05238877 | 1.174148 |
| TRPC1 | 0.05197312 | 1 | 55 | −1.10913567 | −0.01402167 | 1.095114 |
| ADM | 0.05197312 | 1 | 55 | −1.080561 | 2.997596 | 4.078157 |
| EXO1 | 0.05197312 | 1 | 55 | −1.060345 | 1.487651 | 2.547996 |
| NINL | 0.05197312 | 1 | 55 | −1.05218379 | 0.05006421 | 1.102248 |
| CPXM1 | 0.05197312 | 1 | 55 | −1.00079 | 3.125935 | 4.126725 |
| SAMD13 | 0.05197312 | 1 | 140 | 1.0280437 | 1.854403 | 0.8263593 |
| MRGPRX3 | 0.05197312 | 1 | 140 | 1.3189292 | 1.075324 | −0.2436052 |
| LOC100129931 | 0.05269679 | 1 | 140 | 1.436332 | 3.969975 | 2.533643 |
| LKAAEAR1 | 0.05289168 | 1 | 55 | −2.2095869 | −2.59591 | −0.3863231 |
| MCEMP1 | 0.05289168 | 1 | 55 | −1.186268 | −2.197056 | −1.010788 |
| SPATS1 | 0.05289168 | 1 | 140 | 1.6288759 | −0.1507221 | −1.779598 |
| C5orf49 | 0.05298916 | 1 | 55 | −1.145693 | −2.872392 | −1.726699 |

-continued

| Gene | Pval | FDR | Stats | diffAvg | avg.R | avg.NR |
|---|---|---|---|---|---|---|
| LDHC | 0.05474006 | 1 | 55.5 | −1.768901 | −3.102393 | −1.333492 |
| HIST1H3B | 0.05699877 | 1 | 56 | −1.15855 | −2.373731 | −1.215181 |
| IBA57-AS1 | 0.05805748 | 1 | 57.5 | −1.250307 | −3.321928 | −2.071621 |
| CA12 | 0.05808159 | 1 | 56 | −2.5150794 | −0.5301494 | 1.98493 |
| PDGFRL | 0.05808159 | 1 | 56 | −2.46471982 | 0.09356018 | 2.55828 |
| GLT8D2 | 0.05808159 | 1 | 56 | −1.9649491 | 0.2110689 | 2.176018 |
| SNHG18 | 0.05808159 | 1 | 56 | −1.8117334 | −0.5574694 | 1.254264 |
| PCDH18 | 0.05808159 | 1 | 56 | −1.709504566 | −0.00644157 | 1.703063 |
| SFRP2 | 0.05808159 | 1 | 56 | −1.654716 | 3.845806 | 5.500522 |
| SHROOM1 | 0.05808159 | 1 | 56 | −1.5771458 | 0.7608682 | 2.338014 |
| MALL | 0.05808159 | 1 | 56 | −1.5665932 | 0.9406328 | 2.507226 |
| FAP | 0.05808159 | 1 | 56 | −1.450569 | 2.222869 | 3.673438 |
| THBS1 | 0.05808159 | 1 | 56 | −1.442814 | 3.162177 | 4.604991 |
| GLIS2 | 0.05808159 | 1 | 56 | −1.309543 | 1.555782 | 2.865325 |
| FAM19A5 | 0.05808159 | 1 | 56 | −1.2970028 | −1.109401 | 0.1876018 |
| SCUBE3 | 0.05808159 | 1 | 56 | −1.2752722 | −2.226591 | −0.9513188 |
| LINGO1 | 0.05808159 | 1 | 56 | −1.235292 | 2.710302 | 3.945594 |
| DLG4 | 0.05808159 | 1 | 56 | −1.230354 | 1.342566 | 2.57292 |
| CCDC3 | 0.05808159 | 1 | 56 | −1.2107 | 1.022897 | 2.233597 |
| MEX3A | 0.05808159 | 1 | 56 | −1.1630834 | 0.1225316 | 1.285615 |
| CRISPLD2 | 0.05808159 | 1 | 56 | −1.148921 | 1.756473 | 2.905394 |
| DENND2A | 0.05808159 | 1 | 56 | −1.1427194 | −0.4104589 | 0.7322605 |
| CDC20 | 0.05808159 | 1 | 56 | −1.070167 | 3.860819 | 4.930986 |
| DNM1P35 | 0.05808159 | 1 | 56 | −1.023854 | −2.585425 | −1.561571 |
| NAT8L | 0.05808159 | 1 | 139 | 1.001744 | 3.501038 | 2.499294 |
| TUBGCP4 | 0.05808159 | 1 | 139 | 1.009118 | 2.850821 | 1.841703 |
| KIF13A | 0.05808159 | 1 | 139 | 1.035712 | 4.197685 | 3.161973 |
| TP53TG3D | 0.05808159 | 1 | 139 | 1.0587386 | −0.6599084 | −1.718647 |
| PLD4 | 0.05808159 | 1 | 139 | 1.0868947 | 0.9096118 | −0.1772829 |
| ANK2 | 0.05808159 | 1 | 139 | 1.124341 | 2.331634 | 1.207293 |
| SH3D19 | 0.05808159 | 1 | 139 | 1.287465 | 3.090349 | 1.802884 |
| SMPD2 | 0.05808159 | 1 | 139 | 1.494153 | 3.256808 | 1.762655 |
| EPHX2 | 0.05808159 | 1 | 139 | 1.8125841 | 2.218326 | 0.4057419 |
| FCRLA | 0.05808159 | 1 | 139 | 2.160289 | 4.156777 | 1.996488 |
| SHISA2 | 0.05808159 | 1 | 139 | 3.2814476 | 3.87306 | 0.5916124 |
| LEP | 0.05824237 | 1 | 56 | −1.020567 | −3.022582 | −2.002015 |
| CABP7 | 0.05879626 | 1 | 56 | −2.64211617 | −2.662273 | −0.0201568 |
| HSPB2-C11orf52 | 0.06098056 | 1 | 138 | 1.238985 | −2.082943 | −3.321928 |
| SH3GL2 | 0.06205511 | 1 | 138.5 | 1.191994 | −1.638086 | −2.83008 |
| SNORA48 | 0.06385323 | 1 | 58 | −2.139829 | 1.448748 | 3.588577 |
| LOC101928571 | 0.06385323 | 1 | 58 | −1.354678 | −3.321928 | −1.96725 |
| CA9 | 0.0640973 | 1 | 57 | −1.331086 | −2.374316 | −1.04323 |
| SNORA81 | 0.06464904 | 1 | 57 | −3.770112 | 1.467608 | 5.23772 |
| RNF182 | 0.06475139 | 1 | 57 | −2.458649 | −1.096735 | 1.361914 |
| HS3ST2 | 0.06475139 | 1 | 57 | −2.3549694 | −0.7620864 | 1.592883 |
| APLP1 | 0.06475139 | 1 | 57 | −2.294358 | −1.161018 | 1.13334 |
| HRH1 | 0.06475139 | 1 | 57 | −1.9013082 | −0.5468502 | 1.354458 |
| OSR1 | 0.06475139 | 1 | 57 | −1.8021002 | −2.324339 | −0.5222388 |
| LPAR1 | 0.06475139 | 1 | 57 | −1.7073693 | 0.5273807 | 2.23475 |
| PALM2-AKAP2 | 0.06475139 | 1 | 57 | −1.6622693 | −0.2101013 | 1.452168 |
| TUB | 0.06475139 | 1 | 57 | −1.6285029 | −0.9377595 | 0.6907434 |
| WNT11 | 0.06475139 | 1 | 57 | −1.6193462 | −2.023748 | −0.4044018 |
| NOX4 | 0.06475139 | 1 | 57 | −1.5480867 | 0.5459783 | 2.094065 |
| WNT2 | 0.06475139 | 1 | 57 | −1.48954229 | −1.414793 | 0.07474929 |
| WIPF1 | 0.06475139 | 1 | 57 | −1.467869 | 3.834008 | 5.301877 |
| MME | 0.06475139 | 1 | 57 | −1.439291 | 1.325004 | 2.764295 |
| CPT1C | 0.06475139 | 1 | 57 | −1.3986051 | −0.3987818 | 0.9998233 |
| EXOC3L2 | 0.06475139 | 1 | 57 | −1.3139647 | 0.8426973 | 2.156662 |
| BEND6 | 0.06475139 | 1 | 57 | −1.2886909 | −1.57926 | −0.2905691 |
| FBXL13 | 0.06475139 | 1 | 57 | −1.2407868 | −1.693182 | −0.4523952 |
| COL3A1 | 0.06475139 | 1 | 57 | −1.220618 | 7.475385 | 8.696003 |
| ECE1 | 0.06475139 | 1 | 57 | −1.215129 | 3.496801 | 4.71193 |
| DACT3 | 0.06475139 | 1 | 57 | −1.181962 | 1.227513 | 2.409475 |
| HECW2 | 0.06475139 | 1 | 57 | −1.1802747 | −0.6469207 | 0.533354 |
| C19orf83 | 0.06475139 | 1 | 57 | −1.1730422 | −0.5409462 | 0.632096 |
| TLDC2 | 0.06475139 | 1 | 57 | −1.1708766 | −1.521434 | −0.3505574 |
| TNFRSF6B | 0.06475139 | 1 | 57 | −1.134778 | 1.95564 | 3.090418 |
| LOX | 0.06475139 | 1 | 57 | −1.121106 | 1.281455 | 2.402561 |
| PPFIA2 | 0.06475139 | 1 | 57 | −1.11398 | −2.869431 | −1.755451 |
| RTEL1 | 0.06475139 | 1 | 57 | −1.084195 | 1.711319 | 2.795514 |
| GNB3 | 0.06475139 | 1 | 57 | −1.0710466 | −1.582253 | −0.5112064 |
| TNS1 | 0.06475139 | 1 | 57 | −1.044708 | 2.851845 | 3.896553 |
| G0S2 | 0.06475139 | 1 | 57 | −1.034188 | 2.548904 | 3.583092 |
| ABCC11 | 0.06475139 | 1 | 138 | 1.07104 | −1.506398 | −2.577438 |
| RPS12 | 0.06475139 | 1 | 138 | 1.12826 | 11.91852 | 10.79026 |

-continued

| Gene | Pval | FDR | Stats | diffAvg | avg.R | avg.NR |
|---|---|---|---|---|---|---|
| ADPGK-AS1 | 0.06475139 | 1 | 138 | 1.2166381 | −0.3922649 | −1.608903 |
| GNG7 | 0.06475139 | 1 | 138 | 1.243368 | 4.567214 | 3.323846 |
| TMPRSS5 | 0.06475139 | 1 | 138 | 1.2864986 | 0.7449877 | −0.5415109 |
| ASB9 | 0.06475139 | 1 | 138 | 1.329036 | 3.454834 | 2.125798 |
| CCL17 | 0.06475139 | 1 | 138 | 1.539527 | 0.6213275 | −0.9181995 |
| LINC00920 | 0.06475139 | 1 | 138 | 2.033027 | 4.095135 | 2.062108 |
| LINC00313 | 0.06506976 | 1 | 59 | −1.233836 | −3.321928 | −2.088092 |
| GNGT1 | 0.06506976 | 1 | 136 | 1.183131 | −2.138797 | −3.321928 |
| FBLL1 | 0.06523808 | 1 | 57 | −1.22896018 | −0.09073918 | 1.138221 |
| MIXL1 | 0.06534859 | 1 | 57 | −1.044112 | −2.491249 | −1.447137 |
| PGM5-AS1 | 0.0659831 | 1 | 58 | −1.070918 | −3.321928 | −2.25101 |
| ETNPPL | 0.06749574 | 1 | 137.5 | 2.1307339 | −0.6923791 | −2.823113 |
| HIST1H2BB | 0.06851559 | 1 | 60 | −1.049268 | −3.321928 | −2.27266 |
| CHRM1 | 0.06878488 | 1 | 137.5 | 1.6511538 | −0.7677052 | −2.418859 |
| WDR63 | 0.06878488 | 1 | 137.5 | 2.146965 | −0.203281 | −2.350264 |
| LINC01266 | 0.07162641 | 1 | 137 | 1.137445 | −1.919176 | −3.056621 |
| RNU6ATAC | 0.07201681 | 1 | 58 | −1.085782 | 4.190931 | 5.276713 |
| CXorf65 | 0.07201681 | 1 | 137 | 1.5718145 | −0.2449595 | −1.816774 |
| EPHA3 | 0.07201705 | 1 | 58 | −2.2487947 | −0.9405907 | 1.308204 |
| CH25H | 0.07201705 | 1 | 58 | −2.0436863 | −0.9321273 | 1.111559 |
| SGIP1 | 0.07201705 | 1 | 58 | −1.89277123 | −1.921724 | −0.0289528 |
| MMP3 | 0.07201705 | 1 | 58 | −1.88931445 | −1.869493 | 0.01982145 |
| PTGDS | 0.07201705 | 1 | 58 | −1.879402 | 4.030274 | 5.909676 |
| APBA2 | 0.07201705 | 1 | 58 | −1.8234035 | −0.3594485 | 1.463955 |
| THBS2 | 0.07201705 | 1 | 58 | −1.793561 | 3.121489 | 4.91505 |
| CAMK1G | 0.07201705 | 1 | 58 | −1.7338523 | −1.094546 | 0.6393063 |
| SERTAD4 | 0.07201705 | 1 | 58 | −1.6041789 | −1.864444 | −0.2602651 |
| FAM13C | 0.07201705 | 1 | 58 | −1.5756219 | −0.8693168 | 0.7063051 |
| REM1 | 0.07201705 | 1 | 58 | −1.5614432 | −0.8115915 | 0.7498517 |
| PIWIL4 | 0.07201705 | 1 | 58 | −1.3250848 | −1.493835 | −0.1687502 |
| A4GALT | 0.07201705 | 1 | 58 | −1.3243055 | 0.9352485 | 2.259554 |
| DLX1 | 0.07201705 | 1 | 58 | −1.2936086 | 0.1319424 | 1.425551 |
| SOD3 | 0.07201705 | 1 | 58 | −1.249651 | 3.281525 | 4.531176 |
| LPHN2 | 0.07201705 | 1 | 58 | −1.2483911 | 0.5027939 | 1.751185 |
| NID2 | 0.07201705 | 1 | 58 | −1.189489 | 1.425892 | 2.615381 |
| PLCE1 | 0.07201705 | 1 | 58 | −1.1342158 | −1.245328 | −0.1111122 |
| PLXDC1 | 0.07201705 | 1 | 58 | −1.1193983 | 0.6566977 | 1.776096 |
| VSTM4 | 0.07201705 | 1 | 58 | −1.08231529 | −0.08148629 | 1.000829 |
| ARNTL2 | 0.07201705 | 1 | 58 | −1.06412524 | −0.9644254 | 0.09969984 |
| FPR2 | 0.07201705 | 1 | 58 | −1.0609539 | −1.175556 | −0.1146021 |
| ICAM2 | 0.07201705 | 1 | 58 | −1.00608 | 2.902156 | 3.908236 |
| SNAI1 | 0.07201705 | 1 | 58 | −1.002535 | 1.109835 | 2.11237 |
| TMEM117 | 0.07201705 | 1 | 137 | 1.069717 | 3.259832 | 2.190115 |
| KIAA1161 | 0.07201705 | 1 | 137 | 1.06991159 | 1.128208 | 0.05829641 |
| VAMP8 | 0.07201705 | 1 | 137 | 1.076123 | 6.929164 | 5.853041 |
| RASGRP1 | 0.07201705 | 1 | 137 | 1.1293496 | 0.2614105 | −0.8679391 |
| GYG2 | 0.07201705 | 1 | 137 | 1.22961 | 4.6579 | 3.42829 |
| ITGA3 | 0.07201705 | 1 | 137 | 1.670273 | 5.742233 | 4.07196 |
| C1orf226 | 0.07201705 | 1 | 137 | 1.9189112 | 0.7410182 | −1.177893 |
| LOC400644 | 0.07201705 | 1 | 137 | 3.2918132 | 3.723864 | 0.4320508 |
| HERC2P4 | 0.07236828 | 1 | 137 | 1.7111815 | −0.6455185 | −2.3567 |
| BDKRB1 | 0.07610311 | 1 | 58.5 | −1.6975456 | −2.104341 | −0.4067954 |
| GNG8 | 0.07616672 | 1 | 64 | −1.74085 | −3.321928 | −1.581078 |
| SNORA24 | 0.07813697 | 1 | 62.5 | −7.93121 | −3.321928 | 4.609282 |
| DGUOK-AS1 | 0.07920913 | 1 | 59 | −1.1154189 | −1.289062 | −0.1736431 |
| PAGE5 | 0.07920913 | 1 | 136 | 1.999152 | −0.665466 | −2.664618 |
| HEY1 | 0.07991109 | 1 | 59 | −2.192591 | 3.080934 | 5.273525 |
| LPAR3 | 0.07991109 | 1 | 59 | −2.0615078 | −2.364104 | −0.3025962 |
| CYTL1 | 0.07991109 | 1 | 59 | −1.9661553 | −0.1434923 | 1.822663 |
| ITGA11 | 0.07991109 | 1 | 59 | −1.9284091 | −0.2168501 | 1.711559 |
| SERP2 | 0.07991109 | 1 | 59 | −1.9074767 | −0.6319927 | 1.275484 |
| SERTAD4-AS1 | 0.07991109 | 1 | 59 | −1.7799747 | −0.9284515 | 0.8515232 |
| HOXA10 | 0.07991109 | 1 | 59 | −1.757677 | 0.660664 | 2.418341 |
| HOXB2 | 0.07991109 | 1 | 59 | −1.749016 | 2.248014 | 3.99703 |
| DKK2 | 0.07991109 | 1 | 59 | −1.7266729 | −1.367326 | 0.3593469 |
| CACNA2D1 | 0.07991109 | 1 | 59 | −1.7131162 | −1.17894 | 0.5341762 |
| PIEZO2 | 0.07991109 | 1 | 59 | −1.5553771 | −0.5367291 | 1.018648 |
| TRABD2A | 0.07991109 | 1 | 59 | −1.5297367 | −1.225138 | 0.3045987 |
| ME3 | 0.07991109 | 1 | 59 | −1.5257831 | −0.6258341 | 0.899949 |
| SLC35G2 | 0.07991109 | 1 | 59 | −1.51780198 | 0.04668802 | 1.56449 |
| PFKFB4 | 0.07991109 | 1 | 59 | −1.464076 | 1.526287 | 2.990363 |
| NTM | 0.07991109 | 1 | 59 | −1.3766436 | 0.0461844 | 1.422828 |
| PCOLCE-AS1 | 0.07991109 | 1 | 59 | −1.348895 | −2.688414 | −1.339519 |
| RAB42 | 0.07991109 | 1 | 59 | −1.2648636 | 0.7846924 | 2.049556 |
| LIMD1 | 0.07991109 | 1 | 59 | −1.19859 | 1.752412 | 2.951002 |
| TMSB15A | 0.07991109 | 1 | 59 | −1.173387 | 1.096397 | 2.269784 |

-continued

| Gene | Pval | FDR | Stats | diffAvg | avg.R | avg.NR |
|---|---|---|---|---|---|---|
| PERM1 | 0.07991109 | 1 | 59 | −1.1663028 | −1.818839 | −0.6525362 |
| PDGFRA | 0.07991109 | 1 | 59 | −1.139858 | 1.358616 | 2.498474 |
| GTSE1 | 0.07991109 | 1 | 59 | −1.117235 | 2.36028 | 3.477515 |
| PODXL | 0.07991109 | 1 | 59 | −1.047478 | 2.237362 | 3.28484 |
| DCN | 0.07991109 | 1 | 59 | −1.043292 | 5.966609 | 7.009901 |
| NR3C2 | 0.07991109 | 1 | 136 | 1.1052036 | −0.5197514 | −1.624955 |
| GLUD2 | 0.07991109 | 1 | 136 | 1.1184848 | 0.8441928 | −0.274292 |
| MFSD6 | 0.07991109 | 1 | 136 | 1.153648 | 3.563463 | 2.409815 |
| ZNF626 | 0.07991109 | 1 | 136 | 1.2185378 | 1.999356 | 0.7808182 |
| LRRC75A-AS1 | 0.07991109 | 1 | 136 | 1.233348 | 9.632714 | 8.399366 |
| LINC01212 | 0.07991109 | 1 | 136 | 1.4177327 | −0.1266553 | −1.544388 |
| VTN | 0.07991109 | 1 | 136 | 1.6521657 | 0.4243417 | −1.227824 |
| RAET1E-AS1 | 0.0799937 | 1 | 136 | 1.1147811 | 0.1376275 | −0.9771536 |
| PTENP1-AS | 0.0805186 | 1 | 61 | −1.469631 | −3.321928 | −1.852297 |
| CST2 | 0.08260212 | 1 | 59.5 | −1.4534018 | −2.423159 | −0.9697572 |
| GOLT1A | 0.08307547 | 1 | 135 | 1.709569 | −1.061409 | −2.770978 |
| SYTL5 | 0.08366261 | 1 | 59.5 | −1.6295506 | −2.31139 | −0.6818394 |
| UNC5B-AS1 | 0.0841086 | 1 | 61 | −1.612624 | −3.321928 | −1.709304 |
| LOC101928837 | 0.08743215 | 1 | 60 | −1.5031697 | −1.385865 | 0.1173047 |
| FAM131C | 0.08743215 | 1 | 60 | −1.251103 | −2.846797 | −1.595694 |
| TMEM200C | 0.08812891 | 1 | 60 | −1.367226 | −1.81183 | −0.444604 |
| RORB | 0.08812891 | 1 | 60 | −1.17606 | −2.835436 | −1.659376 |
| LINC01239 | 0.08812891 | 1 | 60 | −1.071185 | −2.944194 | −1.873009 |
| WDR72 | 0.08812891 | 1 | 135 | 1.1301 | −1.454678 | −2.584778 |
| ANGPTL7 | 0.08812891 | 1 | 135 | 1.9281366 | −0.4333904 | −2.361527 |
| FAM101A | 0.08846856 | 1 | 60 | −2.9752643 | −2.418982 | 0.5562823 |
| HOXB9 | 0.08846856 | 1 | 60 | −2.4640244 | −0.9920094 | 1.472015 |
| NRXN2 | 0.08846856 | 1 | 60 | −1.9499113 | −0.2955583 | 1.654353 |
| ANPEP | 0.08846856 | 1 | 60 | −1.864682 | 1.243456 | 3.108138 |
| ITPKA | 0.08846856 | 1 | 60 | −1.7115608 | −1.256669 | 0.4548918 |
| ASS1 | 0.08846856 | 1 | 60 | −1.519369 | 1.411339 | 2.930708 |
| GPR162 | 0.08846856 | 1 | 60 | −1.5100042 | −0.5135142 | 0.99649 |
| KCNG1 | 0.08846856 | 1 | 60 | −1.4744683 | −0.3837063 | 1.090762 |
| CPVL | 0.08846856 | 1 | 60 | −1.442219 | 4.5933 | 6.035519 |
| PDLIM1 | 0.08846856 | 1 | 60 | −1.385467 | 3.860983 | 5.24645 |
| PNPLA3 | 0.08846856 | 1 | 60 | −1.2542662 | −0.8344199 | 0.4198463 |
| RGS11 | 0.08846856 | 1 | 60 | −1.2389998 | −1.910076 | −0.6710762 |
| RGS4 | 0.08846856 | 1 | 60 | −1.2094431 | −0.747485 | 0.4619581 |
| CALHM2 | 0.08846856 | 1 | 60 | −1.200965 | 2.570213 | 3.771178 |
| FAM64A | 0.08846856 | 1 | 60 | −1.150179 | 2.153844 | 3.304023 |
| INMT | 0.08846856 | 1 | 60 | −1.093546 | 0.312201 | 1.405747 |
| CDH11 | 0.08846856 | 1 | 60 | −1.071131 | 2.623036 | 3.694167 |
| LIMD1-AS1 | 0.08846856 | 1 | 60 | −1.062219 | 2.242223 | 3.304442 |
| PSMB8 | 0.08846856 | 1 | 135 | 1.000832 | 3.40133 | 2.400498 |
| UGCG | 0.08846856 | 1 | 135 | 1.056632 | 5.006554 | 3.949922 |
| MYEF2 | 0.08846856 | 1 | 135 | 1.302493 | 4.236313 | 2.93382 |
| ANKRD20A12P | 0.08846856 | 1 | 135 | 1.3615798 | 2.121068 | 0.7594882 |
| SNHG5 | 0.08846856 | 1 | 135 | 1.383093 | 9.051138 | 7.668045 |
| IRX6 | 0.08846856 | 1 | 135 | 1.5010209 | 1.891507 | 0.3904861 |
| SNHG8 | 0.08846856 | 1 | 135 | 1.744982 | 8.447397 | 6.702415 |
| HLA-A | 0.08846856 | 1 | 135 | 1.981057 | 7.422628 | 5.441571 |
| ABCC2 | 0.08846856 | 1 | 135 | 2.4926895 | 2.115796 | −0.3768935 |
| PPP1R14C | 0.08846856 | 1 | 135 | 2.5369517 | 0.8727027 | −1.664249 |
| DKFZP434L187 | 0.08929316 | 1 | 62 | −1.124272 | −3.321928 | −2.197656 |
| LOC284344 | 0.08967541 | 1 | 134 | 1.919843 | −1.144627 | −3.06447 |
| KLK4 | 0.09174328 | 1 | 61 | −1.311161 | −2.764102 | −1.452941 |
| SCARNA6 | 0.09308432 | 1 | 62 | −3.6413841 | −3.321928 | 0.3194561 |
| LOC283352 | 0.09564329 | 1 | 134 | 4.732925 | 3.141143 | −1.591782 |
| RCVRN | 0.09706325 | 1 | 61 | −1.021085 | −2.795706 | −1.774621 |
| PLCB4 | 0.09772118 | 1 | 61 | −2.621658 | −1.558763 | 1.062895 |
| RSPH9 | 0.09772118 | 1 | 61 | −1.90907156 | −1.973983 | −0.0649114 |
| PCOLCE | 0.09772118 | 1 | 61 | −1.890763 | 5.163543 | 7.054306 |
| TBXA2R | 0.09772118 | 1 | 61 | −1.7380936 | 0.2973364 | 2.03543 |
| IGDCC4 | 0.09772118 | 1 | 61 | −1.7100766 | −0.6695276 | 1.040549 |
| NOVA1 | 0.09772118 | 1 | 61 | −1.68105793 | −1.761216 | −0.0801581 |
| TUBA8 | 0.09772118 | 1 | 61 | −1.6658002 | −0.4218052 | 1.243995 |
| PCSK6 | 0.09772118 | 1 | 61 | −1.5703462 | −0.2249672 | 1.345379 |
| MRGPRF | 0.09772118 | 1 | 61 | −1.504914 | −0.516582 | 0.988332 |
| TMEM163 | 0.09772118 | 1 | 61 | −1.4877311 | −0.3104351 | 1.177296 |
| CTBP1-AS | 0.09772118 | 1 | 61 | −1.470821 | −0.648919 | 0.821902 |
| CXCL5 | 0.09772118 | 1 | 61 | −1.4650856 | −2.303461 | −0.8383754 |
| ACOX2 | 0.09772118 | 1 | 61 | −1.4429556 | −1.222019 | 0.2209366 |
| MAP6D1 | 0.09772118 | 1 | 61 | −1.4158326 | 0.1082314 | 1.524064 |
| MSI1 | 0.09772118 | 1 | 61 | −1.321138 | −2.642031 | −1.320893 |
| LTBP1 | 0.09772118 | 1 | 61 | −1.291908 | 1.98646 | 3.278368 |
| MMP9 | 0.09772118 | 1 | 61 | −1.265313 | 3.960799 | 5.226112 |

-continued

| Gene | Pval | FDR | Stats | diffAvg | avg.R | avg.NR |
|---|---|---|---|---|---|---|
| RADIL | 0.09772118 | 1 | 61 | −1.2361487 | −2.150289 | −0.9141403 |
| TRPM3 | 0.09772118 | 1 | 61 | −1.22613 | −2.86917 | −1.64304 |
| RIMS2 | 0.09772118 | 1 | 61 | −1.18251 | −2.349026 | −1.166516 |
| UCHL1 | 0.09772118 | 1 | 61 | −1.1725838 | 0.5262792 | 1.698863 |
| GPR4 | 0.09772118 | 1 | 61 | −1.140973 | 1.10748 | 2.248453 |
| SPATA18 | 0.09772118 | 1 | 61 | −1.0879963 | −1.864423 | −0.7764267 |
| SNTA1 | 0.09772118 | 1 | 61 | −1.06875 | 2.871713 | 3.940463 |
| HOXB-AS1 | 0.09772118 | 1 | 61 | −1.05469193 | −1.09566 | −0.0409681 |
| FAM133DP | 0.09772118 | 1 | 61 | −1.0510606 | −0.3765105 | 0.6745501 |
| TNFRSF25 | 0.09772118 | 1 | 61 | −1.0223879 | 0.4107481 | 1.433136 |
| FILIP1 | 0.09772118 | 1 | 61 | −1.0069617 | −1.554049 | −0.5470873 |
| MN1 | 0.09772118 | 1 | 61 | −1.002883 | −1.223709 | −0.220826 |
| KBTBD4 | 0.09772118 | 1 | 134 | 1.001948 | 3.524064 | 2.522116 |
| SPTBN2 | 0.09772118 | 1 | 134 | 1.448088 | 2.418522 | 0.970434 |
| CLECL1 | 0.09772118 | 1 | 134 | 1.8788903 | 0.5635243 | −1.315366 |
| KRT19 | 0.09803674 | 1 | 61.5 | −1.316096 | −3.001736 | −1.68564 |
| BAGE | 0.09882205 | 1 | 132 | 1.721211 | −1.600717 | −3.321928 |
| HIST1H4B | 0.09894899 | 1 | 62 | −1.57329 | −3.321928 | −1.748638 |

Table 2, Related to FIG. 2

| Geneset | Pval | FDR | Stats | diffAvg |
|---|---|---|---|---|
| ROY_WOUND_BLOOD_VESSEL_UP | 0.000597581 | 0.048404053 | 3.905694 | 0.2130077 |
| MAPKi_INDUCED_EMT | 0.001075721 | 0.08605768 | 3.678224 | 0.2757732 |
| INGRAM_SHH_TARGETS_DN | 0.001121353 | 0.088586887 | 3.662046 | 0.1008678 |
| WESTON_VEGFA_TARGETS_12HR | 0.00141856 | 0.11064768 | 3.570197 | 0.1424745 |
| LEF1_UP.V1_UP | 0.001474676 | 0.113550052 | 3.55499 | 0.1330981 |
| MAPKi_INDUCED_ANGIOGENESIS | 0.002110708 | 0.160413808 | 3.413672 | 0.3170467 |
| WONG_ENDMETRIUM_CANCER_DN | 0.003179412 | 0.2384559 | 3.250311 | 0.1297546 |
| CHARAFE_BREAST_CANCER_BASAL_VS_MESENCHYMAL_DN | 0.003232173 | 0.239180802 | 3.2437 | 0.1501623 |
| POST_OP_WOUNDHEALING | 0.003677965 | 0.268491445 | 3.191661 | 0.1302611 |
| MAPKR_REG_CELL_PROLIF_UP | 0.003748309 | 0.269878248 | 3.184009 | 0.1692385 |
| LOPES_METHYLATED_IN_COLON_CANCER_DN | 0.004017485 | 0.285241435 | 3.155949 | 0.1133278 |
| LIM_MAMMARY_STEM_CELL_UP | 0.004161588 | 0.29131116 | 3.141662 | 0.1287526 |
| JAEGER_METASTASIS_UP | 0.004333241 | 0.298993629 | 3.125249 | 0.1275275 |
| YAO_TEMPORAL_RESPONSE_TO_PROGESTERONE_CLUSTER_16 | 0.004787973 | 0.325582164 | 3.084609 | 0.1479937 |
| ANASTASSIOU_CANCER_MESENCHYMAL_TRANSITION_SIGNATURE | 0.004840233 | 0.325582164 | 3.080178 | 0.1827605 |
| POOLA_INVASIVE_BREAST_CANCER_UP | 0.005010394 | 0.330686004 | 3.06606 | 0.1508535 |
| WESTON_VEGFA_TARGETS_6HR | 0.005244851 | 0.340915315 | 3.047341 | 0.1515207 |
| VALK_AML_WITH_CEBPA | 0.00533315 | 0.3413216 | 3.040497 | 0.1067198 |
| SATO_SILENCED_BY_DEACETYLATION_IN_PANCREATIC_CANCER | 0.005563287 | 0.350487081 | 3.023158 | 0.1152619 |
| GU_PDEF_TARGETS_UP | 0.0059488 | 0.3688256 | 2.995589 | 0.1321217 |
| LU_TUMOR_VASCULATURE_UP | 0.006402595 | 0.390558295 | 2.965241 | 0.1544635 |
| SWEET_KRAS_TARGETS_UP | 0.006751649 | 0.40509894 | 2.943259 | 0.1057307 |
| PETROVA_PROX1_TARGETS_DN | 0.007586811 | 0.447621849 | 2.894762 | 0.1154549 |
| CROONQUIST_STROMAL_STIMULATION_UP | 0.007623001 | 0.447621849 | 2.892777 | 0.1195866 |
| VECCHI_GASTRIC_CANCER_ADVANCED_VS_EARLY_UP | 0.007719889 | 0.447621849 | 2.887506 | 0.132689 |
| VALK_AML_CLUSTER_9 | 0.0077802 | 0.447621849 | 2.884256 | 0.1216417 |
| LINDGREN_BLADDER_CANCER_HIGH_RECURRENCE | 0.008192422 | 0.45058321 | 2.862666 | 0.1339631 |
| ROZANOV_MMP14_TARGETS_SUBSET | 0.009308746 | 0.502672284 | 2.808984 | 0.1742907 |
| VANHARANTA_UTERINE_FIBROID_UP | 0.009859341 | 0.522545073 | 2.78471 | 0.1289315 |
| JECHLINGER_EPITHELIAL_TO_MESENCHYMAL_TRANSITION_UP | 0.01204705 | 0.6264466 | 2.699417 | 0.1132021 |
| GILDEA_METASTASIS | 0.01210953 | 0.6264466 | 2.697202 | 0.1459564 |
| DTPP_REG_CELL_PROLIF_UP | 0.01239673 | 0.6264466 | 2.687154 | 0.131568 |
| DTPP_BLOOD_VESS_DEVEL_UP | 0.0128178 | 0.6280722 | 2.67281 | 0.2016696 |
| RIGGI_EWING_SARCOMA_PROGENITOR_DN | 0.01350913 | 0.64843824 | 2.650189 | 0.1363939 |
| LU_TUMOR_ANGIOGENESIS_UP | 0.01420748 | 0.66775156 | 2.628412 | 0.1379888 |
| NAKAMURA_ADIPOGENESIS_EARLY_DN | 0.01461281 | 0.68138926 | 2.610328 | 0.1186943 |
| TSAI_RESPONSE_TO_RADIATION_THERAPY | 0.01484236 | 0.68138926 | 2.609463 | 0.1827715 |
| BMI1_DN_MEL18_DN.V1_UP | 0.01508883 | 0.68138926 | 2.602311 | 0.1223808 |
| LIM_MAMMARY_LUMINAL_MATURE_DN | 0.0159022 | 0.6837946 | 2.579454 | 0.1011386 |
| WILCOX_PRESPONSE_TO_ROGESTERONE_DN | 0.01684531 | 0.70752402 | 2.554262 | 0.1023573 |
| PETROVA_PROX1_TARGETS_UP | 0.01697682 | 0.70752402 | 2.550869 | 0.1434951 |
| CLASPER_LYMPHATIC_VESSELS_DURING_METASTASIS_DN | 0.01826444 | 0.7305776 | 2.518752 | 0.2849756 |
| MS_RESP_TO_WOUNDING_UP_IN_MAPKi_aPDL1_NR | 0.0221768 | 0.8648952 | 2.432625 | 0.1329788 |
| DTP_BLOOD_VESS_DEVEL_UP | 0.02283232 | 0.86762816 | 2.419585 | 0.1396169 |
| EP_BLOOD_VESS_DEVEL_DN_IN_R | 0.02352731 | 0.87051047 | 2.406131 | 0.2440904 |
| MEL18_DN.V1_UP | 0.02418926 | 0.87081336 | 2.393651 | 0.1034612 |
| LIEN_BREAST_CARCINOMA_METAPLASTIC | 0.0243337 | 0.87081336 | 2.39097 | 0.128597 |
| JACKSON_DNMT1_TARGETS_DN | 0.02501178 | 0.87081336 | 2.378573 | 0.1199879 |
| STEGER_ADIPOGENESIS_DN | 0.0258724 | 0.87081336 | 2.363276 | 0.1076001 |
| HOEK_INVASIVE_SIG | 0.02629071 | 0.87081336 | 2.356008 | 0.1679166 |
| NAKAYAMA_SOFT_TISSUE_TUMORS_PCA2_UP | 0.02657608 | 0.87081336 | 2.351111 | 0.110416 |

| | | | | |
|---|---|---|---|---|
| DTPP_CELL_ADHESION_UP | 0.02674815 | 0.87081336 | 2.348181 | 0.1140066 |
| PLASARI_TGFB1_TARGETS_10HR_UP | 0.02773166 | 0.87081336 | 2.331757 | 0.1013366 |
| ZWANG_CLASS_2_TRANSIENTLY_INDUCED_BY_EGF | 0.02892436 | 0.87081336 | 2.312538 | 0.1078084 |
| HARRIS_HYPOXIA | 0.02942447 | 0.87081336 | 2.304693 | 0.1085055 |
| TURASHVILI_BREAST_LOBULAR_CARCINOMA_VS_DUCTAL_NORMAL_UP | 0.03214257 | 0.87081336 | 2.264067 | 0.1001621 |
| WEINMANN_ADAPTATION_TO_HYPOXIA_DN | 0.03227399 | 0.87081336 | 2.262183 | 0.166015 |
| PLX2D_CELL_ADHESION_UP | 0.03617941 | 0.87081336 | 2.209139 | 0.1016812 |
| NAKAMURA_CANCER_MICROENVIRONMENT_UP | 0.03759705 | 0.87081336 | 2.191158 | 0.1243669 |
| WILLIAMS_ESR1_TARGETS_UP | 0.03766434 | 0.87081336 | 2.19032 | 0.1070796 |
| EP_RESP_TO_WOUNDING_DN_IN_R | 0.04147386 | 0.87095106 | 2.144931 | 0.1832484 |
| DAVICIONI_TARGETS_OF_PAX_FOXO1_FUSIONS_DN | 0.04391986 | 0.8783972 | 2.11772 | 0.1050117 |
| CHNG_MULTIPLE_MYELOMA_HYPERPLOID_UP | 0.04501908 | 0.8783972 | -2.105931 | -0.102919 |
| KIM_GLIS2_TARGETS_UP | 0.0546924 | 0.9844632 | 2.01197 | 0.1322153 |
| PH_BLOOD_VESS_DEVEL_DN_IN_R | 0.05502852 | 0.9844632 | 2.008978 | 0.1606355 |
| VALK_AML_CLUSTER_13 | 0.05648656 | 0.9844632 | 1.996184 | 0.1132569 |
| HARRIS_BRAIN_CANCER_PROGENITORS | 0.06072352 | 0.9844632 | 1.960588 | 0.1236691 |
| PH_RESP_TO_WOUNDING_DN_IN_R | 0.07399112 | 1 | 1.861669 | 0.1079071 |
| WANG_BARRETTS_ESOPHAGUS_UP | 0.08072763 | 1 | 1.81722 | 0.1085087 |
| BERENJENO_TRANSFORMED_BY_RHOA_REVERSIBLY_DN | 0.08885657 | 1 | 1.767643 | 0.1186764 |
| DTPP_RESP_TO_WOUNDING_UP | 0.09435173 | 1 | 1.73628 | 0.1592947 |
| BACOLOD_RESISTANCE_TO_ALKYLATING_AGENTS_UP | 0.09491353 | 1 | 1.733161 | 0.1158654 |

| Geneset | avg. NR | avg. R |
|---|---|---|
| ROY_WOUND_BLOOD_VESSEL_UP | 0.2721261 | 0.05911845 |
| MAPKi_INDUCED_EMT | 0.3662067 | 0.09043351 |
| INGRAM_SHH_TARGETS_DN | 0.1363125 | 0.0354447 |
| WESTON_VEGFA_TARGETS_12HR | 0.293405 | 0.1509305 |
| LEF1_UP.V1_UP | 0.01377793 | -0.1193202 |
| MAPKi_INDUCED_ANGIOGENESIS | 0.1408456 | -0.1762011 |
| WONG_ENDMETRIUM_CANCER_DN | -0.1687945 | -0.2985491 |
| CHARAFE_BREAST_CANCER_BASAL_VS_MESENCHYMAL_DN | 0.3409889 | 0.1908266 |
| POST_OP_WOUNDHEALING | -0.1355108 | -0.2657719 |
| MAPKR_REG_CELL_PROLIF_UP | 0.03565736 | -0.1335811 |
| LOPES_METHYLATED_IN_COLON_CANCER_DN | 0.1336541 | 0.0203263 |
| LIM_MAMMARY_STEM_CELL_UP | 0.2320358 | 0.1032832 |
| JAEGER_METASTASIS_UP | 0.3233281 | 0.1958006 |
| YAO_TEMPORAL_RESPONSE_TO_PROGESTERONE_CLUSTER_16 | 0.2849142 | 0.1369202 |
| ANASTASSIOU_CANCER_MESENCHYMAL_TRANSITION_SIGNATURE | 0.1454204 | -0.03733006 |
| POOLA_INVASIVE_BREAST_CANCER_UP | 0.1497 | -0.00115353 |
| WESTON_VEGFA_TARGETS_6HR | 0.1874614 | 0.03594071 |
| VALK_AML_WITH_CEBPA | 0.1902674 | 0.08349908 |
| SATO_SILENCED_BY_DEACETYLATION_IN_PANCREATIC_CANCER | 0.1978743 | 0.08261245 |
| GU_PDEF_TARGETS_UP | 0.4230377 | 0.290916 |
| LU_TUMOR_VASCULATURE_UP | 0.2250848 | 0.0706213 |
| SWEET_KRAS_TARGETS_UP | 0.4503997 | 0.344669 |
| PETROVA_PROX1_TARGETS_DN | 0.3937612 | 0.2783063 |
| CROONQUIST_STROMAL_STIMULATION_UP | 0.5146544 | 0.3950678 |
| VECCHI_GASTRIC_CANCER_ADVANCED_VS_EARLY_UP | 0.2559903 | 0.1233013 |
| VALK_AML_CLUSTER_9 | 0.1084409 | -0.01320082 |
| LINDGREN_BLADDER_CANCER_HIGH_RECURRENCE | 0.3220292 | 0.1880661 |
| ROZANOV_MMP14_TARGETS_SUBSET | 0.4381816 | 0.2638909 |
| VANHARANTA_UTERINE_FIBROID_UP | 0.3084008 | 0.1794693 |
| JECHLINGER_EPITHELIAL_TO_MESENCHYMAL_TRANSITION_UP | 0.2357906 | 0.1225885 |
| GILDEA_METASTASIS | 0.3505573 | 0.2046009 |
| DTPP_REG_CELL_PROLIF_UP | 0.1444371 | 0.01286914 |
| DTPP_BLOOD_VESS_DEVEL_UP | 0.4122111 | 0.2105415 |
| RIGGI_EWING_SARCOMA_PROGENITOR_DN | 0.1837516 | 0.04735774 |
| LU_TUMOR_ANGIOGENESIS_UP | 0.3857342 | 0.2477454 |
| NAKAMURA_ADIPOGENESIS_EARLY_DN | 0.3263427 | 0.2076484 |
| TSAI_RESPONSE_TO_RADIATION_THERAPY | 0.4496202 | 0.2668487 |
| BMI1_DN_MEL18_DN.V1_UP | 0.2510806 | 0.1286998 |
| LIM_MAMMARY_LUMINAL_MATURE_DN | 0.3866089 | 0.2854703 |
| WILCOX_PRESPONSE_TO_ROGESTERONE_DN | 0.2788549 | 0.1764976 |
| PETROVA_PROX1_TARGETS_UP | 0.5455386 | 0.4020435 |
| CLASPER_LYMPHATIC_VESSELS_DURING_METASTASIS_DN | 0.446537 | 0.1615614 |
| MS_RESP_TO_WOUNDING_UP_IN_MAPKi_aPDL1_NR | 0.1685537 | 0.03557493 |
| DTP_BLOOD_VESS_DEVEL_UP | 0.3948108 | 0.2551939 |
| EP_BLOOD_VESS_DEVEL_DN_IN_R | 0.3690096 | 0.1249192 |
| MEL18_DN.V1_UP | 0.2981655 | 0.1947043 |
| LIEN_BREAST_CARCINOMA_METAPLASTIC | 0.3350505 | 0.2064535 |
| JACKSON_DNMT1_TARGETS_DN | 0.2207287 | 0.1007408 |
| STEGER_ADIPOGENESIS_DN | 0.2114487 | 0.1038486 |
| HOEK_INVASIVE_SIG | 0.3013897 | 0.1334731 |
| NAKAYAMA_SOFT_TISSUE_TUMORS_PCA2_UP | 0.2896541 | 0.1792381 |
| DTPP_CELL_ADHESION_UP | 0.2310315 | 0.1170249 |
| PLASARI_TGFB1_TARGETS_10HR_UP | 0.2796863 | 0.1783497 |
| ZWANG_CLASS_2_TRANSIENTLY_INDUCED_BY_EGF | 0.2338587 | 0.1260503 |
| HARRIS_HYPOXIA | 0.3340136 | 0.2255081 |

-continued

| | | |
|---|---|---|
| TURASHVILI_BREAST_LOBULAR_CARCINOMA_VS_DUCTAL_NORMAL_UP | 0.378983 | 0.2788209 |
| WEINMANN_ADAPTATION_TO_HYPOXIA_DN | 0.2444314 | 0.07841642 |
| PLX2D_CELL_ADHESION_UP | 0.1839791 | 0.08229793 |
| NAKAMURA_CANCER_MICROENVIRONMENT_UP | −0.1908011 | −0.315168 |
| WILLIAMS_ESR1_TARGETS_UP | 0.389565 | 0.2824854 |
| EP_RESP_TO_WOUNDING_DN_IN_R | 0.04477552 | −0.1384729 |
| DAVICIONI_TARGETS_OF_PAX_FOXO1_FUSIONS_DN | 0.1474971 | 0.04248538 |
| CHNG_MULTIPLE_MYELOMA_HYPERPLOID_UP | 0.5498142 | 0.6527332 |
| KIM_GLIS2_TARGETS_UP | 0.2598911 | 0.1276758 |
| PH_BLOOD_VESS_DEVEL_DN_IN_R | −0.04397603 | −0.2046115 |
| VALK_AML_CLUSTER_13 | 0.193455 | 0.08019806 |
| HARRIS_BRAIN_CANCER_PROGENITORS | −0.1469096 | −0.2705787 |
| PH_RESP_TO_WOUNDING_DN_IN_R | −0.2363218 | −0.3442289 |
| WANG_BARRETTS_ESOPHAGUS_UP | 0.2314685 | 0.1229598 |
| BERENJENO_TRANSFORMED_BY_RHOA_REVERSIBLY_DN | 0.3612462 | 0.2425698 |
| DTPP_RESP_TO_WOUNDING_UP | 0.2507667 | 0.09147198 |
| BACOLOD_RESISTANCE_TO_ALKYLATING_AGENTS_UP | 0.4607875 | 0.3449221 |

Table 3, Related to FIG. 2

| Geneset | Detail |
|---|---|
| MAPKi_INDUCED_EMT | EMT related genes in "Anastassiou_Cancer_Mesenchymal" and "Farmer_Breast_Cancer_Cluster_5" upregulated in at least 4 of 6 MAPKi resistant cell lines (M229R5, M229DDR, M238R1, SKMel28R1, SKMel28DDR1, M263R3) |
| MAPKi_INDUCED_ANGIOGENESIS | Angiogenesis related genes in at least three of the genesets: MAPKR_BLOOD_VESS_DEVEL_UP, DTPP_BLOOD_VESS_DEVEL_UP, DTP_BLOOD_VESS_DEVEL_UP, EP_BLOOD_VESS_DEVEL_DN_IN_R, PH_BLOOD_VESS_DEVEL_DN_IN_R upregulated in at least 4 of 6 MAPKi resistant cell lines (M229R5, M229DDR, M238R1, SKMel28R1, SKMel28DDR1, M263R3) |
| EP_BLOOD_VESS_DEVEL_DN_IN_R | Differentially expressed genes in the "Blood Vessel Development" GO term in a patient treated BRAFi + MEKi and anti-PD-1 that is lower than 90% of MAPKi treated ones |
| PH_BLOOD_VESS_DEVEL_DN_IN_R | Differentially expressed genes in the "Blood Vessel Development" GO term in a patient treated MEKi and anti-PD-1 that is lower than 90% of MAPKi treated ones |
| EP_RESP_TO_WOUNDING_DN_IN_R | Differentially expressed genes in the "Response to wounding" GO term in a patient treated BRAFi + MEKi and anti-PD-1 that is lower than 90% of MAPKi treated ones |
| PH_RESP_TO_WOUNDING_DN_IN_R | Differentially expressed genes in the "Response to wounding" GO term in a patient treated MEKi and anti-PD-1 that is lower than 90% of MAPKi treated ones |
| MS_RESP_TO_WOUNDING_UP_IN_MAPKi_aPDL1_NR | Differentially expressed genes in the "Response To Wounding" GO term in a patient treated BRAFi + MEKi and anti-PD-L1 that is higher than 90% of MAPKi treated ones |
| MS_RESP_TO_HYPOXIA_UP_IN_MAPKi_aPDL1_NR | Differentially expressed genes in the "Response to Hypoxia" GO term in a patient treated BRAFi + MEKi and anti-PD-L1 that is higher than 90% of MAPKi treated ones |
| POST_OP_WOUNDHEALING | Genes induced in post operation wound signature by Inkeles et al (Inkeles et al., JID2015). |

| | |
|---|---|
| HOEK_INVASIVE_SIG | Genes associated with melanoma invasiveness reported by Hoek et al (Cancer Res 2008) |
| HOEK_PROLIFEATIVE_SIG | Genes associated with melanoma proliferation reported by Hoek et al (Cancer Res 2008) |
| MAPKR_BLOOD_VESS_DEVEL_UP | Genes in the "Blood Vessel Development" GO term upregulated in at least 4 of 6 MAPKi resistant cell lines (M229R5, M229DDR, M238R1, SKMel28R1, SKMel28DDR1, M263R3) |
| DTPP_BLOOD_VESS_DEVEL_UP | Genes in the "Blood Vessel Development" GO term upregulated in 2 MAPKi-treated drug tolerant proliferating persister (DTPP) clones derived from M229 and M238 lines |
| DTP_BLOOD_VESS_DEVEL_UP | Genes in the "Blood Vessel Development" GO term upregulated in 2 MAPKi-treated drug tolerant persisters (DTP) derived from M229 and M238 lines |
| MAPKR_REG_CELL_PROLIF_UP | Genes in the "Regulation of cell proliferation" GO term upregulated in at least 4 of 6 MAPKi resistant cell lines (M229R5, M229DDR, M238R1, SKMel28R1, SKMel28DDR1, M263R3) |
| DTPP_REG_CELL_PROLIF_UP | Genes in the "Regulation of cell proliferation" GO term upregulated in 2 MAPKi-treated drug tolerant proliferating persister (DTPP) clones derived from M229 and M238 lines |
| DTPP_CELL_ADHESION_UP | Genes in the "Cell adhesion" GO term upregulated in 2 MAPKi-treated drug tolerant proliferating persister (DTPP) clones derived from M229 and M238 lines |
| PLX2D_CELL_ADHESION_UP | Genes in the "Cell adhesion" GO term upregulated in 2-days BRAFi-treatment (PLX4032) on M229 and M238 lines |
| DTPP_RESP_TO_WOUNDING_UP | Genes in the "Response to wounding" GO term upregulated in 2 MAPKi-treated drug tolerant proliferating persister (DTPP) clones derived from M229 and M238 lines |

| Geneset | Gene Listing |
|---|---|
| MAPKi_INDUCED_EMT | ADAM12, AURKA, BCAT1, BGN, CDH11, CENPF, CKS2, COL10A1, COL11A1, COL3A1, COL5A1, COL5A2, COL6A2, COL6A3, DTL, EPYC, FAP, FCGR1B, FN1, GREM1, IGHM, INHBA, KIF2C, LOXL2, LRRC15, MMP11, NCAPG, NID2, NUAK1, RRM2, SLC16A3, SULF1, TNFAIP6, VCAN |
| MAPKi_INDUCED_ANGIOGENESIS | ANPEP, BGN, BMP4, CDH5, COL3A1, CYR61, DLL4, EDN1, EMCN, ID1, KDR, NRP1, PLAU, PPAP2B, PROK2, PRRX2, RHOB, ROBO4, SOX17, SOX18, TGFB2, THBS1, THY1, VEGFA, VEGFC |
| EP_BLOOD_VESS_DEVEL_DN_IN_R | FGF9, PGF, S100A7, PDGFA, TNFRSF12A, EDN1, ANPEP, PRRX2, SRF, CDH5, TGFB2, SHB, HAND2, HMOX1, ROBO4, RHOB, IL1B, SOX18, SOX17, THBS1, ANGPT2, PPAP2B, CYR61, BMP4, KLF5, FLT1, JUNB, SLIT2, KDR, PROK2, VEGFC, BGN, MEOX2, EREG, ID1, JMJD6, DLL4, VEGFA |
| PH_BLOOD_VESS_DEVEL_DN_IN_R | EMCN, ACVRL1, LMO2, IL18, COL3A1, FGF10, ANPEP, ENPEP, PRRX2, GJA4, CXCL12, MMP2, CDH5, TGFB2, EDNRA, ACE, S1PR1, PTK2B, TDGF1, ROBO4, PLCD1, SOX18, SOX17, LOX, PPAP2B, COL18A1, BMP4, SELP, EPAS1, EGFL7, TGFBR2, COL15A1, TBX1, KDR, THY1, PROK2, BGN, ID1, PROK1, DLL4, PLXDC1, NOTCH4, ECSCR, COL1A2, ZFPM2, ATPIF1, ENG |
| EP_RESP_TO_WOUNDING_DN_IN_R | F2RL2, S100A8, PDGFB, PDGFA, F2RL1, S100A9, TLR2, CXCR1, CXCR2, IL11, TGFB2, CASP6, |

| | |
|---|---|
| | FOS, S1PR3, MYD88, LTB4R, HMOX1, SERPINE1, CCL3L3, IL1B, IRAK2, F11, IL18RAP, F10, PLAUR, PROK2, TNFAIP6, THBD, IL20RB, EREG, CARD18, SERPINB2, DSP, RIPK2, KDM6B, NGF, CXCL1, CCL3, CCL2, C9, CXCL3, DRD5, CXCL2, CCL8, BDKRB1, PF4, FPR2, CXCL6, TRIM72, CCL5, SRF, CCL7, TNFRSF1A, PCSK1, MEFV, CCL20, GP1BB, POU2F3, KLKB1, KRT1, CD24, THBS1, PTX3, KLK8, IL6, CEBPB, MAP2K3, S100A12, SOD2, CCL11, ITGA5, HBEGF, ID3, SELE, F2R |
| PH_RESP_TO_WOUNDING_DN_IN_R | F2RL3, ACVRL1, ADORA3, MASP1, TACR1, TGFB3, CXCR1, FGF10, CXCR2, MMRN1, TGFB2, CFHR1, CFP, CASP6, GP5, DYSF, AOAH, CCL3L3, CFH, MS4A2, LOX, LBP, CFD, XCR1, IL18RAP, PTGER3, CCL4L2, SERPING1, CDO1, MECOM, PROK2, SIGLEC1, CCR7, KLRG1, CD36, THBD, CD40LG, SERPINF2, PLA2G7, TFPI, AOC3, CYSLTR1, C6, COL3A1, C1R, PF4, GPR68, C1S, CCL5, IL23A, CCL23, MEFV, GP1BB, CNR2, NFATC4, NOX4, SELP, KL, EFEMP2, TGFBR2, IGF2, C4BPA, CCL16, CCL18, NOTCH3, VWF, ID3, ENG, SELE, IGFBP4, BMP6 |
| MS_RESP_TO_WOUNDING_UP_IN_MAPKi_aPDL1_NR | ADORA3, PDGFA, TLR2, ADORA1, TGFB1, IL10, CD97, S1PR3, GPX1, NLRC4, MYD88, CCL3L1, SERPINA3, CHST2, STXBP1, CCL4L2, SERPING1, CD40, GAL, PLAUR, C8G, ADM, CTSB, VSIG4, PLA2G2D, TPST1, GGCX, TF, CCL2, RTN4RL1, ADORA2A, CCL8, C1R, ITGB3, FPR2, TIMP3, TNFRSF4, CCL7, TNFRSF1A, SLC11A1, TNFRSF1B, GP1BB, IL10RB, RAC1, SCN9A, ENO3, C2, SCG2, FN1, SPP1, NOX4, PLAT, IL2RA, TNFSF4, STAT3, CCNB1, APOL2, CD55, TFRC, C1RL, SYT17 |
| MS_RESP_TO_HYPOXIA_UP_IN_MAPKi_aPDL1_NR | TF, CCL2, FLT1, ACTN4, SOCS3, PDGFA, ALDOC, EGLN3, NR4A2, TGFB1, DDIT4, CD38, HYOU1, HSP90B1, PLOD1, TFRC, ADM, PLOD2, VEGFA, PSEN2, MT3, ANGPTL4 |
| POST_OP_WOUNDHEALING | MMP3, PPBP, CXCL5, PTX3, PTHLH, TDO2, SPINK6, SPP1, MMP10, IL8, MME, GREM1, CTSZ, CXCL6, THBS1, SCG5, TFPI2, PTGS2, CXCL1, IL1A, PCSK1, AREG, IL13RA2, KIAA1199, CCL18, FST, LILRB1, CTNNB1, CLC, CXCL3, CEACAM6, LILRB2, ITCH, S100A12, CCDC102B, GLIS3, MS4A6E, RARRES1, NRG1, PHLDA1, MS4A4A, HAS2, TFEC, CCR1, ANXA3, CR1, IL1RL1, ADAM12, CCNA1, PLA2G7, ENPEP, SPON1, INHBA, STEAP1, STEAP4, TMSB15A, FGF7, PI15, C8orf4, CYBB, MED18, IGSF6, SAA1, RGS13, DEFB4A, SLC16A3, CCL3, AQPEP, CYP1B1, FAM20A, DKK1, IKBIP, SULF1, PXDN, HMOX1, FMO3, SERPINA3, NAA15, MSR1, CCL8, TMEFF1, KLK6, C13orf33, TNFAIP6, MGST1, SRSF6, SRGN, IGF2BP3, PCSK5, LAMC2, OLFML2B, NCEH1, FABP4, IL6, C5AR1, ALDH1A3, PDPN, LYZ, CD163, RAB12, RGS18, HBB, TIMP1, CNN3, FAM83A, CYR61, TNC, DPYSL3, PRR16, BAG2, DSEL, LIPG, PLAC8, CXCL2, FCER1G, SUSD5, NEXN, KLHL6, LMNB1, GPRC5A, TCEAL7, FPR1, APOBEC3A, ITGB6, HS3ST1, GBP6, ITGB5, ADIPOQ, CPXM1, PKP2, NNMT, OLR1, PPP3R1, BUB1, BCL2A1, MAP9, GCLM, S100P, F3, TMPRSS11E, BEND6, FCGR3A, DDX3Y, PI3, MS4A7, FCN1, TLR4, UCHL1, CYTL1, ST8SIA4, MMP9, ALDH1L2, DEPDC1, RNASE2, SPINK7 |
| HOEK_INVASIVE_SIG | ADAM12, AMOTL2, AXL, BIRC3, CDH13, CDK14, COL13A1, CRIM1, CRISPLD2, CYR61, DPYD, EFEMP1, EGFR, F2RL1, FGF2, FLNB, FOXD1, FST, FZD2, HEG1, HS3ST3A1, ITGA2, ITGA3, KCNMA1, LOXL2, MYOF, NRP1, NTM, NUAK1, OSMR, PDGFC, PODXL, S100A2, SLC22A4, SLIT2, SYNJ2, TCF4, THBS1, TLE4, TNFRSF11B, TPBG, TPM1, TRAM2, WNT5A, ZEB1 |
| HOEK_PROLIFEATIVE_SIG | ACP5, ADCY2, APOE, ASAH1, BIRC7, C21orf91, CAPN3, CDH1, CDK2, CDK5R1, CEACAM1, DAPK1, DCT, FAM174B, GALNT3, GNPTAB, GPM6B, GPR143, GPRC5B, GYG2, HPS4, INPP4B, IRF4, IVNS1ABP, KAZ, MBP, MICAL1, |

| | |
|---|---|
| | MITF, MLANA, MYO1D, NR4A3, OCA2, PHACTR1, PIR, PLXNC1, PMEL, RAB27A, RAB38, RGS20, RHOQ, RRAGD, SEMA6A, SIRPA, SLC45A2, ST3GAL6, STX7, TNFRSF14, TRPM1, TYR, TYRP1, WDR91, ZFYVE16 |
| MAPKR_BLOOD_VESS_DEVEL_UP | CAV1, NRP1, EPAS1, COL3A1, EDN1, COL5A1, CITED2, CDH13, VEGFC, S1PR1, JUN, CCBE1, PLCD3, FOXC2, COL1A1, FGF2, PLAU, CYR61 |
| DTPP_BLOOD_VESS_DEVEL_UP | CAV1, NRP1, LMO2, EDN1, COL3A1, MMP2, CXCL12, CITED2, AGT, CCBE1, PLCD3, RHOB, SEMA3C, THBS1, FGF2, CEACAM1, SCG2, CYR61, BMP4, COL18A1, EPAS1, MMP19, MYH9, ARHGAP24, COL5A1, THY1, CDH13, VEGFC, BGN, EPGN, JUN, VEGFA, NTRK2, COL1A2, COL1A1, PLAU |
| DTP_BLOOD_VESS_DEVEL_UP | CAV1, NRP1, LMO2, EDN1, COL3A1, TNFSF12, MMP2, CITED2, ANGPTL6, CXCR4, PLCD3, RHOB, QKI, SEMA3C, THBS1, CYR61, KLF5, COL18A1, EPAS1, MMP19, MYH9, ARHGAP24, COL5A1, ANXA2, THY1, SMO, CDH13, BGN, JUN, NTRK2, COL1A2, COL1A1, PLAU |
| MAPKR_REG_CELL_PROLIF_UP | CAV2, RBP4, CAV1, FOSL2, CCL2, NRP1, IGFBP7, CLU, EDN1, NFKBIA, IL15, IL34, SOX9, S1PR3, AGTR1, BDNF, S1PR1, SPEG, HLX, SERPINE1, NKX3-1, PDGFC, CD24, NRG1, RUNX2, FGF2, EGFR, PTGER2, TP53I11, IL6, IRS1, PDCD1LG2, MXD4, VEGFC, CDH13, TNFRSF9, ADRB2, JUN, F3, BNC1, IL12A, PDGFRB, TGFB1I1, PLAU, NGF |
| DTPP_REG_CELL_PROLIF_UP | RARRES3, FOSL2, FGF7, NRP1, PDGFB, FGF17, IGFBP7, EDN1, GJA1, FOXO4, CXADR, VIPR1, GLI3, IL31RA, AZGP1, AGTR1, WISP2, BDNF, GPC3, HLX, SERPINE1, PDGFC, NRG1, FGF2, EBI3, EGFR, PRKCA, PTPRK, PTGER2, CD40, IRS1, PDCD1LG2, MXD4, MYCN, TNS3, VEGFC, ADRB2, ADAMTS8, CCND2, CHRM1, F3, JUN, BTG4, GRN, VEGFA, IL12A, PDGFRB, NGFR, TGFB1I1, PMP22, NGF, CAV2, CAV1, CCL2, IFITM1, CLU, PTH1R, NFKBIA, KIT, BDKRB2, IL34, TIMP2, SOX9, ADA, VDR, IL12RB1, SPEG, AGT, ADRA2A, NKX3-1, CD24, THBS1, PPAP2A, RUNX2, SCG2, BMP4, COL18A1, IL6, TP53I11, TNFSF4, KAT2B, HCLS1, KLF11, TAX1BP3, CDH13, ATF3, NUPR1, EPGN, ETS1, DLX5, BNC1, FABP4, NR5A2, PLAU, KCTD11, F2R |
| DTPP_CELL_ADHESION_UP | CADM3, NRP1, THRA, CADM1, TLN2, IGFBP7, NPNT, FERMT2, BCAM, L1CAM, EDIL3, CXADR, CXCL12, VCL, NRCAM, AZGP1, WISP2, TGFBI, RHOB, LOXL2, NEGR1, BOC, CEACAM1, CDH24, CYR61, SPON1, EGFR, F11R, PTPRK, PCDHB7, NRXN2, CNTN6, SDK1, CPXM2, MYH9, THY1, JUP, CD36, CLDN1, LAMC2, TGFB1I1, PARVA, ACHE, CCL2, COL3A1, ITGA11, COL28A1, SPOCK1, IL32, CDH3, PCDHB11, SOX9, APLP1, ALCAM, COL17A1, LAMB2, SORBS1, FAT4, AGT, TTYH1, COL6A3, MSLN, CD24, THBS1, SELPLG, THBS3, APBA1, NPHP1, FN1, COL18A1, FLRT1, BGLAP, BMP1, COL13A1, ITGA1, NFASC, HSPG2, CELSR2, NID2, PCDH17, COL5A3, COL16A1, COL5A1, COL4A6, CDH13, ERBB2IP, ITGA5, PKP3, ADAM22, NTM, FEZ1 |
| PLX2D_CELL_ADHESION_UP | THRA, TLN2, FERMT2, L1CAM, BCAM, EDIL3, VCL, AZGP1, WISP2, RHOB, LOXL2, COL11A1, CYR61, PCDHB5, CNTN6, MYH9, JUP, NCAM2, CD36, CD99L2, TGFB1I1, PARVA, COL3A1, PCDHB15, NINJ1, PCDHB11, PKD1L1, CLDN14, ALCAM, SORBS1, ROPN1B, TTYH1, PVRL2, MSLN, ACAN, CD24, THBS1, GPNMB, APBA1, THBS3, COL18A1, MAG, FLRT1, ADAM23, ITGA1, HSPG2, CELSR3, NID2, PCDH17, COL16A1, COL5A3, PCDH18, COL14A1, FREM2, CDH19, CYFIP2, ANTXR1, ABL2 |
| DTPP_RESP_TO_WOUNDING_UP | F2RL2, NRP1, FGF7, PDGFB, F2RL1, TLR3, DYSF, SERPINE1, CFH, NRG1, FGF2, IRAK2, F11R, LY96, CD40, SDC1, CD36, F3, TFPI, NGFR, NGF, ACHE, CCL2, RTN4RL1, C3, CXCL3, |

| |
|---|
| COL3A1, CXCL2, CLU, C1R, BDKRB2, C1S, CDH3, MDK, TPM1, CCL26, IGSF10, LAMB2, NFATC4, CD24, THBS1, FN1, SCG2, IL6, TNFSF4, EFEMP2, MSTN, COL5A1, APOL3, PLSCR4, NUPR1, ITGA5, CD59, AOX1, PLA2G4C, HDAC9, PLAU, IGFBP4, F2R |

What is claimed is:

1. A method of administering anti-PD-1 therapy to a patient suffering from melanoma, the method comprising:
   (a) assaying a tumor sample obtained from the patient for a measure of anti-PD-1 therapy sensitivity, wherein the measure of sensitivity is selected from:
      (1) gene set enrichment/variation analysis of the tumor sample for:
         (i) mesenchymal transition genes (AXL, ROR2, WNT5A, LOXL2, TWIST2, TAGLN, FAP and the genes listed in Supplementary Table S2C under the gene set "MAPKi induced EMT") and negative marker of mesenchymal transition (CDH1),
         (ii) immunosuppressive genes (IL10, VEGFA, VEGFC), and monocyte and macrophage chemotactic genes (CCL2, CCL7, CCL8 and CCL13),
         (iii) cell adhesion genes (listed in Table S2C under the gene sets "DTPP_Cell_Adhesion_UP", "PLX2D_Cell_Adhesion_UP", and genes in table S2A which are members of the gene ontology term cell adhesion: NRP1, CCL2, NPNT, EDIL3, MMRN1, DCHS1, ITGBL1, WISP1, COL7A1, COL6A3, COL6A2, COL6A1, COL12A1, ESAM, COL8A1, LOXL2, HAPLN1, EGFL6, COL13A1, SDK1, NID1, AJAP1, SSPN, CERCAM, EMILIN1, CTNNA2, TNFAIP6, CDH13, HAS1, LAMC3, ITGA5, ITGA8, FBLN5, FBLN7, ROR2, VCAN, JAM2,
         (iv) extracellular membrane organization genes (genes listed in table S2A which are members of the gene ontology term extracellular matrix organization: LUM, ELN, OLFML2A, NID1, SERPINH1, COL5A2, EMILIN1, ITGA8, FBLN5, FOXF1, COL6A2, COL12A1, FOXC2),
         (v) wound healing genes (listed in Table S2C under the gene sets "EP_RESP_TO_WOUNDING_DN_IN_R", "PH_RESP_TO_WOUNDING_DN_IN_R", "MS_RESP_TO_WOUNDING_UP_IN_MAPKi_aPDL1_NR", "DTPP_RESP_TO_WOUNDING_UP", and genes in table S2A which are members of the gene ontology term response to wounding: F2RL2, F2RL3, CCL3, NRP1, CCL2, CCL8, MECOM, MMRN1, GAL, TIMP3, CCL7, IL10, PLAUR, IL17D, TNFAIP6, CCL13, PROCR, ITGA5, F3, FBLN5, SERPINE1, NFATC4, VCAN, ID3, NGF), and/or
         (vi) angiogenesis genes (listed in Table S2C under the gene sets "MAPKi_INDUCED_ANGIOGENESIS", "EP_BLOOD_VESS_DEVEL_DN_IN_R", "PH_BLOOD_VESS_DEVEL_DN_IN_R", "MAPKR_BLOOD_VESS_DEVEL_UP", "DTPP_BLOOD_VESS_DEVEL_UP", "DTP_BLOOD_VESS_DEVEL_UP", and genes in table S2A which are members of the gene ontology term vasculature development: NRP1, FLT1, EFNB2, PRRX1, ENPEP, MMP2, GJA5, EDNRA, CDH13, VEGFC, ACE, ID1, FOXF1, VEGFA, FOXC2, ANGPT2);
      wherein the gene set enrichment/variation analysis comprises determining a first enrichment similarity (variation) score indicative of statistical similarity between the level of mRNA expression, protein expression, and/or protein phosphorylation/acetylation of one or more (e.g., four, in one embodiment) of the genes listed in (i) to (vi) and a first reference set representative of tumors known to be sensitive to anti-PD-1 therapy, and determining a second enrichment similarity (variation) score indicative of statistical similarity between the level of mRNA expression, protein expression, and/or protein phosphorylation/acetylation of one or more of the genes listed in (i) to (vi) and a second reference set representative of tumors known to be unresponsive to anti-PD-1 therapy;
      (2) non-synonymous mutations in BRCA2 and/or MTOR (mammalian target of rapamycin) genes, and/or loss of function indicated by mRNA expression loss and/or protein based assays of same; and
      (3) increased mutational load in one or more cell adhesion-associated genes (genes in Table S2C under the gene sets "DTPP_Cell_Adhesion_UP", "PLX2D_Cell_Adhesion_UP", genes in table S2A which are members of the cell adhesion gene ontology terms: NRP1, CCL2, NPNT, EDIL3, MMRN1, DCHS1, ITGBL1, WISP1, COL7A1, COL6A3, COL6A2, COL6A1, COL12A1, ESAM, COL8A1, LOXL2, HAPLN1, EGFL6, COL13A1, SDK1, NID1, AJAP1, SSPN, CERCAM, EMILIN1, CTNNA2, TNFAIP6, CDH13, HAS1, LAMC3, ITGA5, ITGA8, FBLN5, FBLN7, ROR2, VCAN, JAM2); and
   (b) selecting samples that exhibit a higher first variation score and/or a lower second variation score in (1), and/or at least one measure of sensitivity identified in (2) and/or (3); and
   (c) administering anti-PD-1 therapy to the patient whose sample was selected in (b).

2. The method of claim 1, wherein the assaying of step (a) comprises assaying at least two of the measures listed in step (a).

3. The method of claim 2, wherein the at least two measures are assayed on the same tumor sample.

4. The method of claim 1, wherein the gene set variation analysis comprises generating a score that represents normalized expression levels of at least four of the genes listed in step (a)(1).

5. The method of claim 1, which is performed prior to treatment with combined anti-PD-1 therapy.

6. The method of claim 1, which is performed after treatment with anti-PD-1 therapy.

7. The method of claim 1, which is performed during disease progression or clinical relapse on anti-PD-1 therapy.

8. The method of claim 1, which is performed after suspension of anti-PD-1 therapy.

9. The method of claim 1, wherein the melanoma is advanced metastatic melanoma.

10. The method of claim 1, wherein the tumor sample is selected from tissue, bodily fluid, blood, tumor biopsy, spinal fluid, and needle aspirate.

11. The method of claim 1, wherein the assaying comprises whole transcriptome sequencing, antibody based protein quantifications, mass spectrometry based protein quantification, targeted mRNA sequencing, and/or real-time RT-PCR.

12. The method of claim 1, wherein the assaying comprises Sanger sequencing, targeted sequencing and/or whole exome/genome sequencing.

13. The method of claim 1, wherein the anti-PD-1 therapy is administered in conjunction with combinatorial therapy.

14. The method of claim 13, wherein the anti-PD-1 therapy comprises treatment with an anti-PD-1 antibody (nivolumab/BMS-936558/MDX-1106, pembrolizumab/MK-3475, Pidilizumab), and/or an anti-PD-L1 antibody (BMS-986559, MPDL3280A, and MEDI4736).

15. A method of treating a patient suffering from melanoma, the method comprising assaying a tumor sample obtained from the patient for a marker of sensitivity to anti-PD-1 therapy, and either administering anti-PD-1 therapy if the patient is positive for a marker of sensitivity to anti-PD-1 therapy, or administering alternative therapy if the patient is not positive for a marker of sensitivity to anti-PD-1 therapy, wherein the marker of sensitivity to anti-PD-1 therapy is selected from the measures according to claim 1(a).

16. The method of claim 15, wherein the alternative therapy is selected from:
(a) MAPK targeted therapy (mutant BRAF inhibitors: Vemurafenib/PLX4032, Dabrafenib, Encorafenib/LGX818, MEK inhibitors: Trametinib/GSK1120212, Selumetinib/AZD6244, MEK162/Binimetinib, Cobimetinib/GDC0973, PD0325901, ERK inhibitors: SCH772984, VTX-Ile, Pan RAF inhibitors: Sorafenib, CCT196969, CCT241161, PLX7904 and PLX8394);
(b) anti-CTLA-4 immunotherapy (Ipilimumab);
(c) anti-angiogenic therapy (Sorafenib, Sunitinib, Pazopanib, Everolimus, Bevacizumab, Ranibizumab, PLX3397); and
(d) any combination of the above with or without anti-PD-1 antibody (nivolumab/BMS-936558/MDX-1106, pembrolizumab/MK-3475, Pidilizumab) or anti-PD-L1 antibody (BMS-986559, MPDL3280A, and MEDI4736).

17. A method of selecting somatic mutanomes and transcriptomes of melanoma biopsies, the method comprising:
(a) assaying a tumor sample obtained from the patient for a measure of anti-PD-1 therapy sensitivity, wherein the measure of sensitivity is selected from:
(1) gene set enrichment/variation analysis of the tumor sample for:
(i) mesenchymal transition genes (AXL, ROR2, WNT5A, LOXL2, TWIST2, TAGLN, FAP and the genes listed in Supplementary Table S2C under the gene set "MAPKi induced EMT") and negative marker of mesenchymal transition (CDH1),
(ii) immunosuppressive genes (IL10, VEGFA, VEGFC), and monocyte and macrophage chemotactic genes (CCL2, CCL7, CCL8 and CCL13),
(iii) cell adhesion genes (listed in Table S2C under the gene sets "DTPP_Cell_Adhesion_UP", "PLX2D_Cell_Adhesion_UP", and genes in table S2A which are members of the gene ontology term cell adhesion: NRP1, CCL2, NPNT, EDIL3, MMRN1, DCHS1, ITGBL1, WISP1, COL7A1, COL6A3, COL6A2, COL6A1, COL12A1, ESAM, COL8A1, LOXL2, HAPLN1, EGFL6, COL13A1, SDK1, NID1, AJAP1, SSPN, CERCAM, EMILIN1, CTNNA2, TNFAIP6, CDH13, HAS1, LAMC3, ITGA5, ITGA8, FBLN5, FBLN7, ROR2, VCAN, JAM2,
(iv) extracellular membrane organization genes (genes listed in table S2A which are members of the gene ontology term extracellular matrix organization: LUM, ELN, OLFML2A, NID1, SERPINH1, COL5A2, EMILIN1, ITGA8, FBLN5, FOXF1, COL6A2, COL12A1, FOXC2),
(v) wound healing genes (listed in Table S2C under the gene sets "EP_RESP_TO_WOUNDING_DN_ IN_R", "PH_RESP_TO_WOUNDING_DN_ IN_R", "MS_RESP_TO_WOUNDING_UP_IN_MAPKi_aPDL1_NR", "DTPP_RESP_TO_WOUNDING_UP", and genes in table S2A which are members of the gene ontology term response to wounding: F2RL2, F2RL3, CCL3, NRP1, CCL2, CCL8, MECOM, MMRN1, GAL, TIMP3, CCL7, IL10, PLAUR, 1L17D, TNFAIP6, CCL13, PROCR, ITGA5, F3, FBLN5, SERPINE1, NFATC4, VCAN, ID3, NGF), and/or
(vi) angiogenesis genes (listed in Table S2C under the gene sets "MAPKi_INDUCED_ANGIOGENESIS", "EP_BLOOD_VESS_DEVEL_DN_IN_R", "PH_BLOOD_VESS_DEVEL_DN_IN_R", "MAPKR_BLOOD_VESS_DEVEL_UP", "DTPP_BLOOD_VESS_DEVEL_UP", "DTP_BLOOD_VESS_DEVEL_UP", and genes in table S2A which are members of the gene ontology term vasculature development: NRP1, FLT1, EFNB2, PRRX1, ENPEP, MMP2, GJA5, EDNRA, CDH13, VEGFC, ACE, ID1, FOXF1, VEGFA, FOXC2, ANGPT2);
wherein the gene set enrichment/variation analysis comprises determining a first enrichment similarity (variation) score indicative of statistical similarity between the level of mRNA expression, protein expression, and/or protein phosphorylation/acetylation of one or more (e.g., four, in one embodiment) of the genes listed in (i) to (vi) and a first reference set representative of tumors known to be sensitive to anti-PD-1 therapy, and determining a second enrichment similarity (variation) score indicative of statistical similarity between the level of mRNA expression, protein expression, and/or protein phosphorylation/acetylation of one or more of the genes listed in (i) to (vi) and a second reference set representative of tumors known to be unresponsive to anti-PD-1 therapy;
(2) non-synonymous mutations in BRCA2 and/or MTOR (mammalian target of rapamycin) genes, and/or loss of function indicated by mRNA expression loss and/or protein based assays of same; and (3) increased mutational load in one or more cell adhesion-associated genes (genes in Table S2C under the gene sets "DTPP_Cell_Adhesion_UP", "PLX2D_Cell_Adhesion_UP", genes in table S2A which are members of the cell adhesion gene ontology terms: NRP1, CCL2, NPNT, EDIL3, MMRN1, DCHS1, ITGBL1, WISP1, COL7A1, COL6A3, COL6A2, COL6A1, COL12A1, ESAM, COL8A1, LOXL2, HAPLN1, EGFL6, COL13A1, SDK1, NID1, AJAP1, SSPN, CERCAM, EMILIN1, CTNNA2, TNFAIP6, CDH13, HAS1, LAMC3, ITGA5, ITGA8, FBLN5, FBLN7, ROR2, VCAN, JAM2); and (b) selecting samples that exhibit a higher first variation score and/or a lower second variation score in (1), and/or at least one measure of sensitivity identified in (2) and/or (3).

18. The method of claim 17, wherein the tumor sample is selected from tissue, bodily fluid, blood, tumor biopsy, spinal fluid, and needle aspirate.

19. The method of claim 17, wherein the assaying comprises whole transcriptome sequencing, antibody based protein quantifications, mass spectrometry based protein quantification, targeted mRNA sequencing, and/or real-time RT-PCR.

20. The method of claim 17, wherein the assaying comprises Sanger sequencing, targeted sequencing and/or whole exome/genome sequencing.

* * * * *